US012679817B2

(12) United States Patent
Xin

(10) Patent No.: US 12,679,817 B2
(45) Date of Patent: Jul. 14, 2026

(54) PROCESSES FOR THE PREPARATION OF THE ENANTIOMERS OF 3,4-METHYLENEDIOXYMETHAMPHETAMINE (MDMA) AND N-METHYL-1,3-BENZODIOXOLYLBUTANAMINE (MBDB)

(71) Applicant: PHARMALA BIOTECH INC., Vancouver (CA)

(72) Inventor: Tao Xin, Woodbridge (CA)

(73) Assignee: PHARMALA BIOTECH INC., Vancouver (CA)

( * ) Notice: Subject to any disclaimer, the term of this patent is extended or adjusted under 35 U.S.C. 154(b) by 431 days.

(21) Appl. No.: 18/289,586

(22) PCT Filed: May 6, 2022

(86) PCT No.: PCT/CA2022/050719

§ 371 (c)(1),
(2) Date: Nov. 6, 2023

(87) PCT Pub. No.: WO2022/232948

PCT Pub. Date: Nov. 10, 2022

(65) Prior Publication Data

US 2024/0270710 A1 Aug. 15, 2024

Related U.S. Application Data

(60) Provisional application No. 63/305,794, filed on Feb. 2, 2022, provisional application No. 63/203,099, filed on Jul. 8, 2021, provisional application No. 63/201,609, filed on May 6, 2021.

(51) Int. Cl.
*C07D 317/60* (2006.01)

(52) U.S. Cl.
CPC .................................. *C07D 317/60* (2013.01)

(58) Field of Classification Search
CPC .................................................... C07D 317/60
See application file for complete search history.

(56) References Cited

U.S. PATENT DOCUMENTS

| | | | |
|---|---|---|---|
| 5,075,296 | A | 12/1991 | Koga et al. |
| 6,946,547 | B2 | 9/2005 | Rouhani et al. |
| 7,101,980 | B2 | 9/2006 | Hui et al. |
| 2014/0012005 | A1 | 1/2014 | Darses et al. |

FOREIGN PATENT DOCUMENTS

| | | | |
|---|---|---|---|
| CN | 109134481 A | | 1/2019 |
| CN | 110655500 A1 | | 1/2020 |
| WO | 0318542 A1 | | 3/2003 |
| WO | 2013014287 A2 | | 1/2013 |

OTHER PUBLICATIONS

Felim et al. (Chem. Res. Toxicol. 2010; 23: 211-219) (Year: 2010).*
International Search Report and Written Opinion mailed Sep. 9, 2022 in respect of PCT/CA2022/050719.
Cordier et al., "Product Class 7: 1,3-Dioxetanes and 1,3-Dioxolanes", Science of Synthesis, 2007, vol. 29, pp. 407-486, p. 449.
Lentini et al., "(S)-Ethyl 2-(tert-butoxycarbonylamino)-3-(2-iodo-4,5-methylenedioxyphenyl)propanoate", Molbank, Feb. 21, 2019, pp. 1-4.
Registry No. 1187755-56-1, "(αR)-α-[[(phenylmethoxy)carbonyl]amino]-1,3-Benzodioxole-5-propanoic acid methyl ester", Oct. 9, 2009.
Grosset et al., "Determination of Absolute Configuration of Fasidotril, a Potent Dual ACE/NEP Inhibitor", Tetrahedron: Asymmetry, Aug. 15, 2003, vol. 14(16), pp. 2335-2337.
Schulze, "Synthesis of 2-Arylethylamines by the Curtius Rearrangement", Synthetic Communications, Apr. 23, 2010, vol. 40(10), pp. 1461-1476.
Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time", The Journal of Neuroscience, May 1, 2011, vol. 31(19), pp. 7190-7198.

(Continued)

*Primary Examiner* — Brandon J Fetterolf

(74) *Attorney, Agent, or Firm* — Smart & Biggar LP; Sandra Marone

(57) ABSTRACT

The present application includes processes for preparing the (R)- or (S)-enantiomers of 3,4-methylenedioxymethamphetamine (MDMA) and the (R)- or (S)-enantiomers of N-methyl-1,3-benzodioxolylbutanamine (MBDB) starting with the alkyl esters of 3,4-dihydroxy-L-phenylalanine (L-DOPA) or alkyl esters of 3,4-dihydroxy-L-phenylalanine (D-DOPA), respectively. The present application also includes novel intermediate compounds useful in the preparation of the enantiomers of MDMA and MBDB.

(R-MDMA)

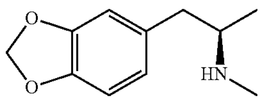

(R-MBDB)

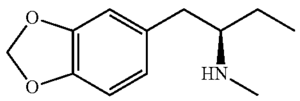

(S)-MDMA

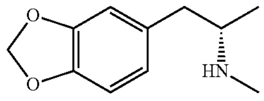

(S)-MBDB

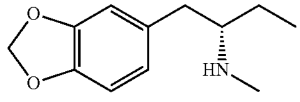

20 Claims, No Drawings

(56) References Cited

OTHER PUBLICATIONS

Monte et al., "Synthesis and Pharmacological Examination of Benzofuran, Indan, and Tetralin Analogues of 3,4-(Methylenedioxy)amphetamine", Journal of Medicinal Chemistry, Nov. 1, 1993, vol. 36(23), pp. 3700-3706.
Van Aerts et al., "N-Methyl-1-(1-3-benzodioxol-5-yl)-2-butanamine (MBDB): its properties and possible risks", Addiction Biology (2000) 5, 269-282.
Nichols, "Differences Between the Mechanism of Action of MDMA, MBDB, and the Classic Hallucinogens. Identification of a New Therapeutic Class: Entactogens", Journal of Psychoactive Drugs, vol. 18(4) Oct.-Dec. 1986.
Pitts et al., "(±)-MDMA and its enantiomers: potential therapeutic advantages of R(−-)-MDMA", Psychopharmacology, vol. 235, pp. 377-392(2018).
Dunlap et al., "Dark Classics in Chemical Neuroscience: 3,4-Methylenedioxymethamphetamine (MDMA)", ACS Chem Neurosci., 9(10): 2408-2427, Oct. 17, 2018.
Lewis, "A Medicinal Chemistry Investigation of 3,4-methylenedioxymethamphetamine (MDMA)", PhD Thesis, 2011.
Felim et al., "Synthesis and in vitro cytotoxicity profile of the R-enantiomer of 3,4-dihydroxymethamphetamine (R-(−)HHMA): comparison with related catecholamines", Chem Res Toxicol, 23(1):211-9, Jan. 2010.
Pizarro et al., "Synthesis and capillary electrophoretic analysis of enantiomerically enriched reference standards of MDMA and it main metabolites", Bioorg. Med. Chem. 10, 2002, 1085-1092.
Nichols et al., "Derivatives of 1-(1, 3-benzodioxol-5-yl)-2-butanamine: representative of a novel therapeutic class", J. Med. Chem. 1986, 29, 2009-215.
Tohala et al., "Chiral Resolution Capabilities of DNA Oligonucleotides", Anal. Chem. 2015, 87, 5491-5495.
MAPS Bulletin 2020: The Commercial Chemistry of MDMA: From Research to Patient Access.
Llabres et al., "Molecular basis of the selective binding of MDMA enantiomers to the alpha4beta2 nicotinic receptor subtype: synthesis, pharmacological evaluation and mechanistic studies", European Journal of Medicinal Chemistry, 81 (2014) 35-46.
Effenberger et al., "Stereoselective Synthesis of (S)-3,4-Methylenedioxyamphetamines from (R)-Cyanohydrins", Chemistry—A European Journal vol. 3, Issue 8, pp. 1370-1374.
Ribiero et al., "Chiral Drug Analysis in Forensic Chemistry: an Overview", Molecules 2018, 23(2), 262.
Schwaninger et al., Development and validation of LC-HRMS and GC-NICI-MS methods for stereoselective determination of MDMA and its phase I and II metabolites in human urine, Journal of Mass Spectrometry (2011), 46(7), 603-614.
Lourenco et al., "Chiral separation of 3,4-methylenedioxymethamphetamine (MDMA) enantiomers using batch chromatography with peak shaving recycling and its effects on oxidative stress status in rat liver", Journal of Pharmaceutical and Biomedical Analysis, vol. 73, Jan. 25, 2013, pp. 13-17.
Moldovan et al. "(+) or (−)-1-(9-fluorenyl)ethyl chloroformate as chiral derivatizing agent: A review", Journal of Chromatography A, vol. 1513, Sep. 1, 2017, pp. 1-17.
Martins et al., "Sensitive, rapid and validated gas chromatography/negative ion chemical ionization-mass spectrometry assay including derivatization with a novel chiral agent for the enantioselective quantification of amphetamine-type stimulants in hair", J. Chromatogr B. Analyt Technol Biomed Life Sci Oct. 2, 2006, 842(2):98-105.
Hashimoto et al., "Synthesis of racemic, S(+)- and R(−)-N-[methyl-3H]3,4-methylenedioxymethamphetamine", Journal of radiolabelled compounds, vol. 28, Issue 4, 1990, pp. 465-469.
Guillarme et al., Fast Chiral Separation of Drugs using Columns Packed with Sub-2 Im Particles and Ultra-High Pressure, 2010, Chirality 22:320-330.
Schappler et al., "Enhanced method performances for conventional and chiral CE-ESI/MS analyses in plasma", Electrophoresis (2006), 27(8), 1537-1546.
Nichols, "Chemistry and Structure-Activity Relationships of Psychedelics", 2017.

* cited by examiner

PROCESSES FOR THE PREPARATION OF THE ENANTIOMERS OF 3,4-METHYLENEDIOXYMETHAMPHETAMINE (MDMA) AND N-METHYL-1,3-BENZODIOXOLYLBUTANAMINE (MBDB)

RELATED APPLICATIONS

This application is a National Stage of International Application No. PCT/CA2022/050719 filed on May 6, 2022, which claims the benefit of priority of U.S. provisional patent application No. 63/201,609 filed on May 6, 2021, U.S. provisional patent application No. 63/203,009 filed on Jul. 8, 2021 and U.S. provisional patent application No. 63/305,794 filed on Feb. 2, 2022, the contents of each of which are incorporated herein by reference in their entirety.

FIELD

The present application is related to processes for preparing (R)- or (S)-3,4-methylenedioxymethamphetamine ((R)-MDMA/(S)-MDMA) and (R)- or (S)—N-methyl-1,3-benzodioxolylbutanamine ((R)-MBDB/(S)-MBDB). In particular, the processes use 3,4-dihydroxy-L-phenylalanine (L-DOPA) alkyl ester or 3,4-dihydroxy-D-phenylalanine (D-DOPA) alkyl ester as the starting material. The present application also relates to compounds useful in the preparation of the enantiomers of MDMA and MBDB.

BACKGROUND 3,4-Methylenedioxymethamphetamine (MDMA), commonly known as ecstasy (E) or molly, is a psychoactive drug first developed in 1912 by Merck. MDMA is often used recreationally today. However, an initial use of MDMA was as an adjunct to psychotherapy. More recently, MDMA has been studied in various clinical trials, for example, investigating MDMA-assisted psychotherapy for posttraumatic stress disorder (PTSD), anxiety related to advanced-stage illness, and social anxiety in autistic adults. MDMA has now been grated Breakthrough Therapy Designation to MDMA for the treatment of PTSD by the United States Food and Drug Administration (FDA).

MDMA is generally available and consumed as a racemate. However, each enantiomer has been shown to provide different pharmacological and pharmacokinetic profiles. In fact, evidence suggests that R(−)-MDMA may provide an improved therapeutic index maintaining the therapeutic effects of (±)-MDMA with a reduced side effect profile (Pitts et al. Psychopharmacology 235, 377-392, 2018).

There are many methods available to synthesize MDMA including several methods to synthesize enantiopure MDMA using, for example, chiral salts, chiral synthesis, or using chiral auxiliaries [e.g. Dunlap et al (2018), ACS Chem Neurosci; 9(10): 2408-2427; Llabrés et al (2014), European J. of Med. Chem. 81 (2014) 35-46; Huot et al (2011), J Neurosci. (2011) May 11; 31(19): 7190-7198]. Felim et al. disclose a synthesis of an MDMA metabolite using L-DOPA as the chiral source [Felim et al., Chem Res Toxicol. 2010 23(1):211-9.]

N-methyl-1,3-benzodioxolylbutanamine (MBDB) commonly known as Eden or Methyl-J, is an analogue of MDMA which has an ethyl group instead of a methyl group attached to the alpha carbon next to the amine. Like MDMA, MBDB is also classified as an entactogen.

SUMMARY

The present application includes processes for preparing the (R) or (S) enantiomers of 3,4-methylenedioxymethamphetamine (MDMA) and N-methyl-1,3-benzodioxolylbutanamine (MBDB), for example starting from 3,4-dihydroxy-L-phenylalanine (L-DOPA) alkyl esters or 3,4-dihydroxy-D-phenylalanine (D-DOPA) alkyl esters, respectively.

Accordingly, the present application includes a process for preparing a compound of Formula (R)-I or (S)-I:

(R)-I

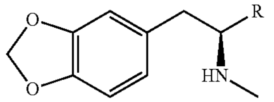

or (S)-I

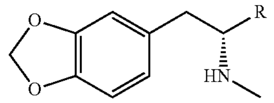

wherein

R is selected from $CH_3$ and $CH_2CH_3$;

the process comprising:

protecting the amino group of 3,4-dihydroxy-L-phenylalanine (L-DOPA) $C_{1-4}$alkyl ester of Formula (S)-A, or the amino group of 3,4-dihydroxy-D-phenylalanine (D-DOPA) $C_{1-4}$alkyl ester of Formula (R)-A:

(S)-A

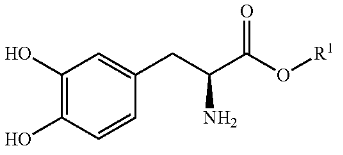

or (R)-A

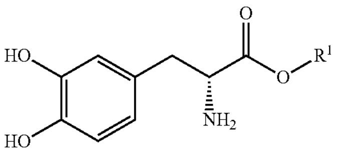

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

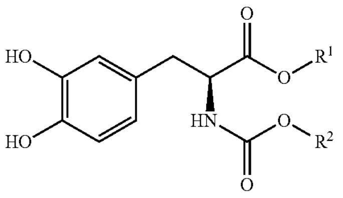

or

-continued (R)-B

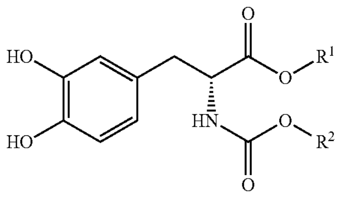

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

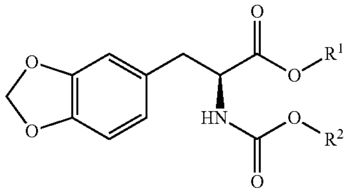

or (R)-C

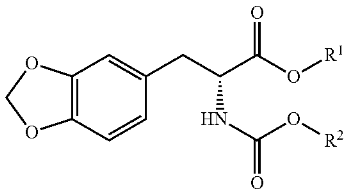

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

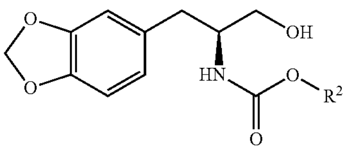

or (R)-D

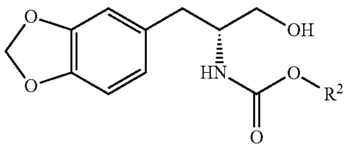

wherein $R^2$ is $C_{1-4}$alkyl or $CH_2Ph$;

when R is $CH_2CH_3$, further oxidizing the compound of Formula (S)-D or (R)-D to provide a compound of Formula (S)-$D^{ox}$ or (R)-$D^{ox}$, respectively; and (S)-$D^{ox}$

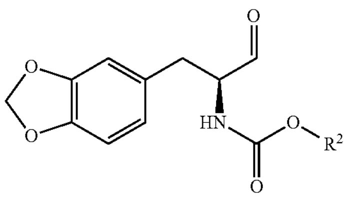

or (R)-$D^{ox}$

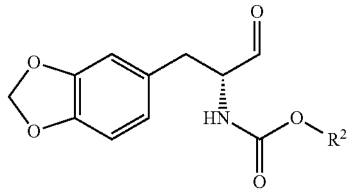

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

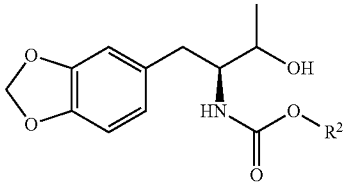

or (R)-D'

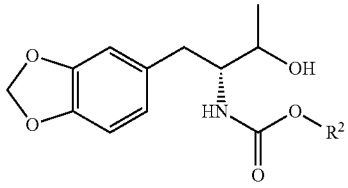

wherein $R^2$ is $C_{1-4}$alkyl or $CH_2Ph$; and reacting the compound of Formula (S)-D or (R)-D with a chlorinating agent to provide a compound of Formula (S)-E or (R)-E, respectively, or reacting the compound Formula of (S)-D' or (R)-D' with a chlorinating agent to provide a compound of Formula (S)-E or (R)-E', respectively:

(S)-E

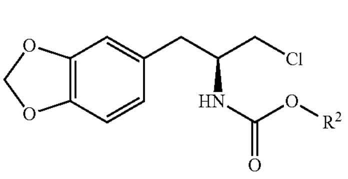

or (R)-E

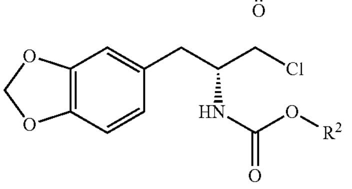

or

-continued (S)-E′

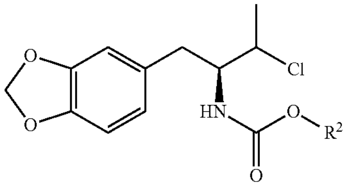

or (R)-E′

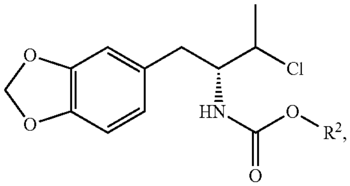

, wherein $R^2$ is $C_{1-4}$alkyl or $CH_2Ph$; or when R is $CH_2CH_3$, hydrolyzing the compound of Formula (S)-C or (R)-C to provide the compound of Formula (S)-C' or (R)-C', respectively;

(S)-C′

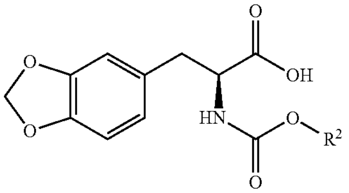

or (R)-C′

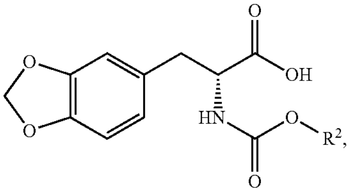

, wherein $R^2$ is $C_{1-4}$alkyl or $CH_2Ph$; and converting the compound of Formula (S)-C' or (R)-C' to the compound of Formula (S)-E" or (R)-E", respectively (S)-E″

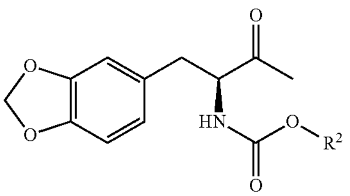

or (R)-E″

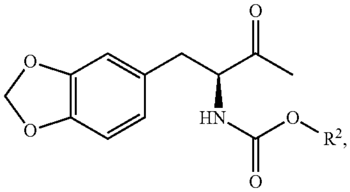

, wherein $R^2$ is $C_{1-4}$alkyl or $CH_2Ph$; and reacting the compound of Formula (S)-E or (R)-E with a reducing agent to provide the compound of Formula (R)-I or (S)-I, respectively, wherein R is $CH_3$, reacting the compound of Formula (S)-E' or (R)-E' with a reducing agent to provide the compound of Formula (R)-I or (S)-I, respectively, wherein R is $CH_2CH_3$, or reacting the compound of Formula (S)-E" or (R)-E" with a reducing agent to provide the compound of Formula (R)-I or (S)-I, respectively, wherein R is $CH_2CH_3$.

The present application also includes a process for preparing (R)—N-methyl-1,3-benzodioxolylbutanamine ((R)-MBDB) or (S)—N-methyl-1,3-benzodioxolylbutanamine ((S)-MBDB):

(R)-MBDB

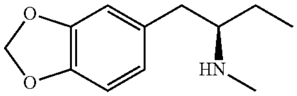

or (S)-MBDB

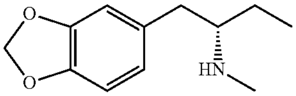

the process comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

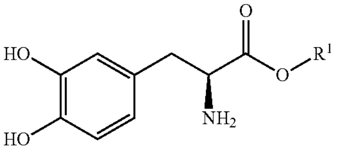

or (R)-A

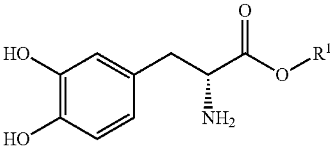

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

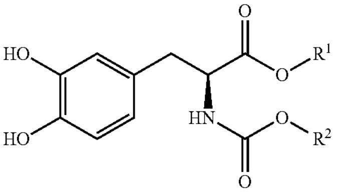

or

-continued (R)-B

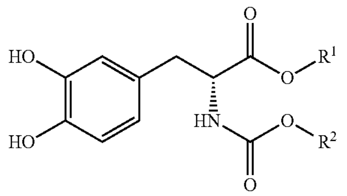

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

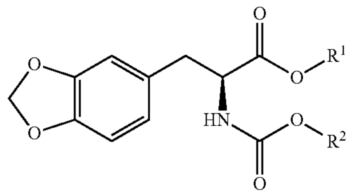

or (R)-C

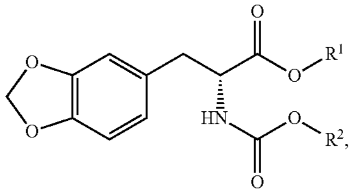

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

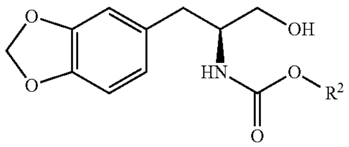

or (R)-D

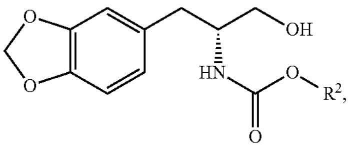

wherein $R^2$ is $C_{1-4}$alkyl or $CH_2Ph$;

oxidizing the compound of Formula (S)-D or (R)-D to provide a compound of Formula (S)-$D^{ox}$ or (R)-$D^{ox}$, respectively;

(S)-$D^{OX}$

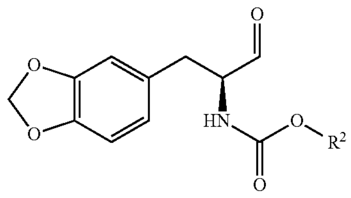

or (R)-$D^{OX}$

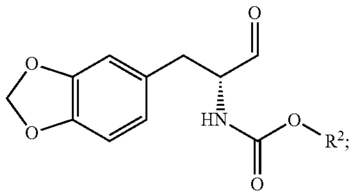

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

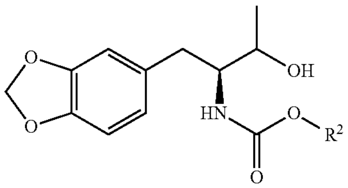

or (R)-D'

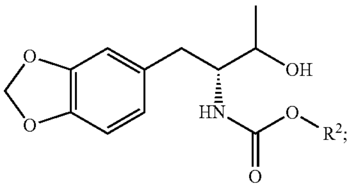

wherein $R^2$ is $C_{1-4}$alkyl or $CH_2Ph$;

reacting the compound of Formula (S)-D' or (R)-D' with a chlorinating agent to provide a compound of Formula (S)-E' or (R)-E', respectively:

(S)-E'

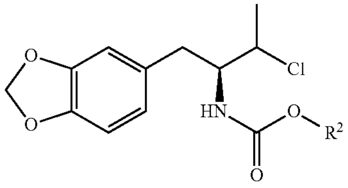

or (R)-E'

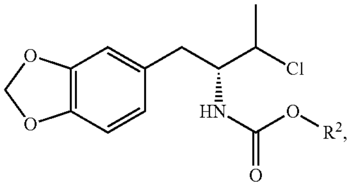

wherein $R^2$ is $C_{1-4}$alkyl or $CH_2Ph$; and reacting the compound of Formula (S)-E' or (R)-E' with a reducing agent to provide R-MBDB or (S)-MBDB, respectively.

The present application also includes a process for preparing (R)—N-methyl-1,3-benzodioxolylbutanamine ((R)-MBDB)

(R)-MBDB

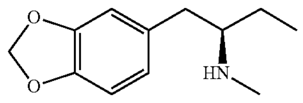

the process comprising:

protecting the amino group of 3,4-dihydroxy-L-phenylalanine (L-DOPA) $C_{1-4}$alkyl ester of Formula (S)-A:

(S)-A

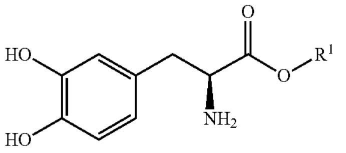

wherein $R^1$ is $C_{1-4}$alkyl, with a $C_{1-4}$alkoxycarbonyl protecting group or a benzyloxy carbonyl protecting group to provide a compound of Formula (S)-B:

(S)-B

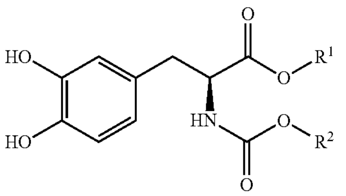

wherein $R^1$ is $C_{1-4}$alkyl, and $R^2$ is $C_{1-4}$alkyl or $CH_2Ph$;

cyclizing the compound of Formula B to provide a compound of Formula (S)-(S)-C:

(S)-C

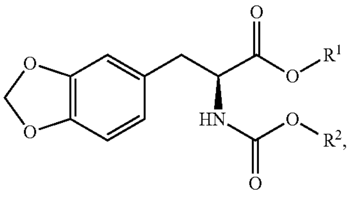

wherein $R^1$ is $C_{1-4}$alkyl, and $R^2$ is $C_{1-4}$alkyl or $CH_2Ph$;

hydrolyzing the compound of Formula (S)-C to provide the compound of Formula (S)-C';

(S)-C'

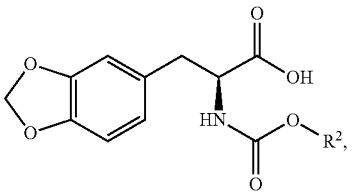

wherein $R^2$ is $C_{1-4}$alkyl or $CH_2Ph$;

converting the compound of Formula (S)-C' to the compound of Formula (S)-E"

(S)-E"

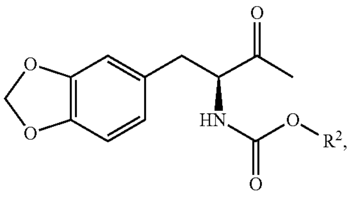

wherein $R^2$ is $C_{1-4}$alkyl or $CH_2Ph$; and reacting the compound of Formula (S)-E" with a reducing agent to provide (R)-MBDB.

The present application also includes a compound of Formula (S)-C:

(S)-C

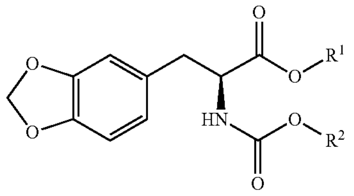

wherein $R^1$ is $C_{1-4}$alkyl; and $R^2$ is $CH_3$ or $CH_2CH_3$.

The present application includes a compound of Formula (R)-C:

(R)-C

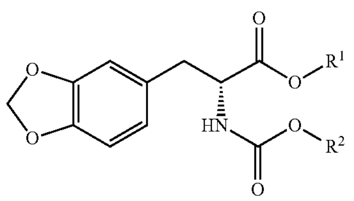

wherein $R^1$ is $C_{1-4}$alkyl; and $R^2$ is $CH_3$ or $CH_2CH_3$.

The present application also includes a compound of Formula (S)-C'

(S)-C′

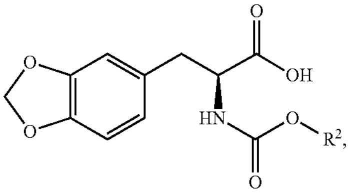

wherein $R^2$ is $CH_3$

The present application also includes a compound of Formula (R)-C':

(R)-C′

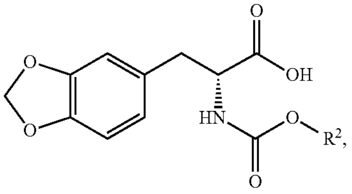

wherein $R^2$ is $CH_3$.

The present application also includes a compound of Formula (S)-D (S)-D

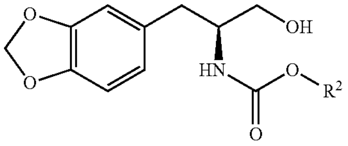

wherein $R^2$ is $CH_3$, $CH_2CH_3$ or $CH_2Ph$.

The present application further includes a compound of Formula (R)-D:

(R)-D

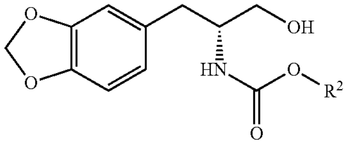

wherein $R^2$ is $CH_3$, $CH_2CH_3$ or $CH_2Ph$.

The present application also includes a compound of Formula (S)-D';

(S)-D′

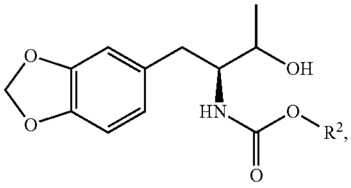

wherein $R^2$ is $CH_3$

The present application also includes a compound of Formula (R)-D';

(R)-D′

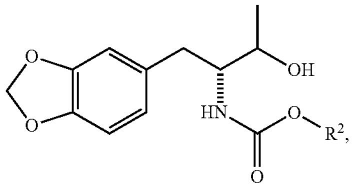

wherein $R^2$ is $CH_3$, $CH_2CH_3$ or $C(CH_3)$

The present application also includes a compound of Formula (S)-$D^{ox}$;

(S)-$D^{ox}$

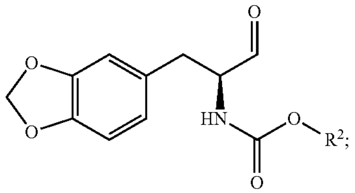

wherein $R^2$ is $CH_3$

The present application also includes a compound of Formula (R)-$D^{ox}$;

(R)-$D^{ox}$

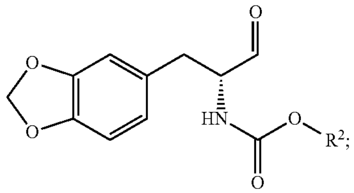

wherein $R^2$ is $CH_3$

The present application also includes a compound of Formula (S)-E:

(S)-E

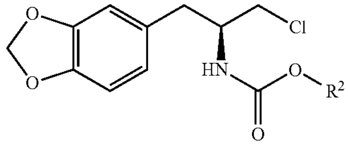

wherein $R^2$ is $CH_3$, $CH_2CH_3$ or $CH_2Ph$.

The present application also includes a compound of Formula (R)-E (R)-E

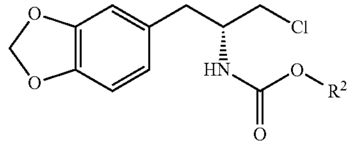

wherein $R^2$ is $CH_3$, $CH_2CH_3$ or $CH_2Ph$.

The present application also includes a compound of Formula (S)-E (S)-E′

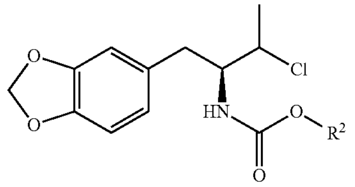

wherein $R^2$ is $CH_3$.

The present application also includes a compound of Formula (R)-E'

(R)-E′

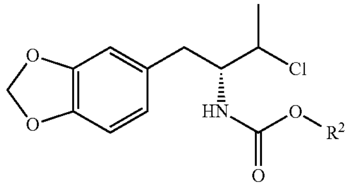

wherein $R^2$ is $CH_3$.

The present application also includes a compound of Formula (S)-E"

(S)-E″

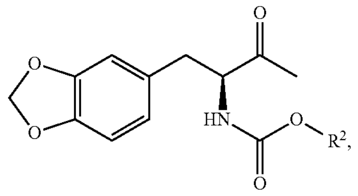

wherein $R^2$ is $CH_3$.

The present application also includes a compound of Formula (R)-E"

(R)-E″

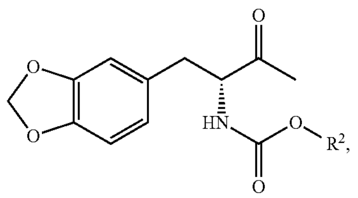

wherein $R^2$ is $CH_3$.

The present application also includes a compound of Formula the amide compound of Formula (S)-E""

(S)-E‴

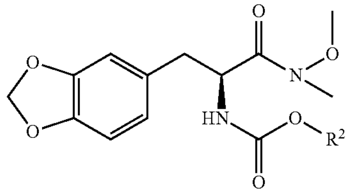

wherein $R^2$ is $CH_3$.

The present application also includes a compound of Formula (R)-E"

(R)-E‴

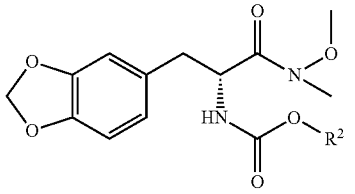

wherein R is $CH_3$ or $CH_2CH_3$; and (S)-F

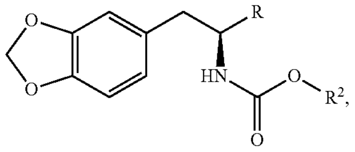

$R^2$ is $CH_3$ or $CH_2Ph$.

The present application also includes a compound of Formula (R)-F:

(R)-F

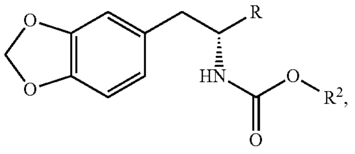

wherein R is $CH_3$ or $CH_2CH_3$; and $R^2$ is $CH_3$ or $CH_2Ph$.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "process of the application" and the like as used herein refers to a process of preparing (R)- or (S)-MDMA or (R)- or (S)-MBDB or acid salts thereof as described herein.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a solvate of a salt of a compound of the application.

As used in the present application, the singular forms "a", "an" and "the" include plural references unless the content clearly dictates otherwise. For example, an embodiment including "a solvent" should be understood to present certain aspects with one solvent, or two or more additional solvents.

In embodiments comprising an "additional" or "second" component, such as an additional or second solvent, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions to provide the product shown. A person skilled in the art would understand that, unless otherwise indicated, all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word.

The present description refers to a number of chemical terms and abbreviations used by those skilled in the art. Nevertheless, definitions of selected terms are provided for clarity and consistency.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5 or 6 carbon atoms.

The term "available", as in "available hydrogen atoms" or "available atoms" refers to atoms that would be known to a person skilled in the art to be capable of replacement by a substituent.

The term "MDMA" as used herein refers to a compound having the chemical name: 1-(1,3-benzodioxol-5-yl)-N-methylpropan-2-amine, or 3,4-methylenedioxymethamphetamine, and having the chemical formula:

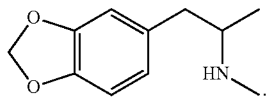

The term "R-MDMA" as used herein refers to a compound having the chemical name: (2R)-1-(1,3-benzodioxol-5-yl)-N-methylpropan-2-amine, or (R)-3,4-methylenedioxymethamphetamine, and having the chemical formula:

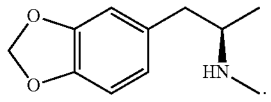

The term "(S)-MDMA" as used herein refers to a compound having the chemical name: (2S)-1-(1,3-benzodioxol-5-yl)-N-methylpropan-2-amine, or (S)-3,4-methylenedioxymethamphetamine, and having the chemical formula:

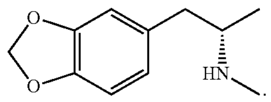

The term "MBDB" as used herein refers to a compound having the chemical name: (R)-1-(1,3-benzodioxol-5-yl)-N-methylbutan-2-amine, or N-methyl-1,3-benzodioxolylbutanamine, and having the chemical formula:

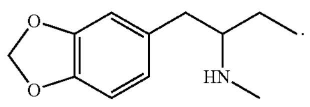

The term "R-MBDB" as used herein refers to a compound having the chemical name: (2R)-1-(1,3-benzodioxol-5-yl)-N-methylbutan-2-amine, or (R)—N-methyl-1,3-benzodioxolylbutanamine, and having the chemical formula:

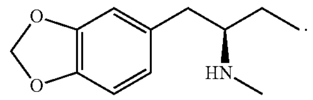

The term "(S)-MBDB" as used herein refers to a compound having the chemical name: (2S)-1-(1,3-benzodioxol-5-yl)-N-methylbutan-2-amine or (S)—N-methyl-1,3-benzodioxolylbutanamine, and having the chemical formula:

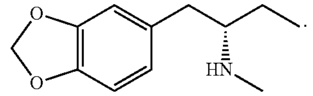

The term "L-DOPA" as used herein refers to a compound having the chemical name: 3,4-dihydroxy-L-phenylalanine, and having the chemical formula:

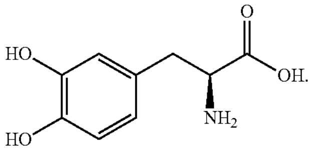 [SMILES: N[C@@H](Cc1ccc(O)c(O)c1)C(=O)O]

The term "D-DOPA" as used herein refers to a compound having the chemical name: 3,4-dihydroxy-D-phenylalanine, and having the chemical formula:

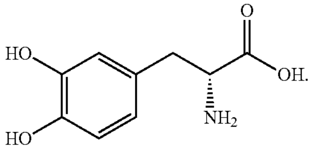 [SMILES: N[C@H](Cc1ccc(O)c(O)c1)C(=O)O]

The term "reducing agent" as used herein means any compound or combination of compounds that reduces a desired functional group. A reducing agent results in the overall addition of electrons, or in the case of organic chemistry, hydrogen atoms to the functional group.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art.

The term "solvent" includes both a single solvent and a mixture comprising two or more solvents.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas).

The term "major isomer" as used herein refers to a stereochemical isomer, including a regional isomer, that is the most abundant isomer in a mixture of isomers of the same compound. Conversely, the term "minor isomer" as used herein refers to a stereochemical isomer, including a regional isomer, that is not the most abundant isomer in a mixture of isomers of the same compound.

The term "enantiomeric excess" or "ee" is the absolute difference between the mole fraction of each enantiomer for a racemic compound.

In the processes of the application, when compounds, including starting materials and products, are referred to as single isomers, e.g. R- or S-isomers, this means that the single isomer comprises less than 20%, 15%, 10%, 5%, 4%, 3%, 2% or 1% by weight of the alternate isomer based on the total amount of R- and S-isomers.

The products of the processes of the application may be isolated according to known methods, for example, the compounds may be isolated by evaporation of the solvent, by filtration, centrifugation, chromatography or other suitable method.

II. Processes of the Application

The present application includes a method of preparing the (R)- or (S)-3,4-methylenedioxymethamphetamine, ((R)-MDMA or (S)-MDMA) and (R)- or (S)—N-methyl-1,3-benzodioxolylbutanamine ((R)-MBDB or (S)-MBDB)) using 3,4-dihydroxy-L-phenylalanine (L-DOPA) methyl ester or 3,4-dihydroxy-D-phenylalanine (D-DOPA) methyl ester, respectively. In an embodiment, (R)-MDMA or (S)-MDMA is prepared in, a five-step synthetic protocol. In an embodiment, (R)-MBDB or (S)-MBDB is prepared in, a five-step synthetic protocol or in a seven-step synthetic protocol.

Accordingly, the present application includes a process for preparing a compound of Formula (R)-I or (S)-I:

(R)-I

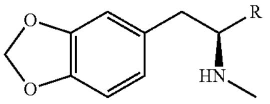

or (S)-I

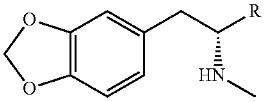

wherein

R is selected from $CH_3$ and $CH_2CH_3$;

the process comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

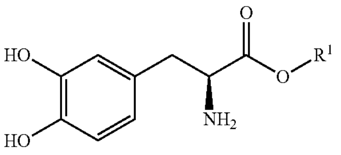

or

-continued (R)-A

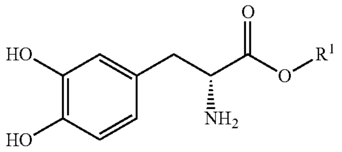

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

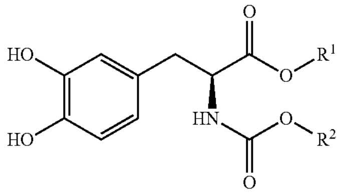

or (R)-B

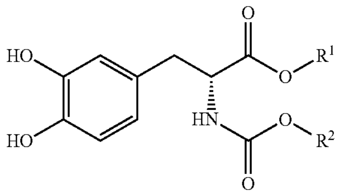

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

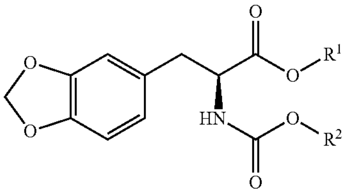

or (R)-C

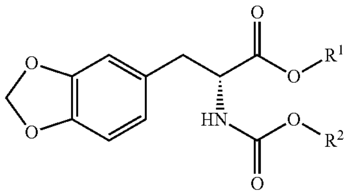

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

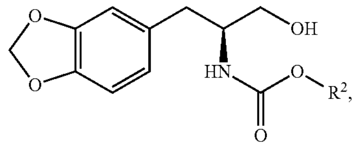

, or (R)-D

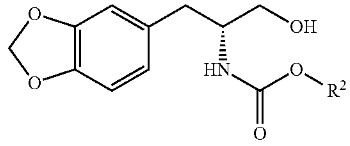

wherein $R^2$ is $C_{1-4}$alkyl or $CH_2Ph$;

when R is $CH_2CH_3$, further oxidizing the compound of Formula (S)-D or (R)-D to provide a compound of Formula (S)-$D^{ox}$ or (R)-$D^{ox}$, respectively; and (S)-$D^{ox}$

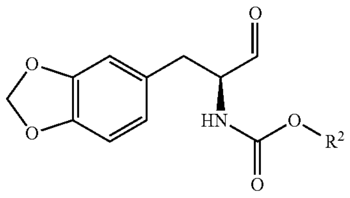

or (R)-$D^{ox}$

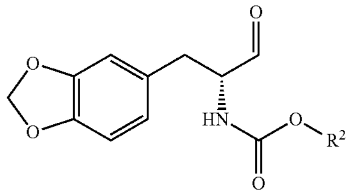

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

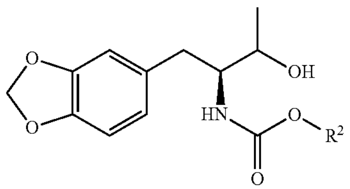

or (R)-D'

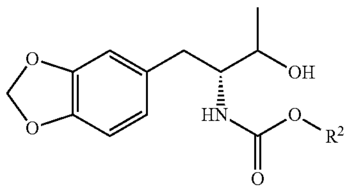

wherein $R^2$ is $C_{1-4}$alkyl or $CH_2Ph$; and reacting the compound of Formula (S)-D or (R)-D with a chlorinating agent to provide a compound of Formula (S)-E or (R)-E, respectively, or reacting the compound Formula of (S)-D' or (R)-D' with a chlorinating agent to provide a compound of Formula (S)-E or (R)-E', respectively:

(S)-E

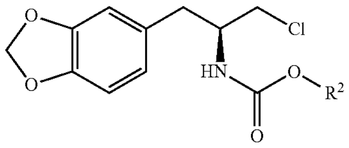

or (R)-E

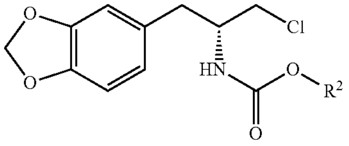

or (S)-E′

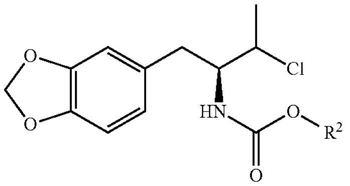

or (R)-E′

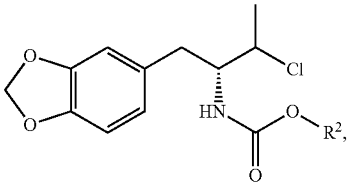

, wherein $R^2$ is $C_{1-4}$alkyl or $CH_2Ph$; or when R is $CH_2CH_3$, hydrolyzing the compound of Formula (S)-C or (R)-C to provide the compound of Formula (S)-C' or (R)-C', respectively;

(S)-C′

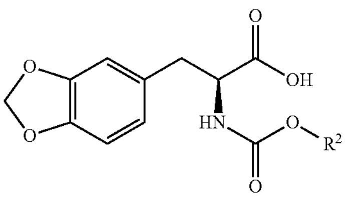

or (R)-C′

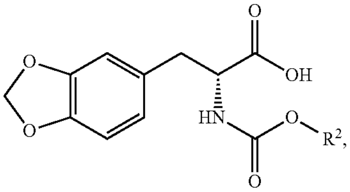

, wherein $R^2$ is $C_{1-4}$alkyl or $CH_2Ph$; and converting the compound of Formula (S)-C' or (R)-C' to the compound of Formula (S)-E" or (R)-E", respectively (S)-E″

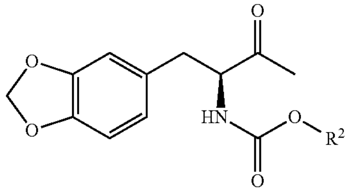

or (R)-E″

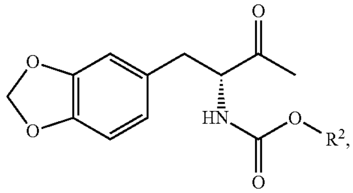

, wherein $R^2$ is $C_{1-4}$alkyl or $CH_2Ph$; and reacting the compound of Formula (S)-E or (R)-E with a reducing agent to provide the compound of Formula (R)-I or (S)-I, respectively, wherein R is $CH_3$, reacting the compound of Formula (S)-E' or (R)-E' with a reducing agent to provide the compound of Formula (R)-I or (S)-I, respectively, wherein R is $CH_2CH_3$, or reacting the compound of Formula (S)-E" or (R)-E" with a reducing agent to provide the compound of Formula (R)-I or (S)-I, respectively, wherein R is $CH_2CH_3$.

Therefore, the present application includes a process for preparing a compound of Formula (R)-I:

(R)-I

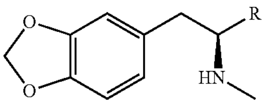

wherein R is selected from $CH_3$ and $CH_2CH_3$;

the process comprising:

protecting the amino group of 3,4-dihydroxy-L-phenylalanine (L-DOPA) $C_{1-4}$alkyl ester of Formula (S)-A:

(S)-A

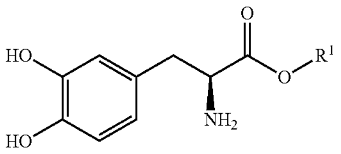

wherein $R^1$ is $C_{1-4}$alkyl, with a $C_{1-4}$alkoxycarbonyl protecting group or a benzyloxy carbonyl protecting group to provide a compound of Formula (S)-B:

(S)-B

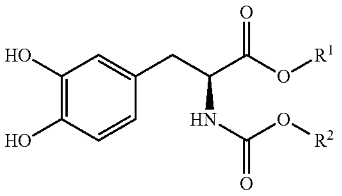

wherein $R^1$ is $C_{1-4}$alkyl, and $R^2$ is $C_{1-4}$alkyl or $CH_2Ph$;

cyclizing the compound of Formula (S)-B to provide a compound of Formula (S)-C:

(S)-C

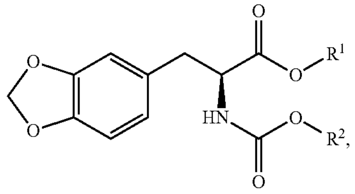

wherein $R^1$ is $C_{1-4}$alkyl, and $R^2$ is $C_{1-4}$alkyl or $CH_2Ph$;

reacting the compound of Formula (S)-C with a reducing agent to provide a compound of Formula (S)-D:

(S)-D

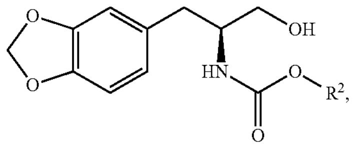

wherein $R^2$ is $C_{1-4}$alkyl or $CH_2Ph$;

when R is $CH_2CH_3$, further oxidizing the compound of Formula (S)-D to provide a compound of Formula (S)-$D^{ox}$; and (S)-$D^{ox}$

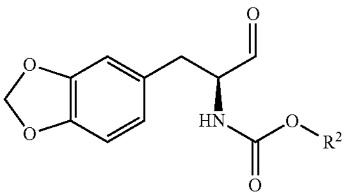

wherein $R^2$ is $C_{1-4}$alkyl or $CH_2Ph$;

reacting the compound of Formula (S)-$D^{ox}$ with a methyl organometallic reagent to provide the compound of Formula (S)-D';

(S)-D'

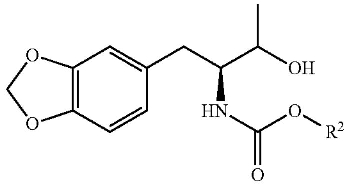

wherein $R^2$ is $C_{1-4}$alkyl or $CH_2Ph$; and reacting the compound of Formula (S)-D with a chlorinating agent to provide a compound of Formula (S)-E, or reacting the compound of Formula (S)-D' with a chlorinating agent to provide a compound Formula (S)-E':

(S)-E

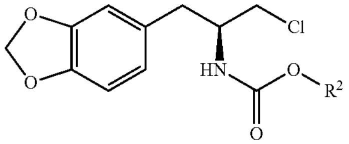

or (S)-E'

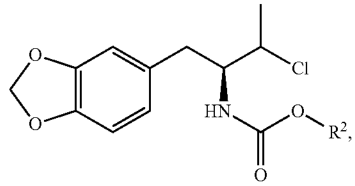

wherein $R^2$ is $C_{1-4}$alkyl or $CH_2Ph$; or when R is $CH_2CH_3$, hydrolyzing the compound of Formula (S)-C to provide the compound of Formula (S)-C';

(S)-C'

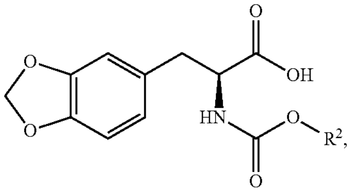

wherein $R^2$ is $C_{1-4}$alkyl or $CH_2Ph$; and converting the compound of Formula (S)-C' to the compound of Formula (S)-E"

(S)-E"

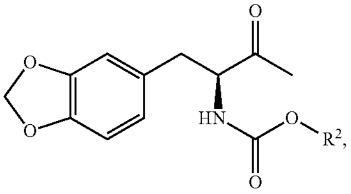

wherein $R^2$ is $C_{1-4}$alkyl or $CH_2Ph$; and reacting the compound of Formula (S)-E with a reducing agent to provide the compound of Formula (R)-I, wherein R is $CH_3$, reacting the compound of Formula (S)-E' with a reducing agent to provide the compound of Formula (R)-I, wherein R is $CH_2CH_3$, or reacting the compound of Formula (S)-E" with a reducing agent to provide the compound of Formula (R)-I, wherein R is $CH_2CH_3$.

The present application also includes a process for preparing a compound of Formula (S)-I:

(S)-I

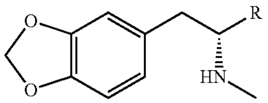

wherein R is selected from $CH_3$ and $CH_2CH_3$;

the process comprising:

protecting the amino group of 3,4-dihydroxy-D-phenylalanine (D-DOPA) $C_{1-4}$alkyl ester of Formula (S)-A:

(R)-A

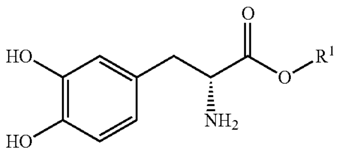

wherein $R^1$ is $C_{1-4}$alkyl, with a $C_{1-4}$alkoxycarbonyl protecting group or a benzyloxy carbonyl protecting group to provide a compound of Formula (R)-B:

(R)-B

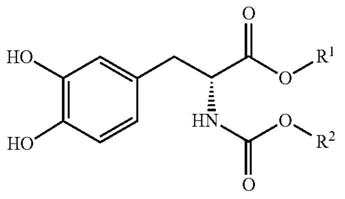

wherein $R^1$ is $C_{1-4}$alkyl, and $R^2$ is $C_{1-4}$alkyl or $CH_2Ph$;

cyclizing the compound of Formula (R)-B to provide a compound of Formula (R)-C:

(R)-C

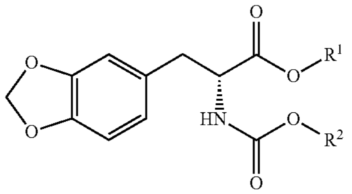

wherein $R^1$ is $C_{1-4}$alkyl, and $R^2$ is $C_{1-4}$alkyl or $CH_2Ph$;

reacting the compound of Formula (R)-C with a reducing agent to provide a compound of Formula (R)-D:

(R)-D

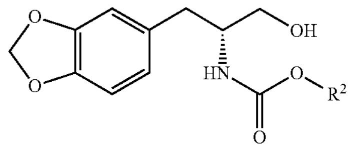

wherein $R^2$ is $C_{1-4}$alkyl or $CH_2Ph$;

when R is $CH_2CH_3$, further oxidizing the compound of Formula (R)-D to provide a compound of Formula (R)-$D^{ox}$, respectively; and (R)-$D^{ox}$

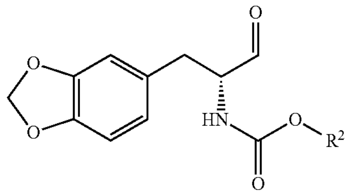

wherein $R^2$ is $C_{1-4}$alkyl or $CH_2Ph$;

reacting the compound of Formula (R)-$D^{ox}$ with a methyl organometallic reagent to provide the compound of Formula (R)-D', respectively;

(R)-D'

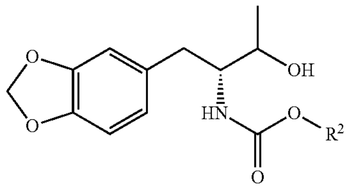

wherein $R^2$ is $C_{1-4}$alkyl or $CH_2Ph$; and reacting the compound of Formula (R)-D with a chlorinating agent to provide a compound of Formula (R)-E, or reacting the compound of Formula (R)-D' with a chlorinating agent to provide a compound of Formula (R)-E':

(R)-E

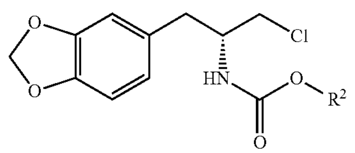

or (R)-E'

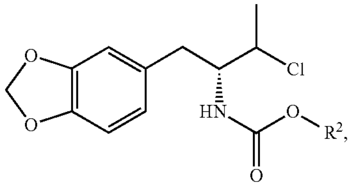

wherein $R^2$ is $C_{1-4}$alkyl or $CH_2Ph$; or when R is $CH_2CH_3$, hydrolyzing the compound of Formula (R)-C to provide the compound of Formula (R)-C';

(R)-C'

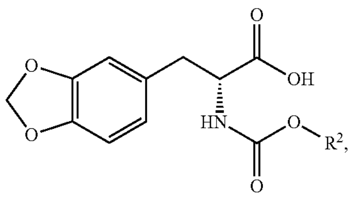

wherein $R^2$ is $C_{1-4}$alkyl or $CH_2Ph$; and converting the compound of Formula (R)-C' to the compound of Formula (R)-E"

(R)-E"

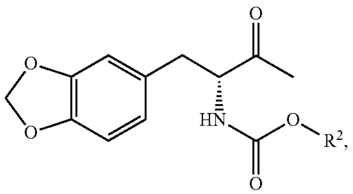

wherein $R^2$ is $C_{1-4}$alkyl or $CH_2Ph$; and reacting the compound of Formula (R)-E with a reducing agent to provide the compound of Formula (S)-I, wherein R is $CH_3$, reacting the compound of Formula (R)-E' with a reducing agent to provide the compound of Formula (S)-I, wherein R is $CH_2CH_3$, or reacting the compound of Formula (R)-E" with a reducing agent to provide the compound of Formula (S)-I, wherein R is $CH_2CH_3$ In some embodiments, when R is $CH_3$, the compound of Formula (R)-I is (R)-3,4-methylenedioxymethamphetamine ((R)-MDMA). In some embodiments, when R is $CH_3$, the compound of Formula (S)-I is (S)-3,4-methylenedioxymethamphetamine ((S)-MDMA). Accordingly, in some embodiments, the present application also includes a process for preparing (R)-3,4-methylenedioxymethamphetamine ((R)-MDMA) or preparing (S)-3,4-methylenedioxymethamphetamine ((S)-MDMA):

(R)-MDMA)

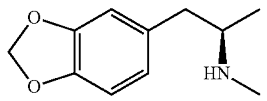

or (S)-MDMA

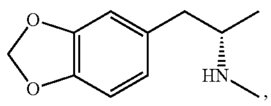

the process comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

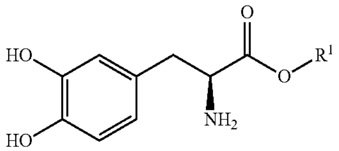

or (R)-A

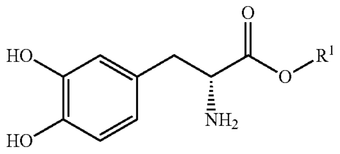

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

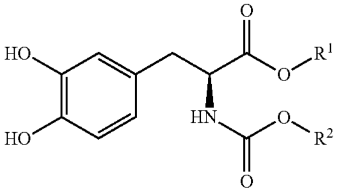

or (R)-B

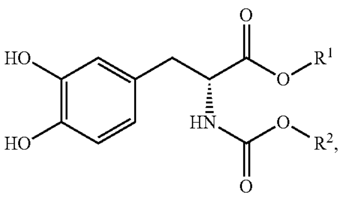

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C respectively:

(S)-C

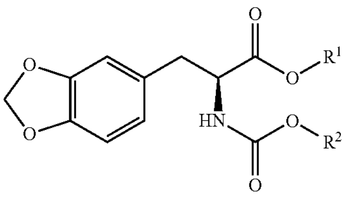

or (R)-C

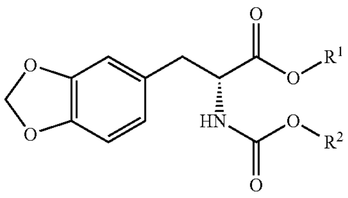

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

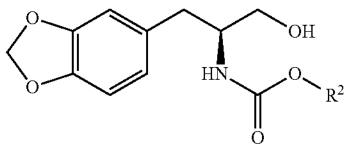

or (R)-D

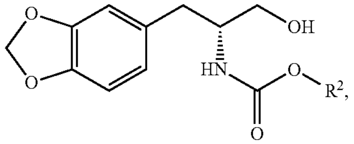

wherein $R^2$ is $C_{1-4}$alkyl or $CH_2Ph$;

reacting the compound of Formula (S)-D or (R)-D with a chlorinating agent to provide a compound of Formula (S)-E or (R)-E, respectively:

(S)-E

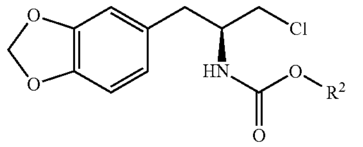

or (R)-E

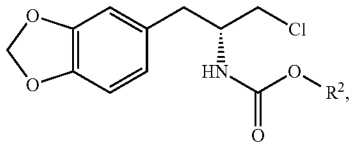

wherein $R^2$ is $C_{1-4}$alkyl or $CH_2Ph$; and reacting the compound of Formula (S)-E or (R)-E with a reducing agent to provide (R)-MDMA or (S)-MDMA, respectively.

In some embodiments, when R is $CH_2CH_3$, the compound of Formula (R)-I is (R)—N-methyl-1,3-benzodioxolylbutanamine ((R)-MBDB). In some embodiments, when R is $CH_2CH_3$, the compound of Formula (R)-I is (R)—N-methyl-1,3-benzodioxolylbutanamine ((R)-MBDB). Accordingly, the present application includes a process for preparing (R)—N-methyl-1,3-benzodioxolylbutanamine ((R)-MBDB) or (S)—N-methyl-1,3-benzodioxolylbutanamine ((S)-MBDB):

(R)-MBDB

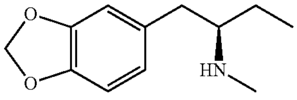

or (S)-MBDB

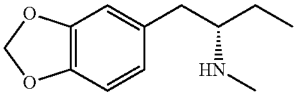

the process comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

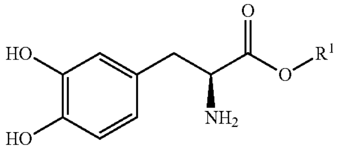

or (R)-A

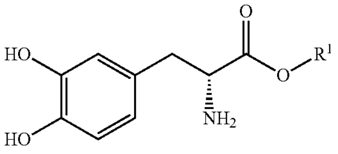

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

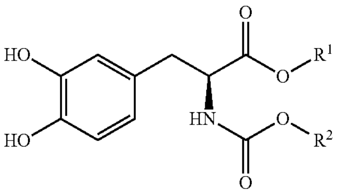

or (R)-B

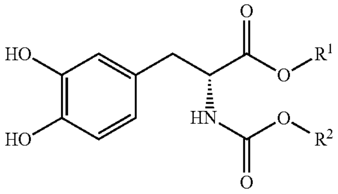

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

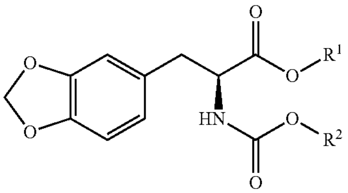

or (R)-C

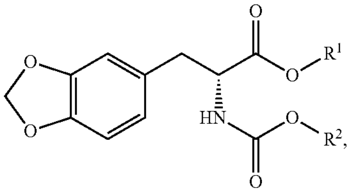

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

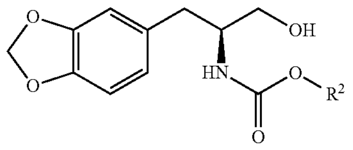

or (R)-D

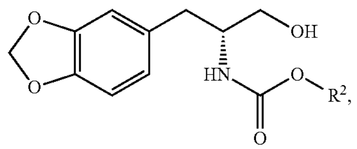

wherein $R^2$ is $C_{1-4}$alkyl or $CH_2Ph$;

oxidizing the compound of Formula (S)-D or (R)-D to provide a compound of Formula (S)-$D^{ox}$ or (R)-$D^{ox}$, respectively;

(S)-$D^{ox}$

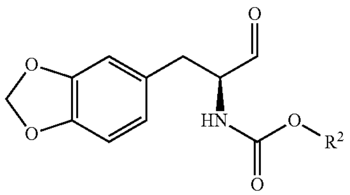

or (R)-$D^{ox}$

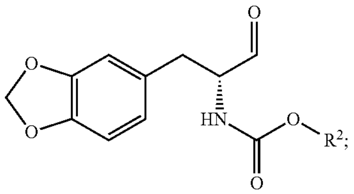

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

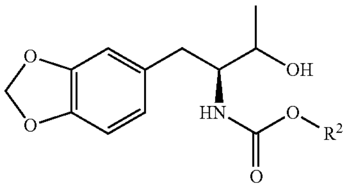

or

-continued (R)-D'

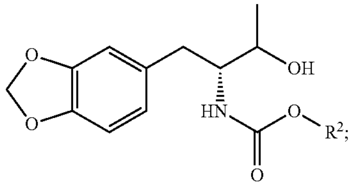

wherein $R^2$ is $C_{1-4}$alkyl or $CH_2Ph$;

reacting the compound of Formula (S)-D' or (R)-D' with a chlorinating agent to provide a compound of Formula (S)-E' or (R)-E', respectively:

(S)-E'

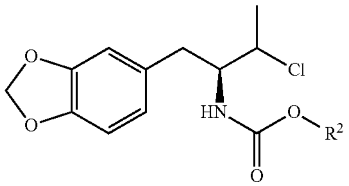

or (R)-E'

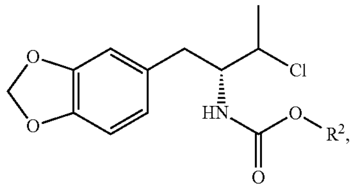

wherein $R^2$ is $C_{1-4}$alkyl or $CH_2Ph$; and reacting the compound of Formula (S)-E' or (R)-E' with a reducing agent to provide (R)-MBDB or (S)-MBDB, respectively.

The present application also includes a process for preparing (R)—N-methyl-1,3-benzodioxolylbutanamine ((R)-MBDB)

(R)-MBDB

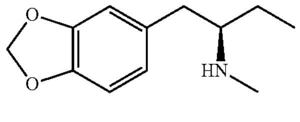

the process comprising:

protecting the amino group of 3,4-dihydroxy-L-phenylalanine (L-DOPA) $C_{1-4}$alkyl ester of Formula (S)-A:

(S)-A

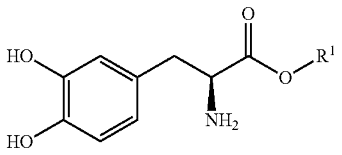

wherein $R^1$ is $C_{1-4}$alkyl, with a $C_{1-4}$alkoxycarbonyl protecting group or a benzyloxy carbonyl protecting group to provide a compound of Formula (S)-B:

(S)-B

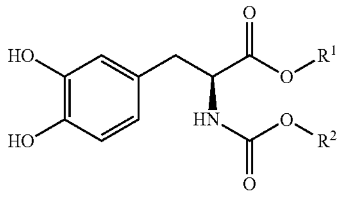

wherein $R^1$ is $C_{1-4}$alkyl, and $R^2$ is $C_{1-4}$alkyl or $CH_2Ph$;

cyclizing the compound of Formula (S)-B to provide a compound of Formula (S)-C:

(S)-C

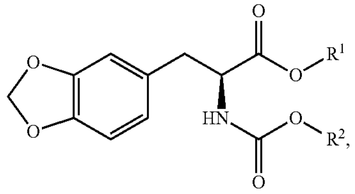

wherein $R^1$ is $C_{1-4}$alkyl, and $R^2$ is $C_{1-4}$alkyl or $CH_2Ph$;

hydrolyzing the compound of Formula (S)-C to provide the compound of Formula (S)-C';

(S)-C'

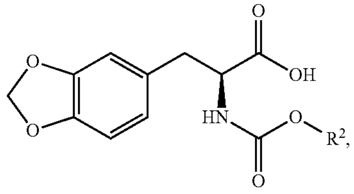

wherein $R^2$ is $C_{1-4}$alkyl or $CH_2Ph$;

converting the compound of Formula (S)-C' to the compound of Formula (S)-E"

(S)-E"

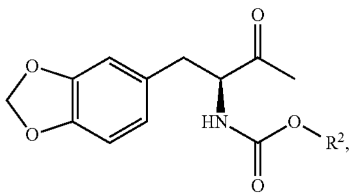

wherein $R^2$ is $C_{1-4}$alkyl or $CH_2Ph$; and reacting the compound of Formula (S)-E" with a reducing agent to provide (R)-MBDB.

The present application also includes a process for preparing (S)—N-methyl-1,3-benzodioxolylbutanamine ((S)-MBDB)

(S)-MBDB

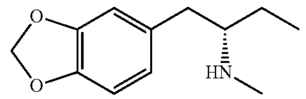

the process comprising:

protecting the amino group of 3,4-dihydroxy-D-phenylalanine (D-DOPA) $C_{1-4}$alkyl ester of Formula (R)-A:

(R)-A

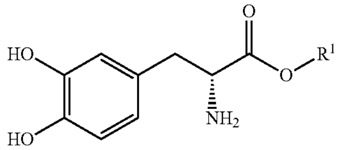

wherein $R^1$ is $C_{1-4}$alkyl, with a $C_{1-4}$alkoxycarbonyl protecting group or a benzyloxy carbonyl protecting group to provide a compound of Formula (R)-B:

(R)-B

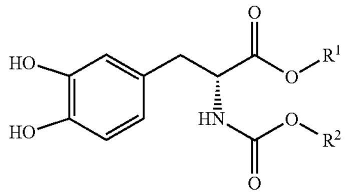

wherein $R^1$ is $C_{1-4}$alkyl, and $R^2$ is $C_{1-4}$alkyl or $CH_2Ph$;

cyclizing the compound of Formula (R)-B to provide a compound of Formula (R)-C:

(R)-C

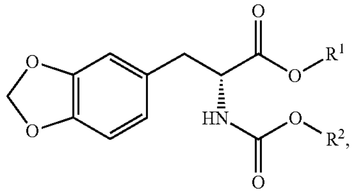

wherein $R^1$ is $C_{1-4}$alkyl, and $R^2$ is $C_{1-4}$alkyl or $CH_2Ph$;

hydrolyzing the compound of Formula (R)-C to provide the compound of Formula (R)-C';

(R)-C'

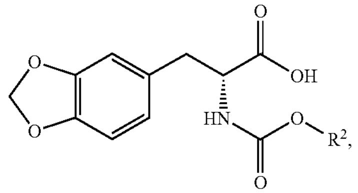

wherein $R^2$ is $C_{1-4}$alkyl or $CH_2Ph$;

converting the compound of Formula (R)-C' to the compound of Formula (R)-E"

(R)-E"

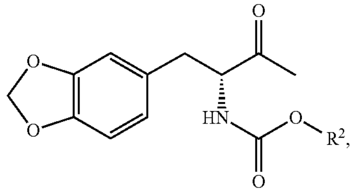

wherein $R^2$ is $C_{1-4}$alkyl or $CH_2Ph$; and reacting the compound of Formula (R)-E" with a reducing agent to provide (S)-MBDB.

In some embodiments, the compound of Formula (S)-A has an enantiomeric purity of about 98% or greater. In some embodiments, the compound of Formula (S)-A has an enantiomeric purity of about 98% to about 99.9%, about 98% to about 99.8%, about 98% to about 99.5%, about 97% to about 99%, or about 98% to about 99%. In some embodiments, the compound of Formula (S)-A that has an enantiomeric purity of about 98% or greater is either commercially available or may be prepared using methods known in the art. For example, L-DOPA methyl or ethyl ester with a purity of about 98% or greater is available from Sigma Aldrich (St. Louis, Missouri, USA).

In some embodiments, the compound of Formula (S)-A or (R)-A is prepared by reacting L-DOPA, for example L-DOPA having an enantiomeric purity of about 98% or greater, or D-DOPA, for example D-DOPA having an enantiomeric purity of about 95% or greater, respectively with an excess amount (for example 1.1 to about 2 molar equivalents) of a chlorinating reagent in a $C_{1-4}$alkanol, such as dry methanol or dry ethanol. In some embodiments, the suitable chlorinating reagent is selected from thionyl chloride ($SOCl_2$), phosphorus trichloride ($PCl_3$), phosphorus pentachloride ($PCl_5$) or oxalyl chloride [$(COCl)_2$]. In some embodiments, the suitable chlorinating reagent is $SOCl_2$.

In some embodiments, the compound of Formula (S)-A or (R)-A is prepared by reacting L-DOPA, for example L-DOPA having an enantiomeric purity of about 98% or greater, or D-DOPA, for example D-DOPA having an enantiomeric purity of about 95% or greater, respectively with an excess amount (for example 1.1 to about 2 molar equivalents) of a chlorinating reagent in a $C_{1-4}$alkanol at about 0° C. and then increasing the temperature to the boiling point (reflux). As representative, non-limiting example of reaction times, the reaction is maintained at the boiling point for about 15 minutes to about 24 hours, about 1 hour to about 24 hours, about 4 hours to about 24 hours, about 6 hours to about 24 hours, about 12 hours to about 24 hours, or about 24 hours.

In some embodiments, the compound of Formula (S)-A or (R)-A is prepared by combining L-DOPA or D-DOPA respectively and a $C_{1-4}$alkanol in the presence of a suitable acid catalyst. In some embodiments, the suitable acid catalyst is sulfuric acid.

In some embodiments, the compound of Formula (S)-A or (R)-A is prepared using the synthetic procedures described in European Journal of Organic Chemistry, 2020(46), 7144-7150, 2020 or Organic & Biomolecular Chemistry, 18(14), 2702-2715, 2020.

In some embodiments, the compound of Formula (S)-A or (R)-A is the methyl or ethyl ester of L-DOPA or D-DOPA, respectively. In some embodiments, the compound of Formula (S)-A or (R)-A is the methyl ester of L-DOPA or D-DOPA respectively.

In some embodiments L-DOPA, for example L-DOPA having an enantiomeric purity of about 98% or greater, is available from, Asta Tech (Bristol, Pennsylvania, USA), Sigma Aldrich (St. Louis, Missouri, USA) or Combi-Blocks (San Diego, California, USA).

In some embodiments, the $C_{1-4}$alkoxycarbonyl protecting group is methoxycarbonyl or ethoxycarbonyl.

In some embodiments D-DOPA, for example D-DOPA having an enantiomeric purity of about 95% or greater, is available from Sigma Aldrich (St. Louis, Missouri, USA).

In some embodiments, L-DOPA has an enantiomeric purity of about 98% to about 99.9%, about 98% to about 99.8%, about 98% to about 99.5%, or about 98% to about 99%. In some embodiments, D-DOPA has an enantiomeric purity of about 95% to about 99.9%, about 95% to about 99.8%, about 95% to about 99.5%, about 95% to about 99%, about 95% to about 98%, about 95% to about 97%, about 95% to about 96%, about 96% to about 99.9%, about 97% to about 99.9%, about 98% to about 99.9% or about 99% to about 99.9%.

In some embodiments, the compound of Formula (S)-B or (R)-B is prepared by reacting the compound of Formula (S)-A or (R)-A with a slight excess (for example about 1.1 to about 1.5 molar equivalents) of an appropriate $C_{1-4}$alkyl chloroformate or benzyl chloroformate in a suitable solvent in the presence of a base. In an embodiment, the $C_{1-4}$alkyl chloroformate is selected from methyl chloroformate and ethyl chloroformate. In an embodiment, the $C_{1-4}$alkyl chloroformate is methyl chloroformate. In some embodiments, the base is an inorganic base, such as sodium bicarbonate.

In some embodiments, the compound of Formula (S)-B or (R)-B is prepared by reacting the compound of Formula (S)-A or (R)-A with the $C_{1-4}$alkyl chloroformate or benzyl chloroformate under aqueous conditions in the presence of an inorganic base to provide the compound of Formula (S)-B or (R)-B, respectively. In some embodiments, the inorganic base is selected from a bicarbonate and a hydroxide base. In some embodiments, the base is selected from sodium bicarbonate, potassium bicarbonate, ammonium bicarbonate, potassium hydroxide and sodium hydroxide. In some embodiments, the inorganic base is sodium bicarbonate or potassium bicarbonate. In some embodiments, the reacting of the compound of Formula (S)-A or (R)-A with the $C_{1-4}$alkyl chloroformate or benzyl chloroformate further comprise the use of an inert organic solvent. In some embodiments, the inert organic solvent is tetrahydrofuran (THF).

In some embodiments, the compound of Formula (S)-B or (R)-B is prepared by reacting the compound of Formula (S)-A or (R)-A with the $C_{1-4}$alkyl chloroformate or benzyl chloroformate for example, using the synthetic procedures found in Organic & Biomolecular Chemistry, 18(14), 2702-2715, 2020.

As representative, non-limiting examples, the temperature and times for reacting the compound of Formula (S)-A or (R)-A with the $C_{1-4}$alkyl chloroformate such as methyl chloroformate or benzyl chloroformate to provide the compound of Formula (S)-B or (R)-B, respectively is about 0° C. to about 25° C., about 18° C. to about 25° C. or about 20° C. to about 25° C. or room temperature for about 12 hours to about 30 hours, about 16 hours to about 30 hours, about 20 hours to about 26 hours or about 24 hours.

In some embodiments, the compound of Formula (S)-C or (R)-C is prepared using any suitable conditions for cyclizing the compound of Formula (S)-B or (R)-B to provide the compound of Formula (S)-C or (R)-C, respectively, known in the art, for example, using the synthetic procedures found in WO2012/174699.

In some embodiments, the conditions for cyclizing the compound of Formula (S)-B or (R)-B to provide the compound of Formula (S)-C or (R)-C, respectively, comprise combining the compound of Formula (S)-B or (R)-B with an excess amount (for example, about 3 to about 5, or about 3 to about 4 molar equivalent) of a carbonate salt and an excess (for example, about 1.1 to about 3, about 1.1 to about 2.5 or about 2 to about 2.5 molar equivalent) dihalomethane at temperatures for the reaction of the compound of Formula (S)-B or (R)-B with carbonate salt and dihalomethane to provide the compound of Formula (S)-C and (R)-C, respectively. In some embodiments, the carbonate salt is sodium carbonate, potassium carbonate or cesium carbonate. In some embodiments, the dihalomethane is selected from bromochloromethane, bromoiodomethane and diiodomethane. In some embodiments, the conditions for cyclizing the compound of Formula (S)-B or (R)-B to provide the compound of Formula (S)-C or (R)-C, respectively comprise combining the compound of Formula (S)-B or (R)-B with an excess amount (for example, about 3 to about 5, or about 3 to about 4 molar equivalent) of potassium carbonate and an excess (for example, about 2 to about 2.5 molar equivalent) of diiodomethane to provide the compound of Formula (S)-C or (R)-C respectively. In some embodiments, the conditions for cyclizing the compound of Formula (S)-B or (R)-B comprise an inert solvent. In an embodiment, the inert solvent is acetone.

In some embodiments, the temperature for the reaction of the compound of Formula (S)-B or (R)-B with a carbonate salt and dihalomethane to provide the compound of Formula (S)-C or (R)-C is at the boiling point of the solvent (reflux). As representative, non-limiting example of reaction times, the reaction is maintained at boiling point of the solvent (reflux) for about 1 hour to about 12 hours, about 3 hours to about 12 hours, about 6 hours to about 24 hours, about 10 hours to about 20 hours, about 12 hours to about 18 hours or about 16 hours.

In some embodiments, the reducing agent for reacting with the compound of Formula (S)-C or (R)-C to provide the compound of Formula (S)-D or (R)-D respectively is a metal hydride. In some embodiments, the metal hydride is selected from lithium borohydride, sodium borohydride, potassium borohydride, sodium cyano borohydride, tributyltin hydride and lithium aluminum hydride. The Applicants have found that yields of compounds of Formula (S)-D or (R)-D were improved when using lithium aluminum hydride as the reducing agent compared to sodium borohydride or potassium borohydride under otherwise comparable conditions. Therefore, in an exemplary embodiment, the metal hydride is lithium aluminum hydride.

In some embodiments, the conditions for providing the compound of formula (S)-D or (R)-D are any suitable conditions for reducing the compound of Formula (S)-C or (R)-C with a reducing agent to provide a compound of Formula (S)-D or (R)-D, respectively known in the art, for example, using the synthetic procedures found in J. Med. Chem. 1992, 35 (16), 3081-3084.

In some embodiments, the compound of Formula (S)-C or (R)-C is reacted with the reducing agent (for example about 0.5 to about 1.5 or about 1.1 to about 1.5 or about 1.1 molar equivalents of the reducing agent) in a suitable inert solvent. In some embodiments, the compound of Formula (S)-C or (R)-C is added to a solution of the reducing agent in the suitable inert solvent at temperatures of about 0° C. to about 15° C., about 5° C. to about 15° C., or about 8° C. to about 10° C. for over about 10 minutes to about 1 hour, about 15 minutes to about 45 minutes, about 15 minutes to about 30 minutes or about 20 minutes to form a reaction mixture, and then the reaction mixture is allowed to warm to about 15° C. to about 30° C., about 20° C. to about 25° C., or about 25° C. or about room temperature over about 1 hour to about 5 hours, about 1 hours to about 3 hours, or about 1 hours under an inert atmosphere, to provide a compound of Formula (S)-D or (R)-D respectively. In some embodiments, the inert atmosphere is argon or nitrogen. In some embodiments, the inert atmosphere is argon.

In some embodiments, the conditions for providing the compound of formula (S)-$D^{ox}$ or (R)-$D^{ox}$ are any suitable conditions for oxidizing the compound of Formula (S)-D or (R)-D to provide a compound of Formula (S)-$D^{ox}$ or (R)-$D^{ox}$ respectively known in the art, for example, using the synthetic procedures found in *Journal of Organic Chemistry*, 70(11), 4397-4408; 2005 or *Faming Zhuanli Shenqing*, 103626713, 12 Mar. 2014.

In some embodiments, the compound of Formula (S)-D or (R)-D is oxidized in the presence of a suitable oxidizing agent to provide the compound of Formula (S)-$D^{ox}$ or (R)-$D^{ox}$, respectively. In some embodiments, the suitable oxidizing agent is any suitable oxidizing agent that oxidizes the hydroxy group of the compound of Formula (S)-D or (R)-D to an aldehyde of the compound of Formula (S)-$D^{ox}$ or (R)-$D^{ox}$, respectively. In some embodiments, the suitable oxidizing agent is phosgene, Dess-Martin periodinane, sodium hypochlorite with 2,2,6,6-tetramethylpiperidin-1-yl) oxyl or (2,2,6,6-tetramethylpiperidin-1-yl)oxidanyl (TEMPO) or oxalyl chloride with dimethylsulfoxide. In some embodiments, the suitable oxidizing agent is phosgene. Accordingly, in some embodiments, the compound of Formula (S)-D or (R)-D is oxidized in the presence of phosgene in a suitable solvent such as DMSO or methylene chloride ($CH_2Cl_2$) and mixture thereof, for a time and a temperature to provide the compound of Formula (S)-$D^{ox}$ or (R)-$D^{ox}$, respectively. In some embodiments, the suitable oxidizing agent is Dess-Martin periodinane. Accordingly, in some embodiments, the compound of Formula (S)-D or (R)-D is oxidized in the presence of Dess-Martin periodinane to provide the compound of Formula (S)-$D^{ox}$ or (R)-$D^{ox}$, respectively. In some embodiments, the compound of Formula (S)-D or (R)-D is oxidized in the presence of a slight excess amount (for example, about 1.1 to about 1.5 molar equivalents Dess-Martin periodinane in a suitable solvent such as methylene chloride ($CH_2Cl_2$) for a time and a temperature to provide the compound of Formula (S)-$D^{ox}$ or (R)-$D^{ox}$, respectively. As representative, non-limiting examples, the temperature and times for oxidizing the compound of Formula (S)-D or (R)-D in the presence of Dess-Martin periodinane to provide the compound of Formula (S)-$D^{ox}$ or (R)-$D^{ox}$, respectively is about 18° C. to about 25° C. or about 20° C. to about 25° C. or room temperature for about for about 1 hour to about 4 hours, about 1 hours to about 3 hours, about 2 hours to about 3 hours, or about 3 hours.

In some embodiments, the suitable oxidizing agent is a hypochlorite with 2,2,6,6-tetramethylpiperidin-1-yl)oxyl or (2,2,6,6-tetramethylpiperidin-1-yl)oxidanyl (TEMPO). Accordingly, in some embodiments, the compound of Formula (S)-D or (R)-D is oxidized in the presence of a hypochlorite with TEMPO to provide the compound of Formula (S)-$D^{ox}$ or (R)-$D^{ox}$, respectively. In some embodiments, the compound of Formula (S)-D or (R)-D is oxidized in the presence of a slight excess amount (for example, about 1.1 to about 1.5 molar equivalents) hypochlorite and a catalytic amount (for example, about 0.1 to about 0.3 molar equivalents) of TEMPO in a suitable solvent such as methylene chloride ($CH_2Cl_2$) and water and a for a time and a temperature to provide the compound of Formula (S)-$D^{ox}$ or (R)-$D^{ox}$, respectively. In some embodiments, the compound of Formula (S)-D or (R)-D is combined with TEMPO in the suitable solvent, for example, methylene chloride ($CH_2Cl_2$) and water, at room temperature to form a reaction mixture. In some embodiments, the reaction mixture is lowered to a temperature of about 5° C. to about 10° C. or about 5° C. and hypochlorite is added to provide the compound of Formula (S)-$D^{ox}$ or (R)-$D^{ox}$, respectively. In some embodiments, the hypochlorite is sodium hypochlorite. In some embodiments, the Formula (S)-D or (R)-D is oxidized in the presence of a hypochlorite with TEMPO and a cocatalyst to provide the compound of Formula (S)-$D^{ox}$ or (R)-$D^{ox}$, respectively. In some embodiments, the cocatalyst is sodium bromide. In some embodiments, the cocatalyst is combined with compound of Formula (S)-D or (R)-D and TEMPO.

In some embodiments, the compound of Formula (S)-D or (R)-D is oxidized under any suitable oxidizing conditions to oxidize the hydroxy of the compound of Formula (S)-D or (R)-D to the aldehyde of the compound of Formula (S)-$D^{ox}$ or (R)-$D^{ox}$, respectively. In some embodiments, the compound of Formula (S)-D or (R)-D is oxidized under Swern oxidation conditions to provide the compound of Formula (S)-$D^{ox}$ or (R)-$D^{ox}$, respectively. Accordingly, in some embodiments, the compound of Formula (S)-D or (R)-D is oxidized with oxalyl chloride, dimethyl sulfoxide in the presence of an organic base to provide the compound of Formula (S)-$D^{ox}$ or (R)-$D^{ox}$, respectively. In some embodiments, the compound of Formula (S)-D or (R)-D is oxidized with a slight excess amount (e.g. about 1.1 to about 1.5 molar equivalents) oxalyl chloride, an excess amount of dimethyl sulfoxide (e.g. about 1.5 to about 2.5 molar equivalents or about 2.5 molar equivalents) in an inert solvent and an organic base for a temperature and a time provide the compound of Formula (S)-$D^{ox}$ or (R)-$D^{ox}$, respectively. In some embodiments, the inert solvent is methylene chloride. In some embodiments, the is selected from alkylamines such as triethylamine (TEA), DIPEA (diisopropylethylamine), and triisopropyl amine; N-alkylmorpholines, N-alkylpyrrolidines, N-alkylpiperidines, tertiary diazabicyclic amines such as DBU (1,8-Diazabicyclo[5.4.0]undec-7-ene), DABCO 1,4-Diazabicyclo [2.2.2] octane), and DBN (1,5-Diazabicyclo[4.3.0]non-5-ene), substituted and non-substituted aromatic amines such as pyridine, DMAP (N,N-diethylaminopiperidine), pyrimidine, N-alkylpyrrole, N-alkylimidazole, N-alkylcarbazole, N-alkylindole, and triazine, guanidine bases such as tetraalkyl guanidines, and N,N-dialkylpiperizines. In some embodiments, the base is selected from TEA, DIPEA, triisopropyl amine, and 1,8-DBU. In some embodiments, the base is DIPEA.

In some embodiments, dimethyl sulfoxide is added, for example, dropwise over, for example, about 15 to about to 30 minutes a solution of oxalyl chloride in the inert solvent at a temperature, for example, about −70° C. to about −60° C. or −60° C. to form a reaction mixture. In some embodiments, the compound of Formula (S)-D or (R)-D is then added to the reaction mixture, for example, dropwise over, for example, about 15 to about to 30 minutes to the reaction mixture and stirred a temperature, for example, about −70° C. to about −60° C. or −60° C. for about 15 to about to 30 minutes. In some embodiments, the organic base is then further added to the reaction mixture for example, dropwise over, for example, about 15 to about to 30 minutes and stirred a temperature, for example, about −70° C. to about −50° C. or −60° C. for about 30 minutes to about 1 hour, or about 30 minutes and then allowed to warm to room temperature.

In some embodiments, the conditions for providing the compound of formula (S)-D' or (R)-D' are any suitable conditions for reacting the compound of Formula (S)-$D^{ox}$ or (R)-$D^{ox}$ with a methyl organometallic reagent to provide a compound of Formula (S)-D' or (R)-D', respectively known in the art, for example, using the synthetic procedures found in *Faming Zhuanli Shenqing,* 103626713, 12 Mar. 2014.

In some embodiments, the compound of Formula (S)-$D^{ox}$ or (R)-$D^{ox}$, is reacted with an excess (for example, about 1.1 to about 3 molar equivalent) of the methyl organometallic reagent in a suitable inert solvent for a time and a temperature to provide the compound of Formula (S)-D' or (R)-D', respectively. In some embodiments, the suitable inert solvent is selected from diethyl ether, tetrahydrofuran, 1,2-dimethoxyethane, and diethyleneglycol dimethylether. In some embodiments, the compound of Formula (S)-$D^{ox}$ or (R)-$D^{ox}$ is reacted with an organometallic reagent in a suitable solvent at a temperature of 80° C. to about −70° C. or about −78° C. and then warmed to about 0° C. to about 10° C., about 0° C. to about 5° C. or about 0° C. for about 30 minutes to about 1 hour or about 30 minutes to provide the compound of Formula (S)-D' or (R)-D', respectively.

In some embodiments, the methyl organometallic reagent is a Grignard reagent or methyllithium. In some embodiments, the methyl organometallic reagent is a Grignard reagent. In some embodiments, the Grignard reagent is $CH_3MgBr$. In some embodiments, the methyl organometallic reagent is methyllithium.

In some embodiments, the compound of Formula (S)-D or (R)-D is reacted with the chlorinating agent to provide a compound of Formula (S)-E or (R)-E, respectively, or the compound of Formula of (S)-D' or (R)-D' is reacted with the chlorinating agent to provide a compound of Formula (S)-E' or (R)-E', respectively under any suitable conditions for reacting a compound of Formula (S)-D or (R)-D to provide a compound of Formula (S)-E or (R)-E, respectively, or for reacting a compound of Formula (S)-D' or (R)-D' to provide a compound of Formula (S)-E' or (R)-E', respectively, for example, using the synthetic procedures found in WO2011/029920 and WO2010/059658.

In some embodiments, the compound of Formula (S)-D or (R)-D or a compound of Formula (S)-D' or (R)-D' is reacted with any suitable chlorinating reagent at temperatures and times for providing the compound of Formula (S)-E or (R)-E, respectively or a compound of Formula (S)-E' or (R)-E' respectively. In some embodiments, the suitable chlorinating reagent is selected from thionyl chloride ($SOCl_2$), phosphorus trichloride ($PCl_3$), phosphorus pentachloride ($PCl_5$) and oxalyl chloride [$(COCl)_2$]. In some embodiments, the suitable chlorinating reagent is $SOCl_2$.

In some embodiments, the compound of Formula (S)-D or (R)-D or the compound of Formula (S)-D' or (R)-D' is reacted with an excess amount (for example about 1.5 to about 3, or about 2 molar equivalents) of the chlorinating agent, such as $SOCl_2$, at about 0° C. to about 10° C., or about 0° C. to about 5° C., for about 1 hour to about 24 hours, about 6 hours to about 20 hours, about 12 hours to about 20 hours or about 16 hours. In some embodiments, the compound of Formula (S)-D or (R)-D or the compound of Formula (S)-D' or (R)-D' is combined with an excess amount (for example about 1.5 to about 3, or about 2 molar equivalents) of the chlorinating agent, such as $SOCl_2$, at about 0° C. to about 10 and then the temperature is increased to about 10° C. to about 15° C.

In some embodiments, the compound of Formula (S)-C' or (R)-C' is prepared using any suitable conditions for hydrolyzing the compound of Formula (S)-C or (R)-C' to provide the compound of Formula (S)-C' or (R)-C', respectively known in the art, for example, using the synthetic procedures found in Journal of Medicinal Chemistry, 61 (18), 8468-8473 (2018).

In some embodiments, compound of Formula (S)-C or (R)-C is hydrolyzed to provide the compound of Formula (S)-C' or (R)-C' respectively with a base. Therefore, in some embodiments, the process comprises hydrolyzing the compound of Formula (S)-C or (R)-C with a base to provide the compound of Formula (S)-C' or (R)-C', respectively.

In some embodiments, the base is an inorganic base. In some embodiments, the base is a hydroxide base. In some embodiments, the base is NaOH or KOH.

In some embodiments, the compound of Formula (S)-C or (R)-C is reacted with a slight excess amount of base (for example about 1.1 to about 1.5 molar equivalents) in a suitable solvent at temperatures and times for providing the compound of Formula (S)-C' or (R)-C', respectively. In some embodiments, the suitable solvent is a $C_{1-6}$alkanol. In some embodiments, the $C_{1-6}$alkanol is selected from MeOH, EtOH and iPrOH. In some embodiments, the $C_{1-6}$alkanol is MeOH. As representative, non-limiting examples, the temperature and times for hydrolyzing the compound of Formula (S)-C or (R)-C with a base to provide the compound of Formula (S)-C' or (R)-C' respectively is about 18° C. to about 25° C. or about 20° C. to about 25° C. or room temperature for about 1 hour to about 6 hours, about 2 hours to about 5 hours, about 3 hours to about 4 hours, or about 4 hours.

In some embodiments, the compound of Formula (S)-C' or (R)-C' is converted to compound of Formula (S)-E" or (R)-E" under any suitable conditions for converting a compound of Formula (S)-C' or (R)-C' to a compound of Formula (S)-E" or (R)-E", respectively, for example, using the synthetic procedures found in *Chemistry—A European Journal,* 27(7), 2483-2492; 2021.

In some embodiments, the compound of Formula (S)-C' or (R)-C' is converted to the compound of Formula (S)-E" or (R)-E" respectively under Weinreb-Nahm ketone synthesis conditions.

Accordingly, in some embodiments, the step of converting the compound of Formula (S)-C' or (R)-C' to the compound of Formula (S)-E" or (R)-E" comprises;

reacting the compound of Formula (S)-C' or (R)-C' with N,O-dimethylhydroxylamine,

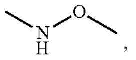

to provide the amide compound of Formula (S)-E"" or (R)-E"", respectively (S)-E'''

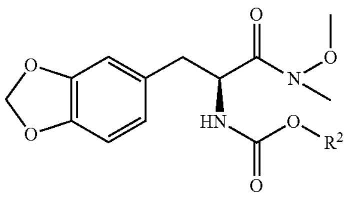

or (R)-E'''

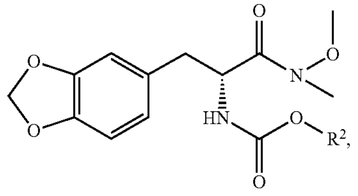

wherein $R^2$ is $C_{1-4}$alkyl or $CH_2Ph$; and reacting the compound of Formula (S)-E"" or (R)-E"" with a methyl organometallic reagent to provide the compound of Formula (S)-E" or (R)-E", respectively, (S)-E"

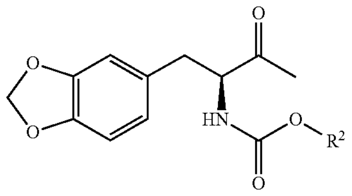

or (R)-E"

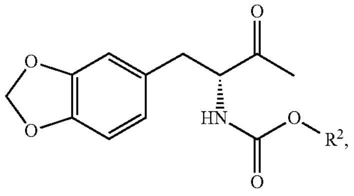

wherein $R^2$ is $C_{1-4}$alkyl or $CH_2Ph$.

In some embodiments, the step of reacting the compound of Formula (S)-C' or (R)-C' with N,O-dimethylhydroxylamine to provide the amide compound of Formula (S)-E"" or (R)-E"", respectively is under any suitable conditions for reacting the compound of Formula (S)-C' or (R)-C' with N,O-dimethylhydroxylamine to provide a compound of Formula (S)-E"" or (R)-E, respectively for example, using the synthetic procedures found in *Chemistry—A European Journal,* 27(7), 2483-2492; 2021.

In some embodiments, reacting the compound of Formula (S)-C' or (R)-C' with N,O-dimethylhydroxylamine to provide the amide compound of Formula (S)-E"" or (R)-E"" comprises activating the carboxylic acid group of the compound of Formula (S)-C' or (R)-C' with an activating agent following by coupling with N,O-dimethylhydroxylamine to provide the amide compound of Formula (S)-E''' or (R)-E"", respectively. Accordingly, in some embodiments, the process comprises reacting the compound of Formula (S)-C' or (R)-C' with N,O-dimethylhydroxylamine in the presence of an activating agent to provide the compound of Formula (S)-E" or (R)-E", respectively. In some embodiments, the process comprises reacting the compound of Formula (S)-C' or (R)-C' with N,O-dimethylhydroxylamine in the presence of an activating agent and a base to provide the compound of Formula (S)-E"" or (R)-E"", respectively.

It would be appreciated by a person skilled in the art that amide compound of Formula (S)-E"" or (R)-E"" can be prepared by reacting the compound of Formula (S)-C' or (R)-C' with N,O-dimethylhydroxylamine in the presence of an activating agent to provide the compound of Formula (S)-E" or (R)-E" respectively in a two-step process comprising:

reacting the carboxylic acid group of compound of Formula (S)-C' or (R)-C' with an activating agent to provide an activated carboxylic acid intermediate compound, and reacting the activated carboxylic acid intermediate compound reacted with N,O-dimethylhydroxylamine in to provide a compound of Formula (S)-E"" or (R)-E"", respectively.

In some embodiment, the activated carboxylic acid intermediate compound reacted is isolated. In some embodiment, the activated carboxylic acid intermediate compound reacted is not isolated.

In some embodiments, the activating agent is a coupling reagent. Accordingly, in some embodiments, the process comprises reacting the compound of Formula (S)-C' or (R)-C' with N,O-dimethylhydroxylamine in the presence of a coupling agent to provide the compound of Formula (S)-E"" or (R)-E"", respectively. In some embodiments, the coupling reagent is any suitable coupling reagent known in the art, for example, the coupling reagents disclosed in Bodansky, M., Principles of Peptide Synthesis, $2^{nd}$ ed. Springer Verlag Berlin/Heidelberg, 1993. In some embodiments, the coupling reagents is an acylating agents such as a mixed anhydride, activated ester or acid halogenide, for example, isobutyl-chloroformate; carbodiimides; activated benzotriazine derivatives including 3-(diethoxyphosphoryloxy)-1,2,3-benzotriazin-4(3H)-one (DEPBT); or uranium or phosphonium salt derivatives of benzotriazole.

In some embodiments, the uranium or phosphonium salt derivatives of benzotriazol are selected from HBTU (O-1H-benzotriazole-1-yl)-N,N,N',N'-tetramethyluronium hexafluorophosphate), BOP (benzotriazole-1-yl-oxy-tris-(dimethylamino)-phosphonium hexafluorophosphate), PyBOP (benzotriazole-1-yl-oxytripyrrolidinophosphonium hexafluorophosphate), PyAOP (7-Azabenzotriazol-1-yloxy) tripyrrolidinophosphonium hexafluorophosphate), HCTU (O-(1H-6-chloro-benzotriazole-1-yl)-1,1,3,3-tetramethyl-uronium hexafluorophosphate), TCTU (O-1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N"-tetramethyluronium tetrafluoroborate), HAPyU (O-(benzotriazol-1-yl)oxybis-(pyrrolidino)-uronium hexafluorophosphate. In some embodiments, the coupling reagent is HBTU.

In some embodiments, the activating agent is thionyl chloride.

In some embodiments, the N,O-dimethylhydroxylamine is generated in situ by reacting acid salt of dimethylhydroxylamine with a base. Accordingly, the N,O-dimethylhydroxylamine is an acid salt of dimethylhydroxylamine, and the compound of Formula (S)-C' or (R)-C' is reacted with an acid salt of N,O-dimethylhydroxylamine in the presence of a base.

In some embodiments, the base is an organic base. In some embodiments, the base is selected from alkylamines such as triethylamine (TEA), DIPEA (diisopropylethylamine), and triisopropyl amine; N-alkylmorpholines, N-alkylpyrrolidines, N-alkylpiperidines, tertiary diazabicyclic amines such as DBU (1,8-Diazabicyclo[5.4.0]undec-7-ene), DABCO 1,4-Diazabicyclo [2.2.2] octane), and DBN (1,5-Diazabicyclo[4.3.0]non-5-ene), substituted and non-substituted aromatic amines such as pyridine, DMAP (N,N-diethylaminopiperidine), pyrimidine, N-alkylpyrrole, N-alkylimidazole, N-alkylcarbazole, N-alkylindole, and triazine, guanidine bases such as tetraalkyl guanidines, and N,N-dialkylpiperizines. In some embodiments, the base is selected from TEA, DIPEA, triisopropyl amine, and 1,8-DBU. In some embodiments, the base is DIPEA.

In some embodiments, the compound of Formula (S)-C' or (R)-C' is reacted an excess amount (for example, an about 1.3 to about 2 molar equivalent, or about 1.5 molar equivalent) of N,O-dimethylhydroxylamine or acid salt of N,O-dimethylhydroxylamine in the presence of an excess amount (for example, an about 1.3 to about 2 molar equivalent, or about 1.5 molar equivalent) of an activating agent an excess amount (for example, an about 3 to about 6 molar equivalents, or about 4.5 molar equivalent) of base in a suitable solvent for a time and a temperature to provide the amide compound of Formula (S)-E or (R)-E"", respectively. In some embodiments, the acid salt of dimethylhydroxylamine is hydrochloric acid salt of N,O-dimethylhydroxylamine (N,O-dimethylhydroxylamine·HCl).

As representative, non-limiting examples, the temperature and times for reacting the compound of Formula (S)-C' or (R)-C' with N,O-dimethylhydroxylamine in the presence of an activating agent to provide the compound of Formula (S)-E" or (R)-E""respectively is about 18° C. to about 25° C. or about 20° C. to about 25° C. or room temperature for about for about 1 hour to about 4 hours, about 2 hours to about 3 hours or about 2 hours. In some embodiments, reacting the compound of Formula (S)-E"" or (R)-E"" with a methyl organometallic reagent to provide the compound of Formula (S)-E" or (R)-E", respectively is under any suitable conditions for reacting the compound of Formula (S)-E"" or (R)-E"" with a methyl organometallic reagent to provide the compound of Formula (S)-E" or (R)-E", respectively for example, using the synthetic procedures found in *Chemistry—A European Journal,* 27(7), 2483-2492; 2021 or U.S. Pat. No. 5,827,827.

In some embodiments, the compound of Formula (S)-E"" or (R)-E"" is reacted with an excess (for example, about 1.1 to about 3 molar equivalent) of the methyl organometallic reagent in a suitable inert solvent for a time and a temperature to provide the compound of Formula (S)-E" or (R)-E" respectively. In some embodiments, the suitable inert solvent is selected from tetrahydrofuran, 1,2-dimethoxyethane, and diethyleneglycol dimethylether and mixtures thereof. As representative, non-limiting examples, the temperature and times for reacting the compound of Formula (S)-E or (R)-E"" with the methyl organometallic reagent to provide the compound of Formula (S)-E" or (R)-E" respectively is about −80° C. to about 0° C. for about 1 hour to about 4 hours, about 1 hours to about 3 hours, or about 1 hours to about 2 hours.

In some embodiments, the methyl organometallic reagent is a Grignard reagent or methyllithium. In some embodiments, the methyl organometallic reagent is a Grignard reagent. In some embodiments, the Grignard reagent is $CH_3MgBr$. In some embodiments, the methyl organometallic reagent is methyllithium.

In some embodiments, the reducing agent to provide the compound of Formula (R)-I or (S)-I from the compound of Formula (S)-E or (R)-E or compound of Formula (S)-E' or (R)-E' respectively is any suitable reducing agent that reduces the alkylchloride of the compound of Formula (S)-E or (R)-E or the compound of Formula (S)-E' or (R)-E' to an alkane and that reduces the $C_{1-4}$alkoxycarbonyl protected amine of the compound of Formula (S)-E or (R)-E or the compound of Formula (S)-E' or (R)-E' to an N-methyl amine.

In some embodiments, the reducing agent to provide the compound of Formula (R)-I or (S)-I when R is $CH_2CH_3$ (i.e., (R)-MBDB and (S)-MBDB) from the compound of Formula of Formula (S)-E" or (R)-E" is any suitable reducing agent that reduces the ketone of the compound of Formula (S)-E" or (R)-E" to an alkane and that reduces the $C_{1-4}$alkoxycarbonyl protected amine of the compound of Formula (S)-E' or (R)-E to an N-methyl amine.

In some embodiments, the compound of Formula R-I or S-I is provided by reacting the compound of Formula (S)-E or (R)-E, the compound of Formula (S)-E' or (R)-E' or the compound of Formula (S)-E" or (R)-E" with an excess amount (for example, an about 2 to about 5 molar equivalent, or about 2 molar equivalents) of the suitable reducing agent in an inert solvent such as THF at temperatures for the reaction of the compound of Formula (S)-E or (R)-E, the compound of Formula (S)-E' or (R)-E' or the compound of Formula (S)-E" or (R)-E" with the reducing agent to provide the compound of Formula (R)-I or (S)-I respectively. As representative, non-limiting example of temperature and reaction times, the compound of Formula (S)-E or (R)-E, the compound of Formula (S)-E' or (R)-E' or the compound of Formula (S)-E" or (R)-E" is combined with the reducing agent in in the inert solvent at about 0° C. to about 10° C., about 0° C. to about 5° C., or about 0° C. to form a reaction mixture and then the reaction mixture is heated to reflux for about 1 hour to about 4 hours, about 1 hours to about 3 hours, or about 2 hours under an inert atmosphere to provide a compound of Formula (R)-I or (S)-I. In some embodiments, the inert atmosphere is argon or nitrogen.

In some embodiments, the suitable reducing agent for reacting with the compound of Formula (S)-E or (R)-E, the compound of Formula (S)-E' or (R)-E' or the compound of Formula (S)-E" or (R)-E" is a metal hydride. In some embodiments, the metal hydride is selected from lithium borohydride, sodium borohydride and lithium aluminium hydride. In some embodiments, the metal hydride is lithium aluminium hydride.

In some embodiments, a byproduct in the conversion of the compound of Formula (S)-E or (R)-E or the compound of Formula (S)-E' or (R)-E' to the compound of Formula (R)-I or (S)-I, respectively may be the formation of an aziridine byproduct. In some embodiments, the aziridine byproduct is minimized by slowly adding compound of Formula (S)-E or (R)-E or the compound of Formula (S)-E' or (R)-E' to a solution of the reducing agent in the inert solvent instead adding the reducing agent to a solution of the compound of Formula (S)-E or (R)-E or the compound of Formula (S)-E' or (R)-E' in the inert solvent. Accordingly, in some embodiments, the reacting the compound of Formula (S)-E or (R)-E or the compound of Formula (S)-E' or (R)-E' with a reducing agent to provide the compound of Formula (R)-I or (S)-I, respectively comprises adding the compound of Formula (S)-E or (R)-E or the compound of Formula (S)-E' or (R)-E' to a solution of the reducing agent in an inert solvent over a period of time. In some embodiments, the period of time is about 1 hour to about 24 hours, about 1 hour to about 20 hours, about 2 hours to about 18 hours, about 4 hours to about 8 hours, about 6 hours to about 12 hours, about 8 hours to about 10 hours, about 12 hours to about 16 hours, or about 16 hours to about 20 hours. In some embodiments, the inert solvent is THF.

Alternatively, the reacting of the compound of Formula (S)-E or (R)-E or the compound of Formula (S)-E' or (R)-E' with a reducing agent to provide the compound of Formula (R)-I or (S)-I respectively comprises:

reacting a compound of Formula (S)-E or (R)-E or a compound of Formula (S)-E' or (R)-E' with a first reducing agent to provide a compound of Formula (S)-F or (R)-F:

(S)-F

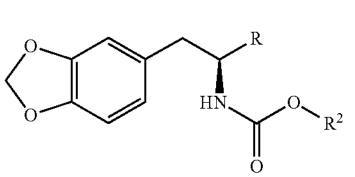

or (R)-F

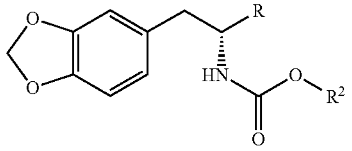

wherein

R is selected from $CH_3$ and $CH_2CH_3$; and $R^2$ is $C_{1-4}$alkyl or $CH_2Ph$; and reacting the compound of Formula (S)-F or (R)-F with a second reducing agent to provide the compound of Formula (R)-I or (S)-I, respectively.

In some embodiments, when R is $CH_3$ the compound of Formula (R)-I is (R)-MDMA and the compound of Formula (S)-I is (S)-MDMA and the reacting of the compound of Formula (S)-E or (R)-E with a reducing agent to provide the (R)-MDMA or (S)-MDMA respectively comprises:

reacting a compound of Formula (S)-E or (R)-E with a first reducing agent to provide a compound of Formula (S)-F or (R)-F:

(S)-F

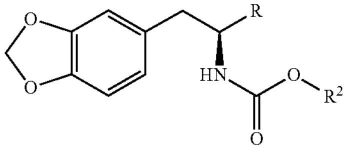

or (R)-F

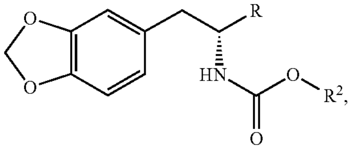

wherein

R is $CH_3$; and $R^2$ is $C_{1-4}$alkyl or $CH_2Ph$; and reacting the compound of Formula (S)-F or (R)-F with a second reducing agent to provide (R)-MDMA or (S)-MDMA, respectively.

In some embodiments, when R is $CH_2CH_3$ the compound of Formula (R)-I is (R)-MBDB and the compound of Formula (S)-I is (S)-MBDB and the reacting of the compound of Formula (S)-E' or (R)-E' with a reducing agent to provide the (R)-MBDB or (S)-MBDB respectively comprises:

reacting a compound of Formula (S)-E' or (R)-E' with a first reducing agent to provide a compound of Formula (S)-F or (R)-F:

(S)-F

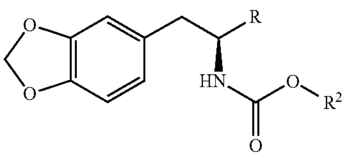

or (R)-F

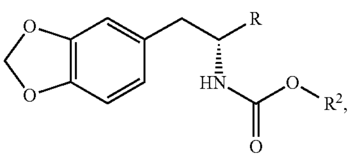

wherein R is $CH_2CH_3$; and $R^2$ is $C_{1-4}$alkyl or $CH_2Ph$; and reacting the compound of Formula (S)-F or (R)-F with a second reducing agent to provide the (R)-MBDB or (S)-MBDB, respectively.

In some embodiments, the compound of Formula (S)-E or (R)-E or the compound of Formula (S)-E' or (R)-E' is reacted with any suitable first reducing agent to provide a compound of Formula (S)-F or (R)-F, respectively. In some embodiments, when $R^2$ is $C_{1-4}$alkyl or $CH_2Ph$, the reducing agent is a metal hydride. In some embodiments, the metal hydride is tributyltin hydride. In some embodiments, when $R^2$ is $C_{1-4}$alkyl, the first reducing agent is a palladium catalyst. In some embodiments, the palladium catalyst is palladium on carbon (Pd/C) or palladium hydroxide on carbon ($Pd(OH)_2/C$). In some embodiments, the compound of Formula (S)-F or (R)-F is reacted with any suitable second reducing agent to provide the compound of Formula (R)-I or (S)-I respectively. In some embodiments, the second reducing agent is a metal hydride. In some embodiments, the metal hydride is selected from lithium borohydride, sodium borohydride, tributyltin hydride and lithium aluminium hydride. In some embodiments, the reducing agent is lithium aluminium hydride.

In some embodiments, when $R^2$ is $C_{1-4}$alkyl, the first reducing agent is tributyltin hydride or a palladium catalyst, and the second reducing reagent is lithium aluminium hydride. In some embodiments, when $R^2$ is $C_{1-4}$alkyl or $CH_2Ph$, the first reducing agent is tributyltin hydride, and the second reducing reagent is lithium aluminium hydride.

In some embodiments, the process provides the R or S enantiomer as the major isomer. In some embodiments, the process provides the R or S enantiomer in greater than 60% ee, 65% ee, 70% ee, 75% ee, 80% ee, 85% ee, 90% ee, 95% ee, 98% ee or 99% ee. In some embodiments, the process provides the R or S enantiomer of the MDMA ((R)-MDMA or (S)-MDMA) as the major isomer. In some embodiments, the process provides (R)-MDMA or (S)-MDMA in greater than 60% ee, 65% ee, 70% ee, 75% ee, 80% ee, 85% ee, 90% ee, 95% ee, 98% ee or 99% ee. In some embodiments, the process provides the R or S enantiomer of the MBDB ((R)-MBDB or (S)-MBDB) as the major isomer. In some embodiments, the process provides (R)-MBDB or (S)-MBDB in greater than 60% ee, 65% ee, 70% ee, 75% ee, 80% ee, 85% ee, 90% ee, 95% ee, 98% ee or 99% ee.

In an exemplary embodiment of a process of the application, $R^1$ and $R^2$ are each independently selected from $CH_3$ and $CH_2CH_3$ and the application includes a process for preparing a compound of Formula (R)-I or (S)-I (R)-I

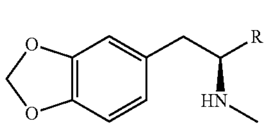

or (S)-I

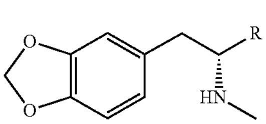

wherein R is selected from $CH_3$ and $CH_2CH_3$;

the process comprising:

protecting the amino group of a compound of Formula (S)-A or (R)-A:

(S)-A

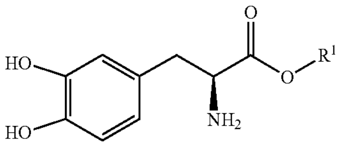

or (R)-A

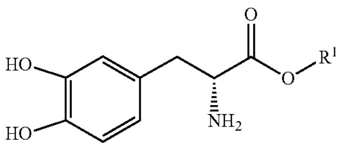

wherein $R^1$ is selected from $CH_3$ and $CH_2CH_3$, with a methoxycarbonyl protecting group or ethoxycarbonyl protecting group to provide a compound of Formula (S)-B or (R)-B, respectively:

(S)-B

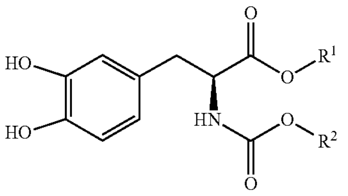

or

-continued (R)-B

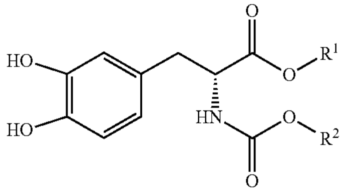

wherein $R^1$ is $CH_3$ or $CH_2CH_3$, and $R^2$ is $CH_3$ or $CH_2CH_3$;

cyclizing the compound of Formula (S)-B or (R)-B to provide a compound of Formula (S)-C or (R)-C, respectively:

(S)-C)

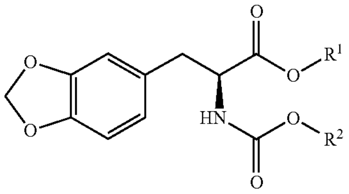

or (R)-C

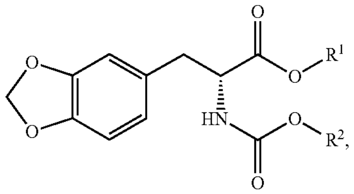

wherein $R^1$ is $CH_3$ or $CH_2CH_3$, and $R^2$ is $CH_3$ or $CH_2CH_3$;

reacting the compound of Formula (S)-C or (R)-C with a reducing agent to provide a compound of Formula (S)-D or (R)-D, respectively:

(S)-D

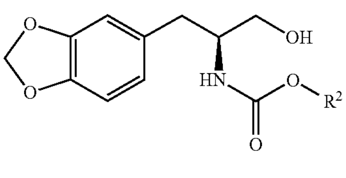

or (R)-D

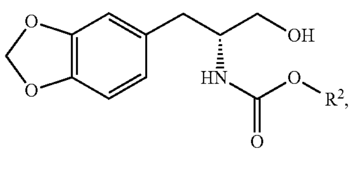

wherein $R^2$ is $CH_3$ or $CH_2CH_3$;

when R is $CH_2CH_3$, further oxidizing the compound of Formula (S)-D or (R)-D to provide a compound of Formula (S)-$D^{ox}$ or (R)-$D^{ox}$; and (S)-$D^{ox}$

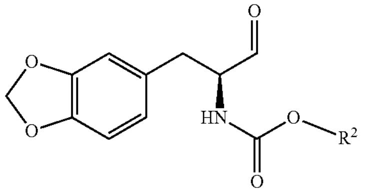

or (R)-$D^{ox}$

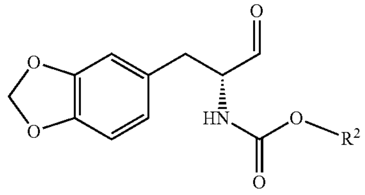

wherein $R^2$ is $CH_3$ or $CH_2CH_3$;

reacting the compound of Formula (S)-$D^{ox}$ or (R)-$D^{ox}$ with a methyl organometallic reagent to provide the compound of Formula (S)-D' or (R)-D', respectively;

(S)-D'

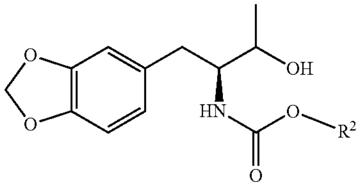

or (R)-D'

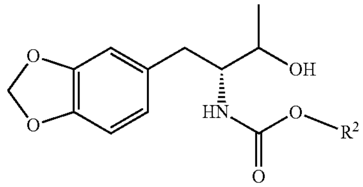

wherein $R^2$ is $CH_3$ or $CH_2CH_3$; and reacting the compound of Formula (S)-D or (R)-D or the compound of Formula of (S)-D' or (R)-D' with a chlorinating agent to provide a compound of Formula (S)-E or (R)-E or a compound of Formula (S)-E' or (R)-E', respectively:

(S)-E

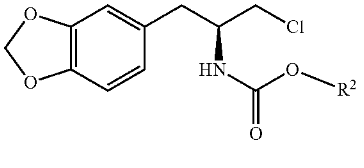

or (R)-E

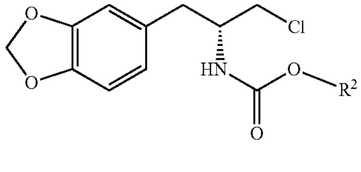

-continued (S)-E'

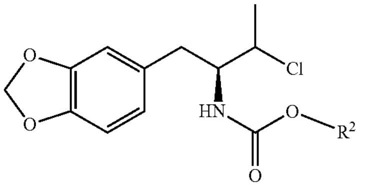

or (R)-E

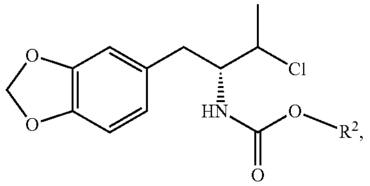

wherein $R^2$ is $CH_3$ or $CH_2CH_3$; or when R is $CH_2CH_3$, hydrolyzing the compound of Formula (S)-C or (R)-C to provide the compound of Formula (S)-C' or (R)-C', respectively;

(S)-C'

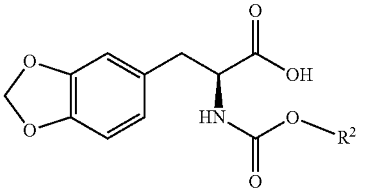

or (R)-C'

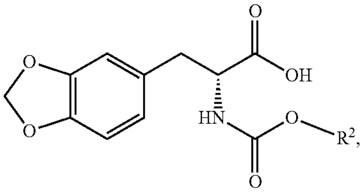

wherein $R^2$ is $CH_3$ or $CH_2CH_3$; and converting the compound of Formula (S)-C' or (R)-C' to the compound of Formula (S)-E" or (R)-E", respectively (S)-E"

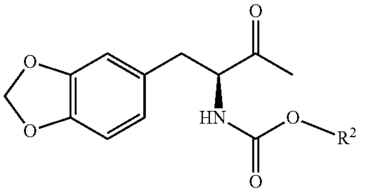

or (R)-E"

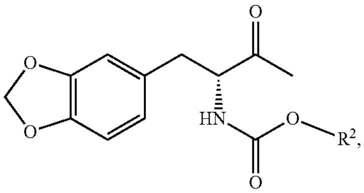

wherein $R^2$ is $CH_3$ or $CH_2CH_3$; and reacting the compound of Formula (S)-E with a reducing agent to provide the compound of Formula (R)-I, wherein R is $CH_3$, reacting the compound of Formula (S)-E' with a reducing agent to provide the compound of Formula (R)-I, wherein R is $CH_2CH_3$, or reacting the compound of Formula (S)-E" with a reducing agent to provide the compound of Formula (R)-I, wherein R is $CH_2CH_3$.

Alternatively, the reacting of the compound of Formula (S)-E or (R)-E or the compound of Formula (S)-E' or (R)-E' with a reducing agent to provide the compound of Formula (R)-I or (S)-I, respectively comprises:

reacting a compound of Formula (S)-E or (R)-E or a compound of Formula (S)-E' or (R)-E' with a first reducing agent to provide a compound of Formula (S)-F or (R)-F; and (S)-F

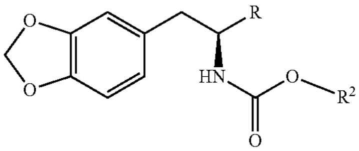

or (R)-F

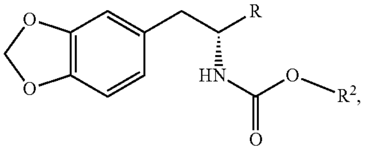

wherein

R is $CH_3$ or $CH_2CH_3$; and $R^2$ is $CH_3$ or $CH_2CH_3$; and reacting the compound of Formula (S)-F or (R)-F with a second reducing agent to provide the compound of Formula (R)-I or (S)-I, respectively.

In an exemplary embodiment of a process of the application, R is $CH_3$, $R^1$ and $R^2$ are each independently selected from $CH_3$ and $CH_2CH_3$ and the application includes a process for preparing (R)-3,4-methylenedioxymethamphetamine ((R)-MDMA):

(R)-MDMA

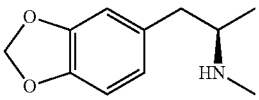

the process comprising:

protecting the amino group of a compound of Formula (S)-A:

(S)-A

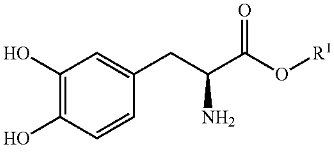

wherein $R^1$ is $CH_3$ or $CH_2CH_3$;

with a methoxycarbonyl protecting group or ethoxycarbonyl protecting group to provide a compound of Formula (S)-B:

(S)-B

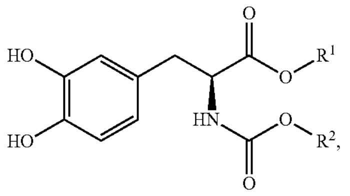

wherein $R^1$ is $CH_3$ or $CH_2CH_3$, and $R^2$ is $CH_3$ or $CH_2CH_3$;

cyclizing the compound of Formula (S)-B to provide a compound of Formula (S)-C:

(S)-C

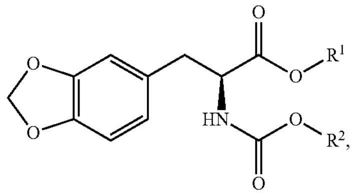

wherein $R^1$ is $CH_3$ or $CH_2CH_3$; and $R^2$ is $CH_3$ or $CH_2CH_3$;

reacting the compound of Formula (S)-C with a reducing agent to provide a compound of Formula (S)-D:

(S)-D

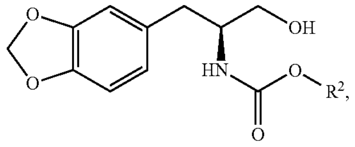

wherein $R^2$ is $CH_3$ or $CH_2CH_3$;

reacting the compound of Formula (S)-D with a chlorinating agent to provide a compound of Formula (S)-E:

(S)-E

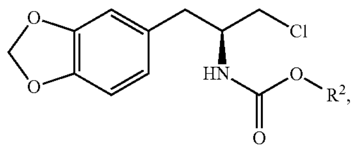

wherein $R^2$ is $CH_3$ or $CH_2CH_3$; and reacting the compound of Formula (S)-E with a reducing agent to provide the (R)-MDMA.

In an exemplary embodiment of a process of the application, R is $CH_3$, $R^1$ and $R^2$ are each independently selected from $CH_3$ and $CH_2CH_3$ and the application includes a process for preparing (S)-3,4-methylenedioxymethamphetamine ((S)-MDMA):

(S)-MDMA

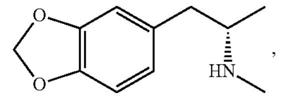

the process comprising:

protecting the amino group of a compound of Formula or (R)-A:

(R)-A

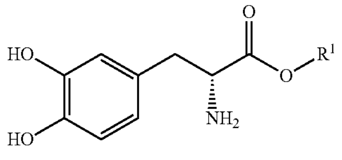

wherein $R^1$ is $CH_3$ or $CH_2CH_3$;

with a methoxycarbonyl protecting group or ethoxycarbonyl protecting group to provide a compound of Formula (R)-B:

(R)-B

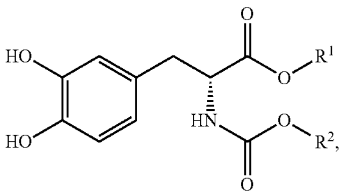

wherein $R^1$ is $CH_3$ or $CH_2CH_3$, and $R^2$ is $CH_3$ or $CH_2CH_3$;

cyclizing the compound of Formula (R)-B to provide a compound of Formula (R)-C:

(R)-C

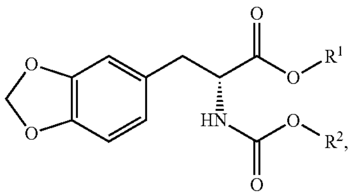

wherein $R^1$ is $CH_3$ or $CH_2CH_3$; and $R^2$ is $CH_3$ or $CH_2CH_3$;

reacting the compound of Formula (R)-C with a reducing agent to provide a compound of Formula (R)-D:

(R)-D

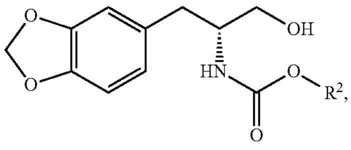

wherein $R^2$ is $CH_3$ or $CH_2CH_3$;

reacting the compound of Formula (R)-D with a chlorinating agent to provide a compound of Formula (R)-E, respectively:

(R)-E

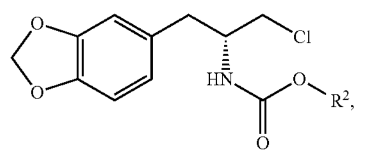

wherein $R^2$ is $CH_3$ or $CH_2CH_3$; and reacting the compound of Formula (R)-E with a reducing agent to provide the (S)-MDMA.

In some embodiments, the compound of Formula (S)-A or (R)-A is protected with a methoxycarbonyl protecting group.

In some embodiments, the step of cyclizing the compound of Formula (S)-B or (R)-B to provide a compound of Formula (S)-C or (R)-C respectively, comprises combining the compound of Formula (S)-B or (R)-B with an excess amount (for example, about 3 to about 5, or about 3 to about 4 molar equivalent) of potassium carbonate and an excess (for example, about 2 to about 2.5 molar equivalent) of diiodomethane in an inert solvent such as acetone.

In some embodiments, embodiments, the reducing agent for reacting with the compound of Formula (S)-C or (R)-C to provide the compound of Formula (S)-D or (R)-D respectively is lithium aluminium hydride.

In some embodiments, the chlorinating reagent for reacting with the compound of Formula (S)-D or (R)-D is thionyl chloride.

In some embodiments, embodiments, the reducing agent for reacting with the compound of Formula (S)-E or (R)-E to provide R-MDMA or (S)-MDMA, respectively is lithium aluminium hydride. Alternatively, the reacting of the compound of Formula (S)-E or (R)-E with a reducing agent to provide the (R)-MDMA or (S)-MDMA, respectively comprises reacting a compound of Formula (S)-E or (R)-E with a first reducing agent to provide a compound of Formula (S)-F or (R)-F, respectively; and (S)-F

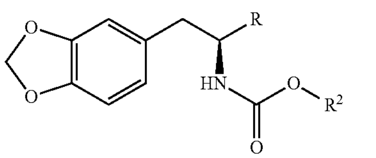

or (R)-F

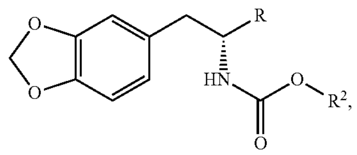

wherein $R^1$ is $CH_3$; and $R^2$ is $CH_3$ or $CH_2CH_3$; and reacting the compound of Formula (S)-F or (R)-F with a second reducing agent to provide the (R)-MDMA or (S)-MDMA, respectively.

In an exemplary embodiment of a process of the application, R is $CH_2CH_3$, $R^1$ and $R^2$ are each independently selected from $CH_3$ and $CH_2CH_3$ and the application includes a process for preparing (R)—N-methyl-1,3-benzodioxolylbutanamine ((R)-MBDB (R)-MBDB

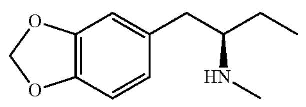

the process comprising:

protecting a compound of Formula (S)-A:

(S)-A

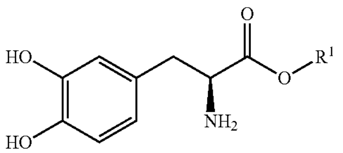

wherein $R^1$ is $CH_3$ or $CH_2CH_3$, with a methoxycarbonyl protecting group or ethoxycarbonyl protecting group to provide a compound of Formula (S)-B:

(S)-B

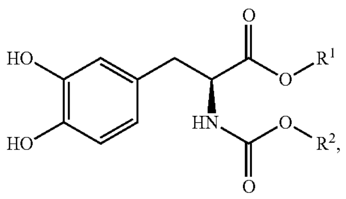

wherein $R^1$ is $CH_3$ or $CH_2CH_3$, and $R^2$ is $CH_3$ or $CH_2CH_3$;

cyclizing the compound of Formula (S)-B to provide a compound of Formula (S)-C:

(S)-C

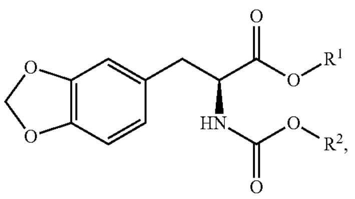

wherein $R^1$ is $CH_3$ or $CH_2CH_3$, and $R^2$ is $CH_3$ or $CH_2CH_3$;

reacting the compound of Formula (S)-C with a reducing agent to provide a compound of Formula (S)-D:

(S)-D

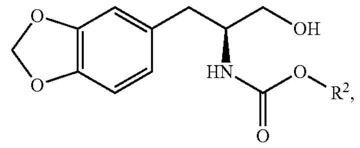

wherein $R^2$ is $CH_3$ or $CH_2CH_3$ oxidizing the compound of Formula (S)-D to provide a compound of Formula (S)-$D^{ox}$;

(S)-$D^{ox}$

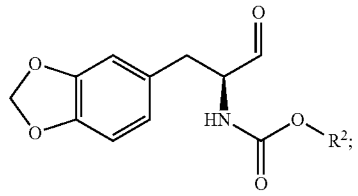

wherein $R^2$ is $CH_3$ or $CH_2CH_3$;

reacting the compound of Formula (S)-$D^{ox}$ with a methyl organometallic reagent to provide the compound of Formula (S)-D';

(S)-D'

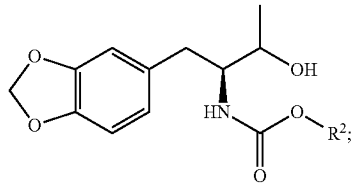

wherein $R^2$ is $CH_3$ or $CH_2CH_3$;

reacting the compound of Formula (S)-D' with a chlorinating agent to provide a compound of Formula (S)-E':

(S)-E'

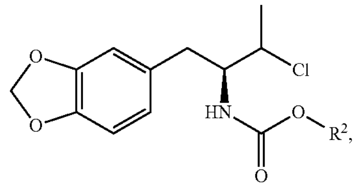

wherein $R^2$ is $CH_3$ or $CH_2CH_3$; and reacting the compound of Formula (S)-E' with a reducing agent to provide the (R)-MBDB.

Alternatively, the reacting the compound of Formula (S)-E' with a reducing agent to provide the compound of Formula (R)-I comprises:

reacting a compound of Formula (S)-E' with a first reducing agent to provide a compound of Formula (S)-F; and (S)-F

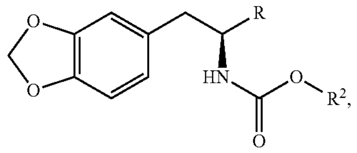

wherein

R is $CH_2CH_3$; and $R^2$ is $CH_3$ or $CH_2CH_3$; and reacting the compound of Formula (S)-F with a second reducing agent to provide the compound of Formula (R)-I.

In an exemplary embodiment of a process of the application, R is $CH_2CH_3$, $R^1$ and $R^2$ are each independently selected from $CH_3$ and $CH_2CH_3$ and the application includes a process for preparing (S)—N-methyl-1,3-benzodioxolylbutanamine ((S)-MBDB)

(S)-MBDB

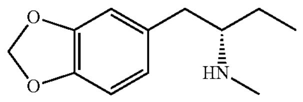

the process comprising:

protecting a compound of Formula (R)-A:

(R)-A

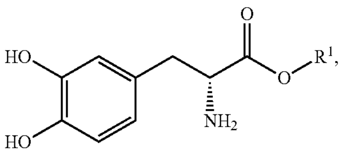

wherein $R^1$ is $CH_3$ or $CH_2CH_3$, with a methoxycarbonyl protecting group or ethoxycarbonyl protecting group to provide a compound of Formula (R)-B:

(R)-B

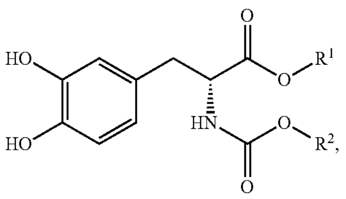

wherein $R^1$ is $CH_3$ or $CH_2CH_3$, and $R^2$ is $CH_3$ or $CH_2CH_3$;

cyclizing the compound of Formula (R)-B to provide a compound of Formula (R)-C:

(R)-C

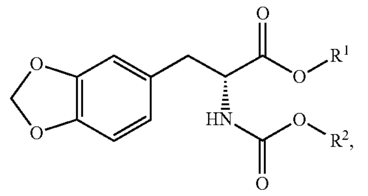

wherein $R^1$ is $CH_3$ or $CH_2CH_3$, and $R^2$ is $CH_3$ or $CH_2CH_3$;

reacting the compound of Formula (R)-C with a reducing agent to provide a compound of Formula (R)-D:

(R)-D

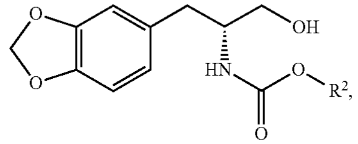

wherein $R^2$ is $CH_3$ or $CH_2CH_3$ oxidizing the compound of Formula (R)-D to provide a compound of Formula (R)-$D^{ox}$;

(R)-$D^{ox}$

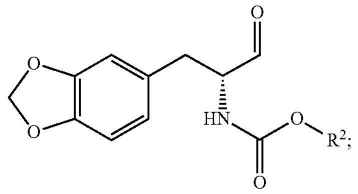

wherein $R^2$ is $CH_3$ or $CH_2CH_3$;

reacting the compound of Formula (R)-$D^{ox}$ with a methyl organometallic reagent to provide the compound of Formula (R)-D';

(R)-D'

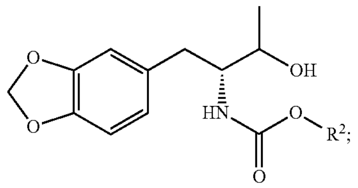

wherein $R^2$ is $CH_3$ or $CH_2CH_3$;

reacting the compound of Formula (R)-D' with a chlorinating agent to provide a compound of Formula (R)-E', respectively:

(R)-E'

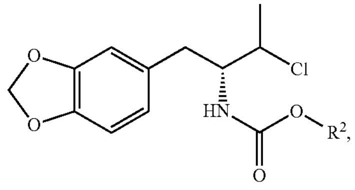

wherein $R^2$ is $CH_3$ or $CH_2CH_3$; and reacting the compound of Formula (R)-E' with a reducing agent to provide the (S)-MBDB.

Alternatively, the reacting the compound of Formula (R)-E' with a reducing agent to provide the compound of Formula (S)-I comprises:

reacting a compound of Formula (R)-E' with a first reducing agent to provide a compound of Formula (R)-F; and (R)-F

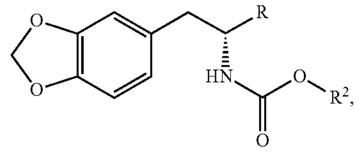

wherein

R is $CH_2CH_3$; and $R^2$ is $CH_3$ or $CH_2CH_3$; and reacting the compound of Formula (R)-F with a second reducing agent to provide the compound of Formula (R)-I or (S)-I.

In an exemplary embodiment of a process of the application, R is $CH_2CH_3$, $R^1$ and $R^2$ are each independently selected from $CH_3$ and $CH_2CH_3$ and the application includes a process for preparing (R)—N-methyl-1,3-benzodioxolylbutanamine ((R)-MBDB)

(R)-MBDB

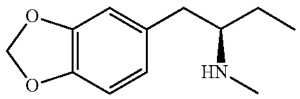

the process comprising:

protecting the amino group of 3,4-dihydroxy-L-phenylalanine (L-DOPA) $C_{1-4}$alkyl ester of Formula (S)-A:

(S)-A

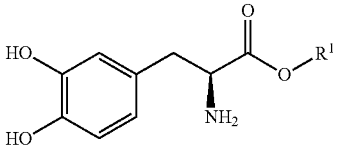

wherein $R^1$ is $CH_3$ or $CH_2CH_3$, with a $C_{1-4}$alkoxycarbonyl protecting group or a benzyloxy carbonyl protecting group to provide a compound of Formula (S)-B (S)-B

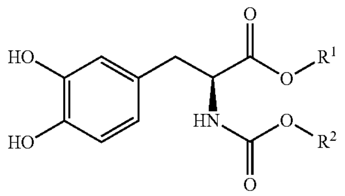

wherein
$R^1$ is $CH_3$ or $CH_2CH_3$; and
$R^2$ is $CH_3$ or $CH_2CH_3$;

cyclizing the compound of Formula (S)-B to provide a compound of Formula (S)-C:

(S)-C

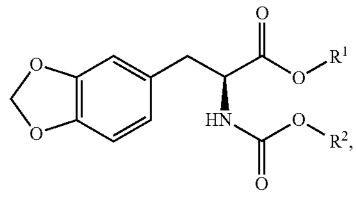

wherein
$R^1$ is $CH_3$ or $CH_2CH_3$; and
$R^2$ is $CH_3$ or $CH_2CH_3$;

hydrolyzing the compound of Formula (S)-C to provide the compound of Formula (S)-C';

(S)-C'

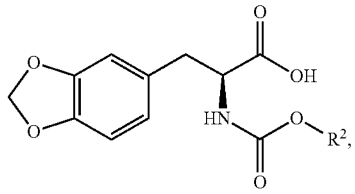

wherein $R^2$ is $CH_3$ or $CH_2CH_3$;

converting the compound of Formula (S)-C' to the compound of Formula (S)-E"

(S)-E"

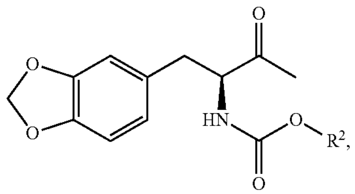

wherein $R^2$ is $CH_3$ or $CH_2CH_3$; and reacting the compound of Formula (S)-E" with a reducing agent to provide the (R)-MBDB.

In some embodiments, the step of converting the compound of Formula (S)-C' to the compound of Formula (S)-E" comprises;

reacting the compound of Formula (S)-C' with N,O-dimethylhydroxylamine,

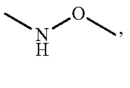

to provide the amide compound of Formula (S)-E""

(S)-E'''

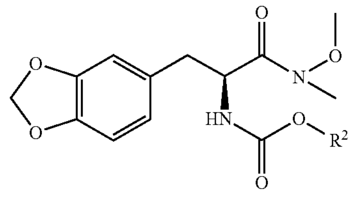

wherein $R^2$ is $CH_3$ or $CH_2CH_3$; and reacting the compound of Formula (S)-E"" with a methyl organometallic reagent to provide the compound of Formula (S)-E"

(S)-E"

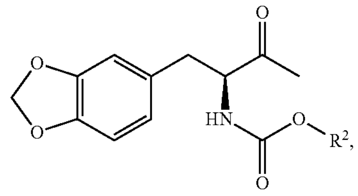

wherein $R^2$ is $CH_3$ or $CH_2CH_3$.

In an exemplary embodiment of a process of the application, R is $CH_2CH_3$, $R^1$ and $R^2$ are each independently selected from $CH_3$ and $CH_2CH_3$ and the application includes a process for preparing (S)—N-methyl-1,3-benzodioxolylbutanamine ((S)-MBDB)

(S)-MBDB

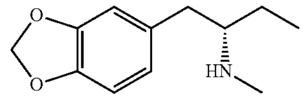

the process comprising:

protecting the amino group of 3,4-dihydroxy-L-phenylalanine (L-DOPA) $C_{1-4}$alkyl ester of Formula (R)-A:

(R)-A

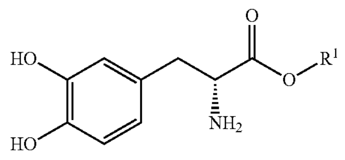

wherein $R^1$ is $CH_3$ or $CH_2CH_3$, with a $C_{1-4}$alkoxycarbonyl protecting group or a benzyloxy carbonyl protecting group to provide a compound of Formula (R)-B, respectively:

(R)-B

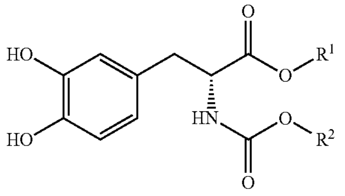

wherein
$R^1$ is $CH_3$ or $CH_2CH_3$; and
$R^2$ is $CH_3$ or $CH_2CH_3$;

cyclizing the compound of Formula (R)-B to provide a compound of Formula (R)-C, respectively:

(R)-C

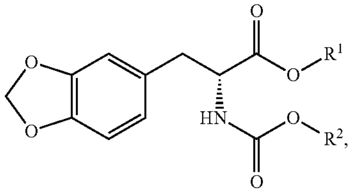

wherein
$R^1$ is $CH_3$ or $CH_2CH_3$; and
$R^2$ is $CH_3$ or $CH_2CH_3$;

hydrolyzing the compound of Formula (R)-C to provide the compound of Formula (R)-C';

(R)-C'

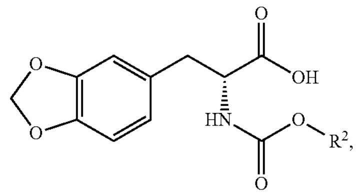

wherein $R^2$ is $CH_3$ or $CH_2CH_3$;

converting the compound of Formula (R)-C' to the compound of Formula (R)-E"

(R)-E"

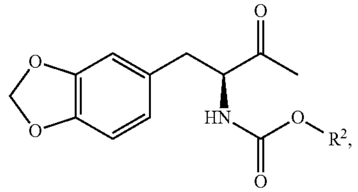

wherein $R^2$ is $CH_3$ or $CH_2CH_3$; and reacting the compound of Formula (R)-E" with a reducing agent to provide the (S)-MBDB.

In some embodiments, the step of converting the compound of Formula (S)-C' or (R)-C' to the compound of Formula (R)-E" comprises;

reacting the compound of Formula (R)-C' with N,O-dimethylhydroxylamine,

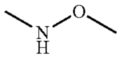

to provide the amide compound of Formula (R)-E"", respectively (R)-E'''

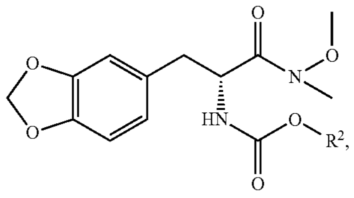

wherein $R^2$ is $CH_3$ or $CH_2CH_3$; and reacting the compound of (R)-E" with a methyl organometallic reagent to provide the compound of Formula (R)-E", respectively (R)-E"

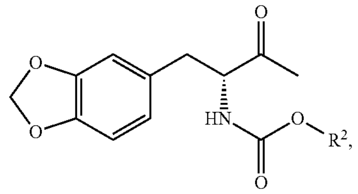

wherein $R^2$ is $CH_3$ or $CH_2CH_3$.

In some embodiments, in the exemplary embodiment of a process of the application, the first reducing agent is tributyltin hydride or a palladium catalyst, and the second reducing reagent is lithium aluminium hydride.

In some embodiments, the compound of Formula (R)-I or (S)-I prepared by a process of the application is further converted to a salt, solvate and/or prodrug thereof, for example, a pharmaceutically acceptable salt, solvate and/or prodrug thereof. In some embodiments, the (R)-MDMA or (S)-MDMA prepared by a process of the application is further converted to a salt, solvate and/or prodrug thereof, for example, a pharmaceutically acceptable salt, solvate and/or prodrug thereof. In some embodiments, the (R)-MBDB or (S)-MBDB prepared by a process of the application is further converted to a salt, solvate and/or prodrug thereof, for example, a pharmaceutically acceptable salt, solvate and/or prodrug thereof.

In some embodiments the pharmaceutically acceptable salt is an acid addition salt and the selection of a suitable salt may be made by a person skilled in the art (see, for example, S. M. Berge, et al., “Pharmaceutical Salts,” J. Pharm. Sci. 1977, 66, 1-19).

An acid addition salt that is pharmaceutically acceptable, that is suitable for, or compatible with, the treatment of subjects, is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

In some embodiments, the compound of Formula (R)-I or (S)-I is reacted with hydrochloric acid to provide the hydrochloride salt of the compound of Formula (R)-I or (S)-I, respectively. In some embodiments, the (R)- or (S)-MDMA, is reacted with hydrochloric acid to provide the hydrochloride salt of (R)- or (S)-MDMA, respectively (i.e., (R)-MDMA·HCl or (S)-MDMA·HCl). In some embodiments, the (R)- or (S)-MBDB is reacted with hydrochloric acid to provide the hydrochloride salt of (R)-MBDB ((R)-MBDB·HCl) or (S)-MBDB ((S)-MBDB·HCl).

Solvates of the compounds of Formula (R)-I or (S)-I include, for example, those made with solvents that are pharmaceutically acceptable. Examples of such solvents include water (resulting solvate is called a hydrate) and ethanol and the like. Suitable solvents are physiologically tolerable at the dosage administered.

The formation of a desired compound salt is achieved using standard techniques. For example, the neutral compound is treated with an acid in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs may be, for example, conventional esters formed with the available amino group. Some common esters which have been utilized as prodrugs are phenyl esters, aliphatic ($C_1$-$C_{24}$) esters, acyloxymethyl esters, carbamates and amino acid esters.

Examples of inert solvents include, but are not limited to, benzene, toluene, tetrahydrofuran, ethyl ether, ethyl acetate, dimethyl formamide (DMF), acetonitrile, $C_{1-6}$alkylOH (e.g. methanol, ethanol, n-propanol, 2-propanol, n-butanol, butan-2-ol and 2-methyl-1-propanol), diethylcarbonate, hexane and dimethylsulfoxide (DMSO). Further examples can include aqueous solutions, such as water and dilute acids and bases, and ionic liquids, provided that such solvents do not interfere with the reaction.

III. Compounds of the Application

The present application also includes compound of Formula (S)-C, (R)-C, (S)-C', (R)-C', (S)-D, (R)-D, (S)-D$^{ox}$, (R)-D$^{ox}$, (S)-D', (R)-D', (S)-E, (R)-E, (S)-E', (R)-E', (S)-E'', (R)-E'' (S)-E and (R)-E'''' useful for the preparation of the compounds of Formula (R)-I or (S)-I. In some embodiments, the present application also includes compounds of Formula (S)-C, (R)-C, (S)-D, (R)-D, (S)-E and (R)-E, useful for the preparation of (R)-MDMA or (S)-MDMA. In some embodiments, the present application also includes compounds of Formula (S)-C, (R)-C, (S)-C', (R)-C', (S)-D$^{ox}$, (R)-D$^{ox}$, (S)-D', (R)-D', (S)-E', (R)-E', (S)-E'', (R)-E'', (S)-E'' and (R)-E useful for the preparation of (R)-MBDB or (S)-MBDB.

Accordingly, the present application includes a compound of Formula (S)-C:

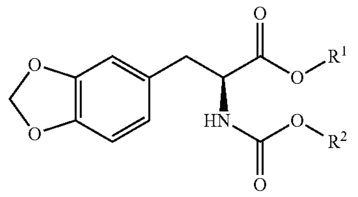
(S)-C wherein $R^1$ is $C_{1-4}$alkyl; and $R^2$ is $CH_3$ or $CH_2CH_3$.

The present application also includes a compound of Formula (R)-C:

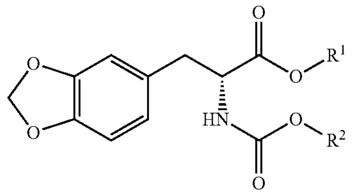
(R)-C wherein $R^1$ is $C_{1-4}$alkyl; and $R^2$ is $CH_3$ or $CH_2CH_3$.

In an embodiment, $R^1$ in the compounds of Formula (S)-C or (R)-C is $CH_3$ or $CH_2CH_3$. In an embodiment, $R^1$ in the compounds of Formula (S)-C or (R)-C is $CH_3$.

In an exemplary embodiment, the present application includes a compound of Formula (S)-C wherein $R^1$ and $R^2$ are both $CH_3$ and the compound of Formula (S)-C has the following structure:

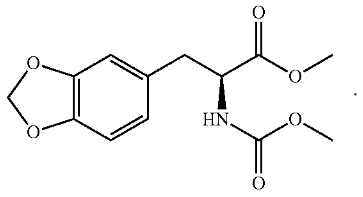 [SMILES: COC(=O)N[C@@H](Cc1ccc2c(c1)OCO2)C(=O)OC]

In an exemplary embodiment, the present application includes a compound of Formula (S)-C wherein $R^1$ and $R^2$ are both $CH_3$ and the compound of Formula (S)-C has the following structure:

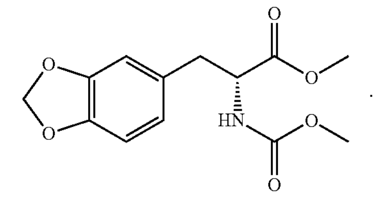 [SMILES: COC(=O)N[C@H](Cc1ccc2c(c1)OCO2)C(=O)OC]

The present application also includes a compound of Formula (S)-C':

(S)-C'

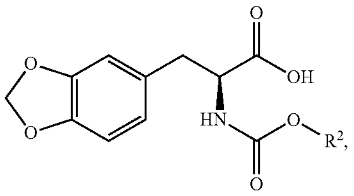

wherein $R^2$ is $CH_3$.

The present application also includes a compound of Formula (R)-C':

(R)-C'

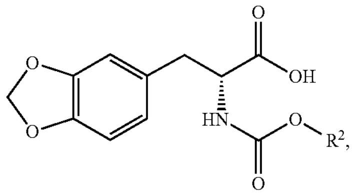

wherein $R^2$ is $CH_3$.

The present application further includes a compound of Formula (S)-D:

(S)-D

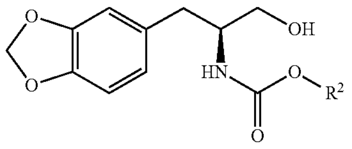

wherein $R^2$ is $CH_3$, $CH_2CH_3$ or $CH_2Ph$.

The present application further includes a compound of Formula (R)-D:

(R)-D

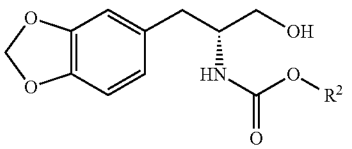

wherein $R^2$ is $CH_3$, $CH_2CH_3$ or $CH_2Ph$.

In some embodiments, $R^2$ in the compounds of Formula (S)-D or (R)-D is $CH_3$ or $CH_2CH_3$. In an embodiment, $R^2$ in the compounds of Formula (S)-D or (R)-D is $CH_3$.

In an exemplary embodiment, the present application includes a compound of Formula (S)-D wherein $R^2$ is $CH_3$ and the compound of Formula (S)-D has the following structure:

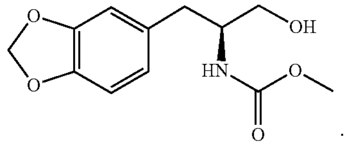 [SMILES: COC(=O)N[C@H](CO)Cc1ccc2c(c1)OCO2]

In an exemplary embodiment, the present application includes a compound of Formula (R)-D wherein $R^2$ is $CH_3$ and the compound of Formula (R)-D has the following structure:

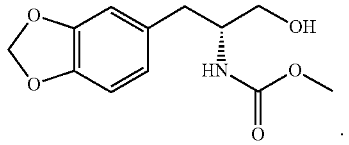 [SMILES: COC(=O)N[C@@H](CO)Cc1ccc2c(c1)OCO2]

The present application also includes a compound of Formula (S)-D';

(S)-D'

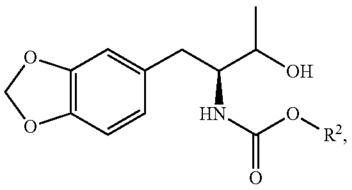

wherein $R^2$ is $CH_3$, $CH_2CH_3$ or $C(CH_3)_3$.

The present application also includes a compound of Formula (R)-D';

(R)-D'

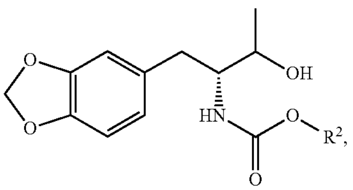

wherein $R^2$ is $CH_3$, $CH_2CH_3$ or $C(CH_3)_3$.

In some embodiments, $R^2$ in the compounds of Formula (S)-D' or (R)-D' is $CH_3$ or $CH_2CH_3$. In an embodiment, $R^2$ in the compounds of Formula (S)-D' or (R)-D' is $CH_3$.

The present application also includes a compound of Formula (S)-$D^{ox}$;

(S)-$D^{ox}$

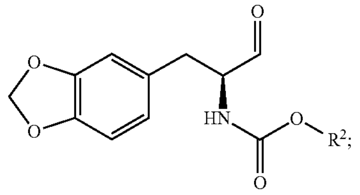

wherein $R^2$ is $CH_3$ (R)-$D^{ox}$

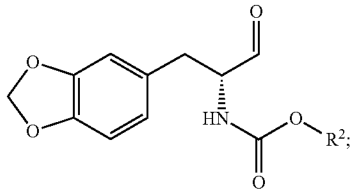

The present application also includes a compound of Formula (R)-$D^{ox}$;

(S)- E

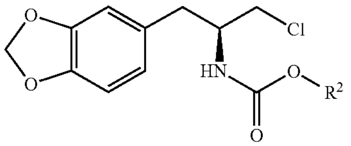

wherein $R^2$ is $CH_3$, $CH_2CH_3$ or $CH_2Ph$.

The present application also includes a compound of Formula (R)-E (R)-E

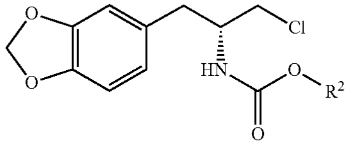

wherein $R^2$ is $CH_3$, $CH_2CH_3$ or $CH_2Ph$.

In some embodiments, $R^2$ in the compounds of Formula (S)-E or (R)-E is $CH_3$ or $CH_2CH_3$. In an embodiment, $R^2$ in the compounds of Formula (S)-E or (R)-E is $CH_3$.

In an exemplary embodiment, the present application includes a compound of Formula (S)-E wherein $R^2$ is $CH_3$ and the compound of Formula (S)-E has the following structure:

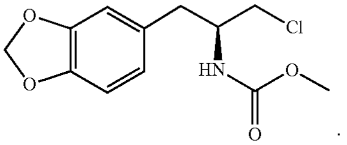

In an exemplary embodiment, the present application includes a compound of Formula (R)-E wherein $R^2$ is $CH_3$ and the compound of Formula (R)-E has the following structure:

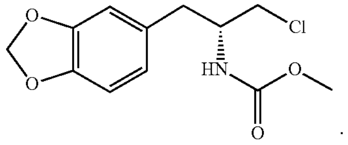 [SMILES: COC(=O)N[C@@H](CCl)Cc1ccc2c(c1)OCO2]

The present application also includes a compound of Formula (S)-E'

(S)-E'

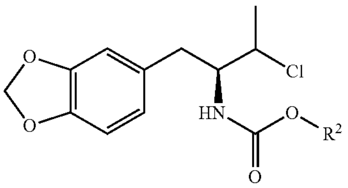

wherein $R^2$ is $CH_3$.

The present application also includes a compound of Formula (R)-E'

(R)-E'

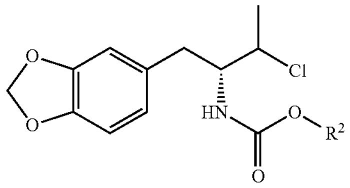

wherein $R^2$ is $CH_3$.

The present application also includes a compound of Formula (S)-E"

(S)-E"

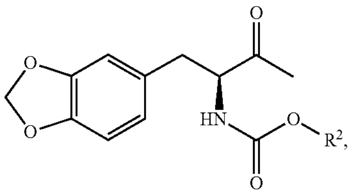

wherein $R^2$ is $CH_3$.

The present application also includes a compound of Formula (R)-E"

(R)-E''

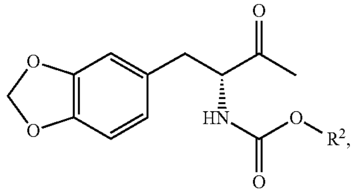

wherein $R^2$ is $CH_3$.

The present application also includes a compound of Formula (S)-E (S)-E'''

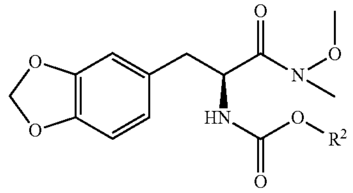

wherein $R^2$ is $CH_3$.

The present application also includes a compound of Formula (R)-E''

(R)-E'''

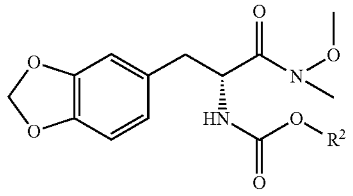

wherein $R^2$ is $CH_3$.

The present application also includes a compound of Formula (S)-F:

(S)-F

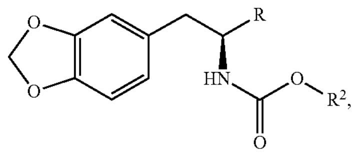

wherein R is $CH_3$ or $CH_2CH_3$; and $R^2$ is $CH_3$ or $CH_2Ph$.

The present application also includes a compound of Formula (R)-F:

(R)-F

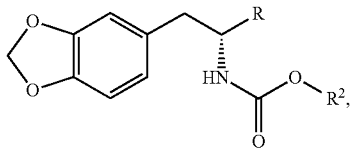

wherein R is $CH_3$ or $CH_2CH_3$; and $R^2$ is $CH_3$ or $CH_2Ph$.

In some embodiments, $R^2$ in the compounds of Formula (S)-F or (R)-F is $CH_3$. In some embodiments, $R^2$ in the compounds of Formula (S)-F or (R)-F is $CH_2Ph$.

As the process of the application provides (R)-MDMA or (S)-MDMA, for example, when R is $CH_3$ in the compound of Formula (R)-I or (S)-I, respectively, the application also includes (R)-MDMA or (S)-MDMA prepared by a process of the application as described above.

In some embodiments, (R)-MDMA or (S)-MDMA prepared by a process of the application as described above is reacted with hydrochloric acid to provide the hydrochloride salt of (R)-MDMA ((S)-MDMA·HCl) or (S)-MDMA ((S)-MDMA·HCl), respectively.

As the process of the application provides (R)-MBDB or (S)-MBDB, for example, when R is $CH_2CH_3$ in the compound of Formula (R)-I or (S)-I, the application also includes (R)-MBDB or (S)-MBDB prepared by a process of the application as described above.

In some embodiments, (R)-MBDB or (S)-MBDB prepared by a process of the application as described above is reacted with hydrochloric acid to provide the hydrochloride salt of (R)-MBDB ((R)-MBDB·HCl) or (S)-MBDB ((S)-MBDB·HCl), respectively.

EXAMPLES

The following non-limiting examples are illustrative of the present application.

Example 1. Exemplary Process for Preparing (R)-MDMA (R)-MDMA can be prepared according to the following synthetic scheme.

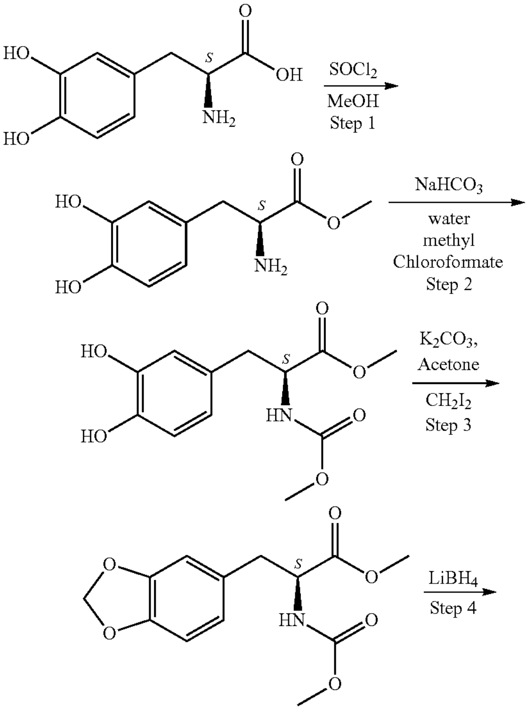

-continued

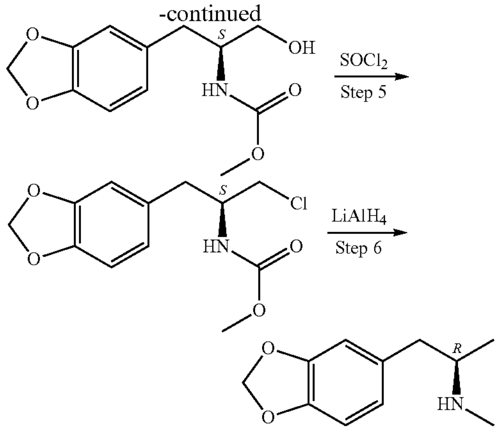

Steps 1 and 2

To a 0° C. stirred suspension of L-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound Step 4

To a cold (5° C.) solution of the product of step 3 (158.3 g, 0.563 mole) in 1.1 L of THF is added a slight excess of (15 g, 0.689 mole) of lithium borohydride in portions over a period of 20 min. The mixture is stirred at 8-10° C. for 20 min and then at 25° C. for 3 h under argon. The mixture is cautiously diluted with water, stirred for 5 min, 1.0 L of ethyl acetate is added and stirred for 1 h. The layers are separated and the aqueous layer is extracted with ethyl acetate. The combined ethyl acetate extracts are washed with brine, dried over anhydrous sodium sulfate, filtered and the filtrate is evaporated to dryness to yield a solid. The solid is recrystallized from ethyl acetate-hexane to give the title compound.

Step 5

To a solution of the product of step 4 (0.57 g, 2.25 mmol) in dry THF (20 ml) at 0° C. is added thionyl chloride (0.536 g, 4.5 mmol) and the resulting reaction mixture is stirred well at room temperature (RT) for 16 h. Then the reaction mixture is concentrated in vacuo to provide the title compound.

Step 6

To a stirred suspension $LiAlH_4$ (0.77 g, 20.4 mmol) in THF (120 mL) is added a solution of the product of Step 5 (2.22 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 2. Exemplary Process for Preparing (S)-MDMA (S)-MDMA can be prepared according to the following synthetic scheme.

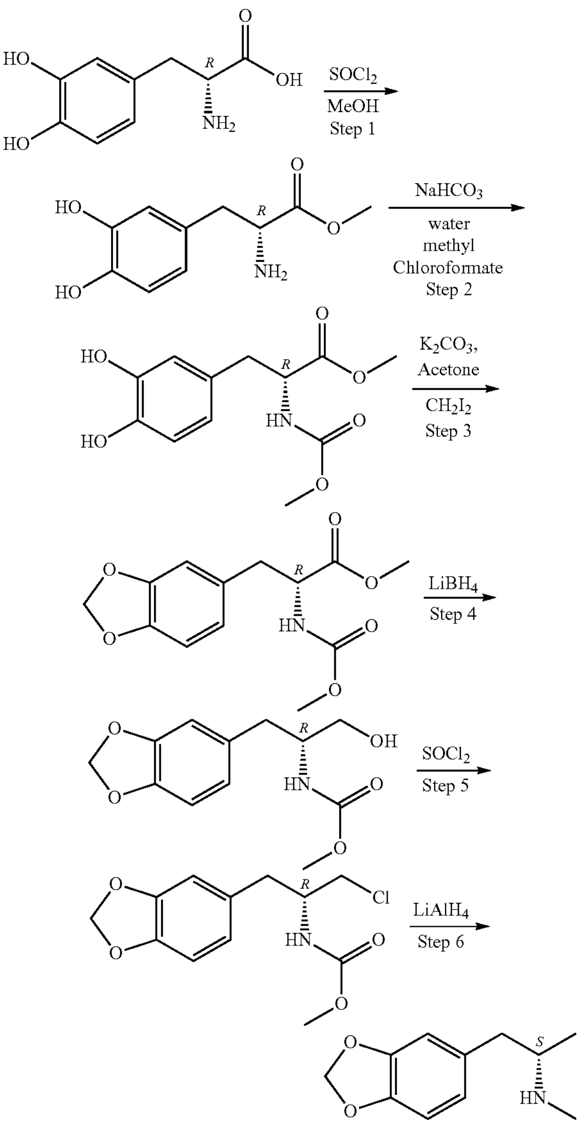

Steps 1 and 2

To a 0° C. stirred suspension of D-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound Step 4

To a cold (5° C.) solution of the product of step 3 (158.3 g, 0.563 mole) in 1.1 L of THF is added a slight excess of (15 g, 0.689 mole) of lithium aluminum hydride in portions over a period of 20 min. The mixture is stirred at 8-10° C. for 20 min and then at 25° C. for 3 h under argon. The mixture is cautiously diluted with water, stirred for 5 min, 1.0 L of ethyl acetate is added and stirred for 1 h. The layers are separated and the aqueous layer is extracted with ethyl acetate. The combined ethyl acetate extracts are washed with brine, dried over anhydrous sodium sulfate, filtered and the filtrate is evaporated to dryness to yield a solid. The solid is recrystallized from ethyl acetate-hexane to give the title compound.

Step 5

To a solution of the product of step 4 (0.57 g, 2.25 mmol) in dry THF (20 ml) at 0° C. is added thionyl chloride (0.536 g, 4.5 mmol) and the resulting reaction mixture is stirred well at room temperature (RT) for 16 h. Then the reaction mixture is concentrated in vacuo to provide the title compound.

Step 6

To a stirred suspension $LiAlH_4$ (0.77 g, 20.4 mmol) in THF (120 mL) is added a solution of the product of Step 5 (2.22 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 3. Exemplary Process for Preparing (R)-MBDB (R)-MBDB can be prepared according to the following synthetic scheme.

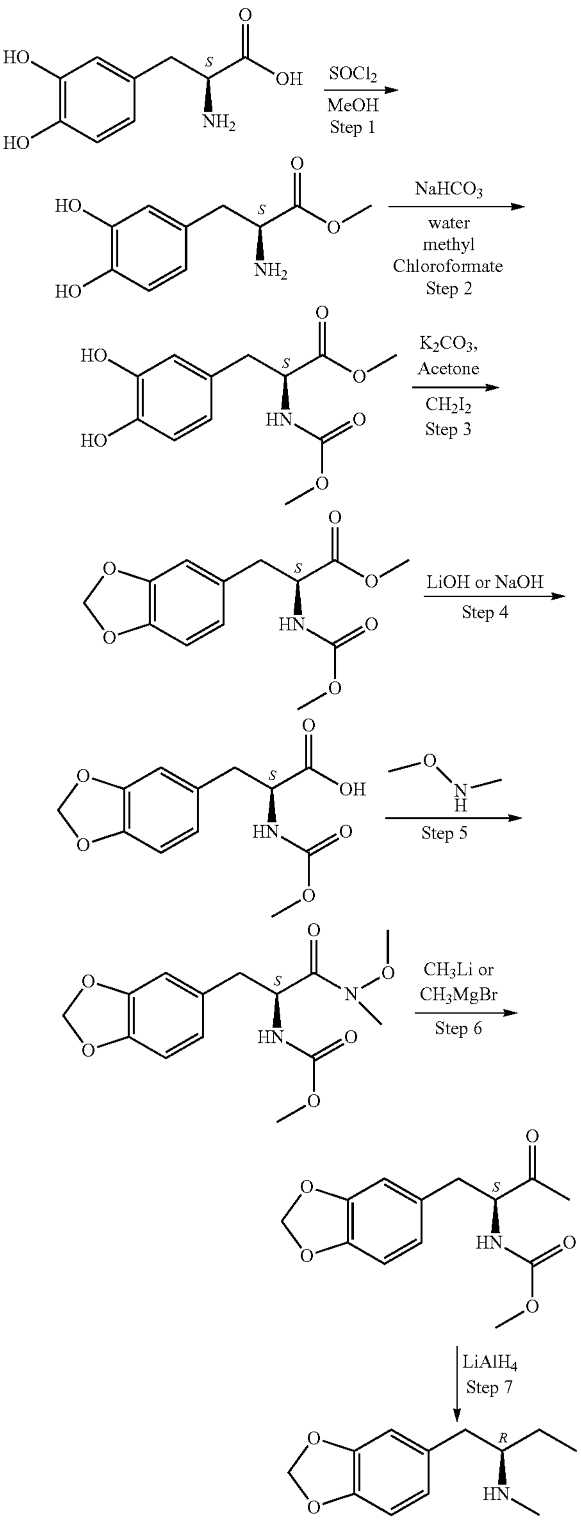

Steps 1 and 2

To a 0° C. stirred suspension of L-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound.

Step 4

To a solution of the product of Step 3 (20.25 g, 72 mmol) in methanol (250 mL) is added 1N aqueous NaOH (72 mL). The mixture is stirred at room temperature for 4 hours. Then it is evaporated to remove most of the solvent. The resulting mixture is diluted with water (150 mL) and acidified by the addition of 2N aqueous HCl. The solution is then extracted with portions of ethyl acetate (3×150 mL). The combined organic extracts are washed with water (2×100 mL) and dried over anhydrous sodium sulfate, and concentrated to give the title compound Step 5

To a solution of the product of Step 4 (2.67 g, 10 mmol), NH(Me) OMe HCl (1.46 g, 15 mmol) and HBTU (5.69 g, 15 mmol) in DCM (35 mL) is added DIPEA (5.80 g, 45 mmol). The mixture is stirred at room temperature for 2 h until TLC showed completion of reaction. The solvent is evaporated under reduced pressure and the residue was resuspended in ethyl acetate. The organic layer is washed with 1 M HCl (3×), saturated $NaHCO_3$ (2×), brine, and then dried using anhydrous sodium sulfate. It is evaporated under reduced pressure and the crude product was purified by column chromatography to give the title Weinreb amide compound Step 6

A 100 ml round bottom flask containing a magnetic Stirring bar is charged with the Weinreb amide (the product of Step 5) (1.24 g, 4 mmol) and THF (30 ml). The solution was cooled to −78° C. in a dry ice-acetone bath. The MeLi (7 ml of 1.4M ether solution, 10 mmol) is then added via Syringe. The dry ice bath is replaced by an ice bath and the clear, virtually colorless solution stirred for 1 hour. The ice-cold solution is poured into 100 ml of ice cold 5% citric acid and extracted with EtOAc (150 ml), washed with 5% citric acid (1×20 ml), brine (2×20 ml), dried with $Na_2SO_4$, filtered, and the solvent removed on a rotary evaporator and then vacuum pump according Step 7

To a stirred suspension $LiAlH_4$ (0.77 g, 20.4 mmol) in THF (120 mL) is added a solution of the product of Step 6 (2.22 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 4. Exemplary Process for Preparing (S)-MBDB (S)-MBDB can be prepared according to the following synthetic scheme.

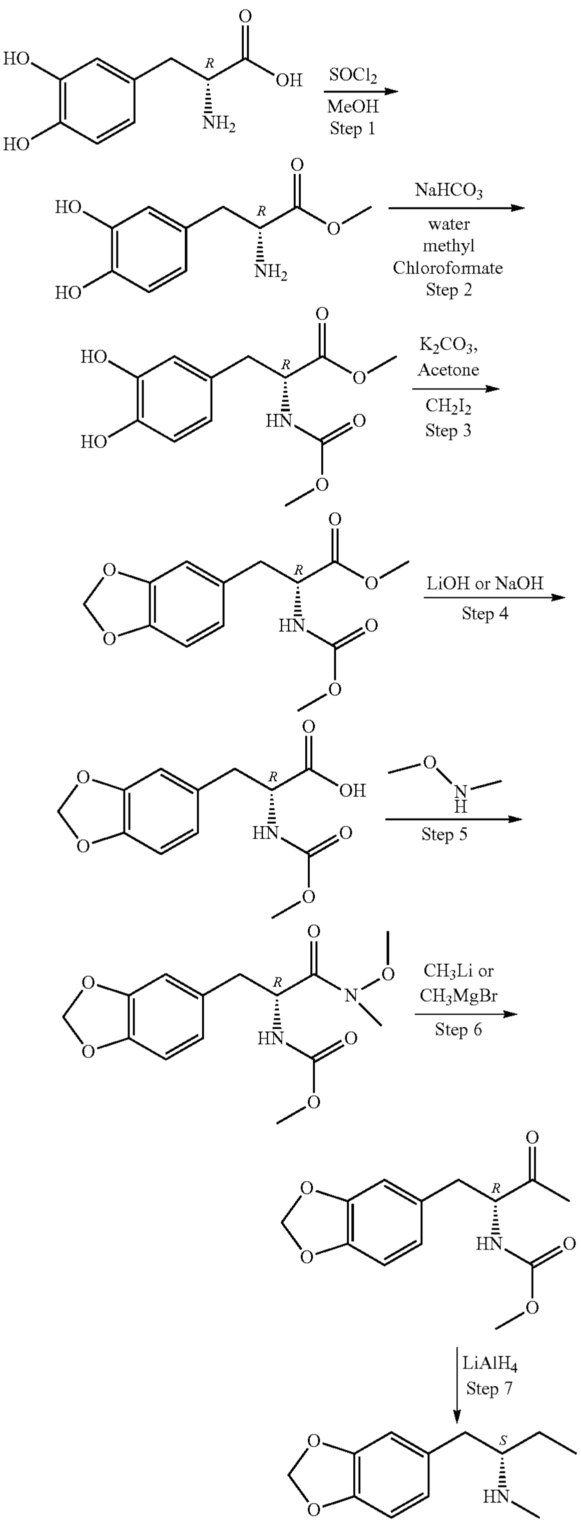

Steps 1 and 2

To a 0° C. stirred suspension of L-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound.

Step 4

To a solution of the product of Step 3 (20.25 g, 72 mmol) in methanol (250 mL) is added 1N aqueous NaOH (72 mL). The mixture is stirred at room temperature for 4 hours. Then it is evaporated to remove most of the solvent. The resulting mixture is diluted with water (150 mL) and acidified by the addition of 2N aqueous HCl. The solution is then extracted with portions of ethyl acetate (3×150 mL). The combined organic extracts are washed with water (2×100 mL) and dried over anhydrous sodium sulfate, and concentrated to give the title compound Step 5

To a solution of the product of Step 4 (2.67 g, 10 mmol), NH(Me) OMe HCl (1.46 g, 15 mmol) and HBTU (5.69 g, 15 mmol) in DCM (35 mL) is added DIPEA (5.80 g, 45 mmol). The mixture is stirred at room temperature for 2 h until TLC showed completion of reaction. The solvent is evaporated under reduced pressure and the residue was resuspended in ethyl acetate. The organic layer is washed with 1 M HCl (3×), saturated $NaHCO_3$ (2×), brine, and then dried using anhydrous sodium sulfate. It is evaporated under reduced pressure and the crude product was purified by column chromatography to give the title Weinreb amide compound Step 6

A 100 ml round bottom flask containing a magnetic Stirring bar is charged with the Weinreb amide (the product of Step 5) (1.24 g, 4 mmol) and THF (30 ml). The solution was cooled to −78° C. in a dry ice-acetone bath. The MeLi (7 ml of 1.4M ether solution, 10 mmol) is then added via Syringe. The dry ice bath is replaced by an ice bath and the clear, virtually colorless solution stirred for 1 hour. The ice-cold solution is poured into 100 ml of ice cold 5% citric acid and extracted with EtOAc (150 ml), washed with 5% citric acid (1×20 ml), brine (2×20 ml), dried with $Na_2SO_4$, filtered, and the solvent removed on a rotary evaporator and then vacuum pump according Step 7

To a stirred suspension $LiAlH_4$ (0.77 g, 20.4 mmol) in THF (120 mL) is added a solution of the product of Step 6 (2.22 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 5. Exemplary Process for Preparing (R)-MBDB (R)-MBDB can be prepared according to the following synthetic scheme.

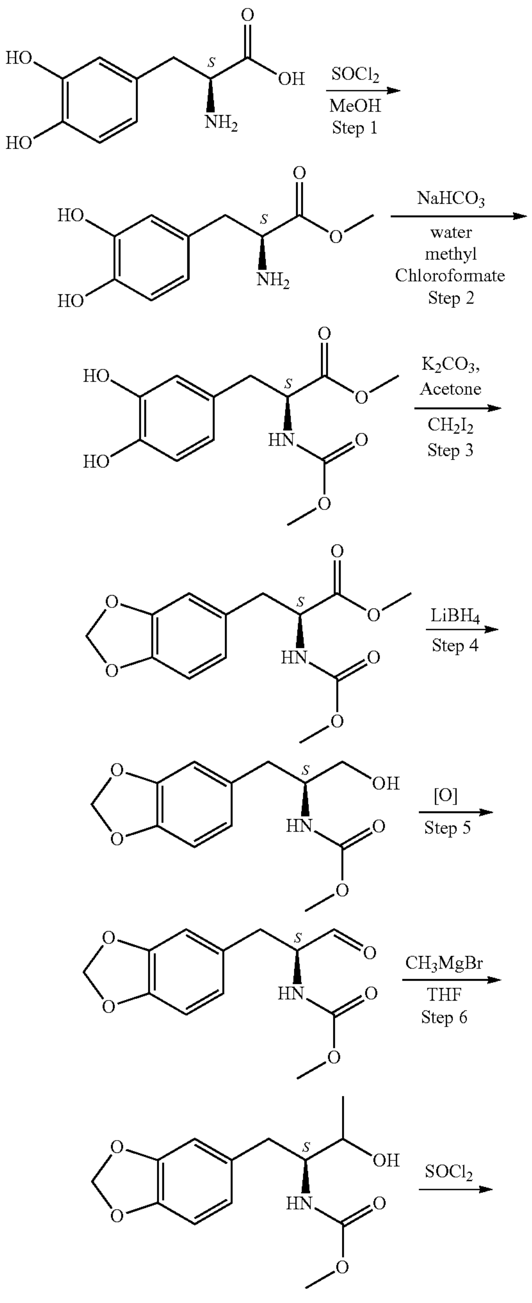

-continued

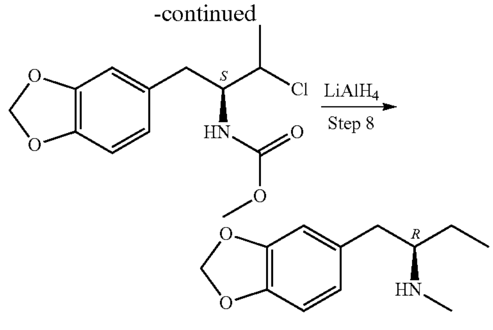

Steps 1 and 2

To a 0° C. stirred suspension of L-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound Step 4

To a cold (5° C.) solution of the product of step 3 (158.3 g, 0.563 mole) in 1.1 L of THF is added a slight excess of (15 g, 0.689 mole) of lithium borohydride in portions over a period of 20 min. The mixture is stirred at 8-10° C. for 20 min and then at 25° C. for 3 h under argon. The mixture is cautiously diluted with water, stirred for 5 min, 1.0 L of ethyl acetate is added and stirred for 1 h. The layers are separated and the aqueous layer is extracted with ethyl acetate. The combined ethyl acetate extracts are washed with brine, dried over anhydrous sodium sulfate, filtered and the filtrate is evaporated to dryness to yield a solid. The solid is recrystallized from ethyl acetate-hexane to give the title compound.

Step 5

Method 1: Dess-Martin Periodinane

Dess-Martin periodinane 29.7 g (70.0 mmol) are suspended in 150 ml dichloromethane, then within 40 minutes a solution of the product of Step 4 (16.13 g, 63.7 mmol) in 150 ml dichloromethane was added in. The reaction solution is stirred for 2 hours at ambient temperature, then combined with 200 ml 20% $KHCO_3$ solution and 200 ml 10% $Na_2S_2O_3$ solution. The mixture is stirred for 20 min at ambient temperature, the two phases are separated and the organic phase is washed with 20% $KHCO_3$ solution and water, dried over $Na_2SO_4$ and evaporated to dryness using the rotary evaporator to give the title compound.

Method 2: Swern Oxidation

Oxalyl chloride (8.2 g, 65 mmol, 1.2 equiv.) is dissolved in $CH_2Cl_2$ (125 mL). The mixture is cooled to −60° C. DMSO (9.3 g, 119 mmol, 2.2 equiv.) in $CH_2Cl_2$ (25 mL) is added dropwise over ten minutes. The reaction mixture is stirred for ten minutes after which the product of Step 4 (13.7 g, 54 mmol, 1 equiv.) in $CH_2Cl_2$ (125 mL) is added dropwise over 15 minutes. After stirring for 30 minutes, DIPEA (27.9 g, 216 mmol, 4 equiv.) is added over 15 minutes. The reaction mixture is stirred at −60° C. for 30 minutes before being allowed to warm to room temperature. The reaction mixture is washed with 5% aqueous hydrochloric acid solution (3×75 mL). The combined aqueous layer is extracted with $CH_2Cl_2$. Combined organic layer is washed with water (3×75 mL) and brine (75 mL), dried over $Na_2SO_4$, filtered and concentrated in vacuo to give the title compound.

Method 3: TEMPO Oxidation

The product of Step 4 (25.12 g, 10 mmol), sodium bicarbonate (12.6 g, 15 mmol), sodium bromide (10.3 g, 1.0 eq.), TEMPO (1.56 g, 1.0 mmol) are mixed together in dichloromethane (300 ml) and water (100 ml). Then the temperature of the reaction mixture is lowered to below 5° C. Sodium hypochlorite solution (75 ml, 11 mmol) is added dropwise to control the internal temperature of the reaction solution not be higher than 5° C. After the addition is complete, the reaction solution is kept at 5° C. and stirred until the starting material is consumed. 10% sodium bisulfite solution (115 ml) is added and control the internal temperature not higher than 15° C. After the addition is complete, stir for 15 minutes, and let stand to separate. The aqueous layer is extracted with dichloromethane (50 ml×2), the organic layers are combined, washed with saturated brine, and dried over anhydrous sodium sulfate, filtered and concentrated under reduced pressure to give the title compound.

Step 6

A solution of MeMgBr (0.97 ml, 3M in diethyl ether is added dropwise to a solution of the step 5 (324 mg, 1.29 mmol) in THF at −78° C. The resulting reaction mixture is warmed up to 0° C. and stirred at this temperature for 30 min. The reaction is quenched with saturated $NH_4Cl$ aqueous solution and the organic layer is separated, dried ($Na_2SO_4$) and concentrated. The residue was purified by flash column chromatography on silica gel (2:1 hexane/EtOAc) to give the title compound.

Step 7

To a solution of the product of step 6 (0.601 g, 2.25 mmol) in dry THF (20 ml) at 0° C. is added thionyl chloride (0.536 g, 4.5 mmol) and the resulting reaction mixture is stirred well at room temperature (RT) for 16 h. Then the reaction mixture is concentrated in vacuo to provide the title compound.

Step 8

To a stirred suspension $LiAlH_4$ (0.77 g, 20.4 mmol) in THF (120 mL) is added a solution of the product of Step 7 (2.914 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 6. Exemplary Process for Preparing (S)-MBDB (S)-MBDB can be prepared according to the following synthetic scheme.

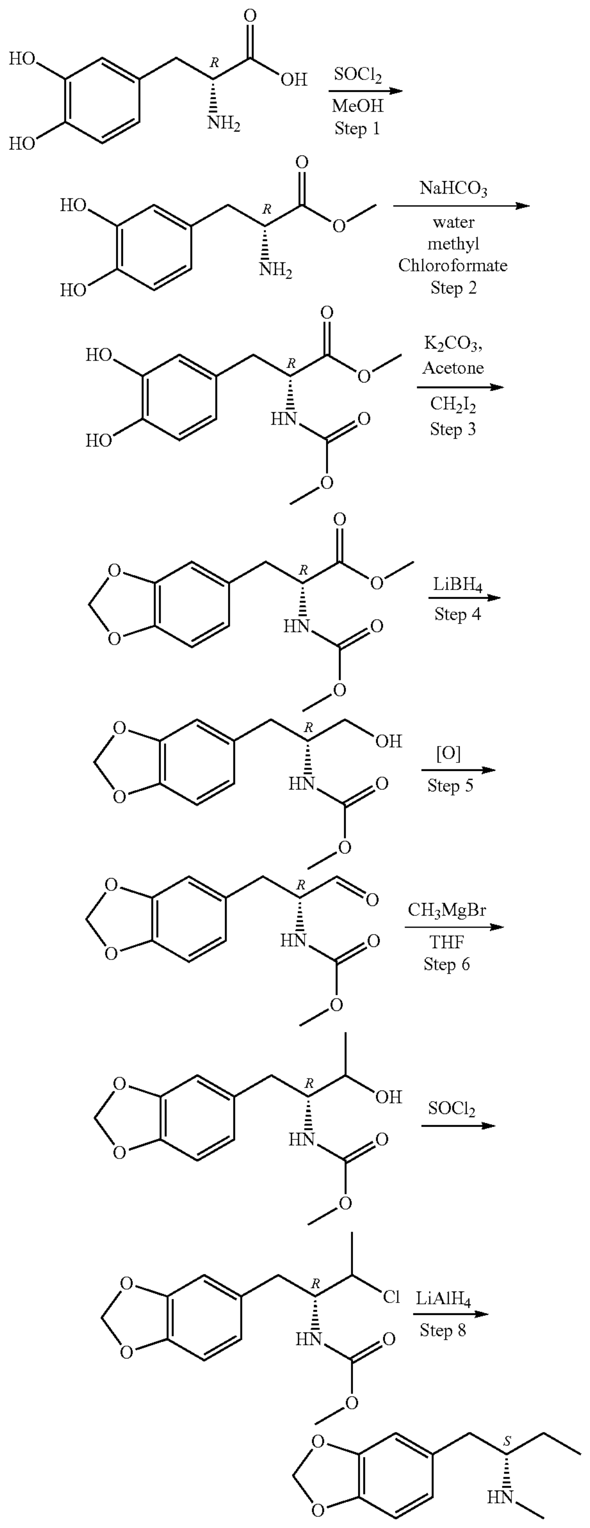

Steps 1 and 2

To a 0° C. stirred suspension of D-dopa (7.6 mmol) in dry MeOH (40.0 mL) is added excess thionyl chloride (13.7 mmol) dropwise. After 15 min, the mixture is refluxed for 24 hours, then solvent is removed by Rotavapor and the resulting solid is dried for 3 hours under high vacuum. The solid is dissolved in water (50 mL), and $NaHCO_3$ (1.27 g, 15.2 mmol) and methyl chloroformate (0.862 g, 9.12 mmol) dissolved in THF (20 mL) are successively added. The reaction mixture is stirred for 24 hours. The volatiles are evaporated, and the aqueous phase is extracted with EtOAc (3×15 mL). The combined organic phases are washed with water, 5% aqueous HCl and brine, dried over anhydrous $Na_2SO_4$ and concentrated in vacuo, affording the title compound.

Step 3

The product of Step 2, 8.616 g (0.032 mol), 15.0 g of potassium carbonate, 10.3 g of diiodomethane (0.038 mol) and 200 ml of acetone are mixed together and heated to reflux for 6 hours or until TLC shows the reaction is complete. Potassium carbonate is removed by filtration, and the reaction mixture is evaporated to dryness. The reside is diluted with EtOAc. The organic solution is washed successively with 100 ml of water, brine and dried over anhydrous sodium sulfate. The solution is then concentrated and purified to give the title compound Step 4

To a cold (5° C.) solution of the product of step 3 (158.3 g, 0.563 mole) in 1.1 L of THF is added a slight excess of (15 g, 0.689 mole) of lithium borohydride in portions over a period of 20 min. The mixture is stirred at 8-10° C. for 20 min and then at 25° C. for 3 h under argon. The mixture is cautiously diluted with water, stirred for 5 min, 1.0 L of ethyl acetate is added and stirred for 1 h. The layers are separated and the aqueous layer is extracted with ethyl acetate. The combined ethyl acetate extracts are washed with brine, dried over anhydrous sodium sulfate, filtered and the filtrate is evaporated to dryness to yield a solid. The solid is recrystallized from ethyl acetate-hexane to give the title compound.

Step 5

Method 1: Dess-Martin Periodinane

Dess-Martin periodinane 29.7 g (70.0 mmol) are suspended in 150 ml dichloromethane, then within 40 minutes a solution of the product of Step 4 (16.13 g, 63.7 mmol) in 150 ml dichloromethane was added in. The reaction solution is stirred for 2 hours at ambient temperature, then combined with 200 ml 20% $KHCO_3$ solution and 200 ml 10% $Na_2S_2O_3$ solution. The mixture is stirred for 20 min at ambient temperature, the two phases are separated and the organic phase is washed with 20% $KHCO_3$ solution and water, dried over $Na_2SO_4$ and evaporated to dryness using the rotary evaporator to give the title compound.

Method 2: Swern Oxidation

Oxalyl chloride (8.2 g, 65 mmol, 1.2 equiv.) is dissolved in $CH_2Cl_2$ (125 mL). The mixture is cooled to −60° C. DMSO (9.3 g, 119 mmol, 2.2 equiv.) in $CH_2Cl_2$ (25 mL) is added dropwise over ten minutes. The reaction mixture is stirred for ten minutes after which the product of Step 4 (13.7 g, 54 mmol, 1 equiv.) in $CH_2Cl_2$ (125 mL) is added dropwise over 15 minutes. After stirring for 30 minutes, DIPEA (27.9 g, 216 mmol, 4 equiv.) is added over 15 minutes. The reaction mixture is stirred at −60° C. for 30 minutes before being allowed to warm to room temperature. The reaction mixture is washed with 5% aqueous hydrochloric acid solution (3×75 mL). The combined aqueous layer is extracted with $CH_2Cl_2$. Combined organic layer is washed with water (3×75 mL) and brine (75 mL), dried over $Na_2SO_4$, filtered and concentrated in vacuo to give the title compound.

Method 3: TEMPO Oxidation

The product of Step 4 (25.12 g, 10 mmol), sodium bicarbonate (12.6 g, 15 mmol), sodium bromide (10.3 g, 1.0 eq.), TEMPO (1.56 g, 1.0 mmol) are mixed together in dichloromethane (300 ml) and water (100 ml). Then the temperature of the reaction mixture is lowered to below 5° C. Sodium hypochlorite solution (75 ml, 11 mmol) is added dropwise to control the internal temperature of the reaction solution not be higher than 5° C. After the addition is complete, the reaction solution is kept at 5° C. and stirred until the starting material is consumed. 10% sodium bisulfite solution (115 ml) is added and control the internal temperature not higher than 15° C. After the addition is complete, stir for 15 minutes, and let stand to separate. The aqueous layer is extracted with dichloromethane (50 ml×2), the organic layers are combined, washed with saturated brine, and dried over anhydrous sodium sulfate, filtered and concentrated under reduced pressure to give the title compound.

Step 6

A solution of MeMgBr (0.97 ml, 3M in diethyl ether is added dropwise to a solution of the step 5 (324 mg, 1.29 mmol) in THF at −78° C. The resulting reaction mixture is warmed up to 0° C. and stirred at this temperature for 30 min. The reaction is quenched with saturated $NH_4Cl$ aqueous solution and the organic layer is separated, dried ($Na_2SO_4$) and concentrated. The residue was purified by flash column chromatography on silica gel (2:1 hexane/EtOAc) to give the title compound.

Step 7

To a solution of the product of step 6 (0.601 g, 2.25 mmol) in dry THF (20 ml) at 0° C. is added thionyl chloride (0.536 g, 4.5 mmol) and the resulting reaction mixture is stirred well at room temperature (RT) for 16 h. Then the reaction mixture is concentrated in vacuo to provide the title compound.

Step 8

To a stirred suspension $LiAlH_4$ (0.77 g, 20.4 mmol) in THF (120 mL) is added a solution of the product of Step 7 (2.914 g, 10.2 mmol) in THF (30.0 ml) dropwise at 0° C., and then the reaction mixture is heated at reflux for 2 hours. The mixture is cooled to 0° C., and is quenched by addition of ice (10.0 g), then 15% aqueous sodium hydroxide (10.0 mL) followed by water (5 mL). The lithium salts are collected by filtration and washed with EtOAc (200 mL). The filtrate is dried ($Na_2SO_4$), 4M HCl in dioxane (3.0 mL) is added and concentrated. The resulting solid is triturated or recrystallized by organic solvent to give the title compound as the HCl salt.

Example 7 Exemplary Process for Preparing (R)-MDMA (R)-MDMA was prepared according to the following synthetic scheme.

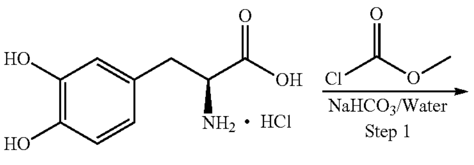

-continued

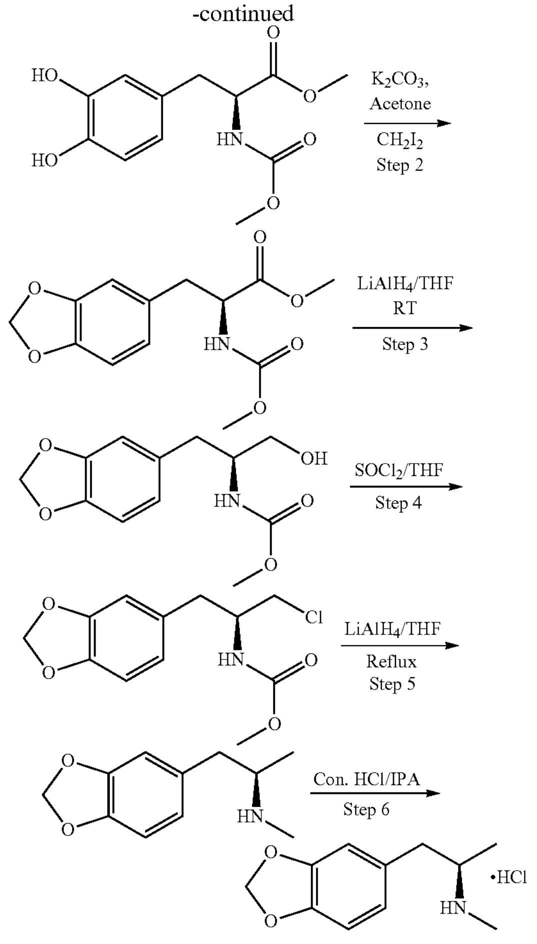

(R)-MDMA

Step 1

L-DOPA methyl ester (44.5 g; 0.180 mol; 1.0 Eq.) was added to a 3 L round bottom flask containing a large stir bar and dissolved in USP Purified Water (1000 mL). Sodium Bicarbonate (30.0 g; 0.360 mol; 2.0 Eq.) was added to the solution followed by the addition of a solution of methyl chloroformate (20.4 g; 0.216 mol; 1.2 Eq.) in THF (600 mL) via an additional funnel. The resulting mixture was then stirred at room temperature for at least 24 hours. The reaction was monitored for completion by TLC. The volatiles were evaporated, and the resulting aqueous phase was extracted with EtOAc (3×500 mL). The combined organic phases were washed with water (500 mL), 5% HCl (500 mL) and brine (500 mL), then dried over anhydrous $Na_2SO_4$ and concentrated in vacuo, affording 53.0 g (crude) product of step 1 as a clear oil.

1H-NMR (400 Hz, DMSO-$d_6$) δ (ppm): 8.75 (s, 1H), 8.70 (s, 1H), 7.58 (d, J=8.4 Hz, 1H), 6.61 (d, J=8.0 Hz, 1H), 6.59 (d, J=2.0 Hz, 1H), 6.45 (dd, J=8.0, 2.0 Hz, 1H), 4.14-4.08 (m, 1H), 3.60 (s, 3H), 3.49 (s, 3H), 2.82 (dd, J=12, 5.2 Hz, 1H) and 2.67 (dd, J=12, 9.6 Hz, 1H)

Step 2

The product of step 1 (53.0 g Crude; 0.180 mol; 1.0 Eq.) to a 3 L-3 necked was transferred to round bottom flask equipped with large stir bar, thermometer and condenser using Acetone (1400 mL). Potassium Carbonate (92.4 g; 0.669 mol; 3.7 Eq.) and Diiodomethane (116 g; 0.433 mol; 2.4 Eq.) are added to the solution of the product of step 1 and the reaction mixture was heated to reflux for 16 hours or until TLC shows the reaction is complete. Potassium Carbonate was removed by filtration and the filtrate was evaporated to dryness in vacuo. The resulting crude was purified by silica gel chromatography using a 0-10% Acetone/DCM gradient eluent to provide pure product of step 2 (20.8 g; 41%) as a white solid.

$^1$H-NMR (400 Hz, DMSO-$d_6$) d (ppm): 7.63 (d, J=8.4 Hz, 1H), 6.83 (d, J=1.2 Hz, 1H), 6.81 (d, J=1.2 Hz, 1H), 6.68 (dd, J=8.0, 1.2 Hz, 1H), 5.95 (s, 2H) 4.19-4.14 (m, 1H), 3.62 (s, 3H), 3.49 (s, 3H), 2.94 (dd, J=12, 4.8 Hz, 1H) and 2.75 (dd, J=16, 10.4 Hz, 1H) Step 3

Step 3 was first attempted using $KBH_4$ (1.2 eq). A small amount of the desired product was observed by LC/MS after 5 hours at 0° C. to room temperature. After addition of more $KBH_4$ and stirring for 24 hours, no improvement in the conversion was found. Step 3 was then attempted using $NaBH_4$ (1.2 eq). There was 8% product observed by LC/MS after stirring for 3.5 hours at room temperature. After adding more $NaBH_4$ (2.8 eq) and stirring for 24 hours at room temperature, ~40% of product was detected by LC/MS. Better yields were obtained using $LiAlH_4$ using the following process.

To a 1000 mL 3-necked round bottom flask equipped with thermometer and Argon inlet/outlet was charged 250 mL of anhydrous THF followed by portion-wise addition of $LiAlH_4$ (2.65 g; 0.070 mol; 1.06 Eq.) under an Argon blanket. The mixture was stirred until a uniform suspension is formed. The LAH suspension was cooled to 0-5° C. in an ice bath and a solution of the product of step 2 (18.5 g; 0.066 mol; 1.0 Eq) in 250 mL of anhydrous THF was added slowly via additional funnel while keeping the internal temperature less than 10° C. Once addition of the product of step 2 is complete, removed the cooling bath and stirred the reaction mixture at room temperature for 1 hr or until complete by TLC. Cooled the reaction mixture to 0-5° C. in an ice bath and quenched the reaction by dropwise addition of 1:1 Water:THF (5.5 mL), 15% NaOH (3.0 mL) and Water (8.0 mL). Stirred the mixture for 30 minutes then filtered over sand to remove the inorganic salts. The filtrate was concentrated in vacuo and the crude product was purified by silica gel chromatography to afford the product of step 3 (12.8 g; 75%) as a clear colourless oil.

1H-NMR (400 Hz, DMSO-d6) δ (ppm): 6.92 (d, J=8.4 Hz, 1H), 6.80 (d, J=8.0 Hz, 1H), 6.77 (d, J=1.6 Hz, 1H), 6.66 (dd, J=8.0, 1.6 Hz, 1H), 5.96 (s, 2H), 4.74 (t, J=5.6 Hz, 1H), 4.61-3.53 (m, 1H), 3.47 (s, 3H), 3.38-3.34 (m, 1H), 3.32-3.26 (m, 1H), 2.77 (dd, J=12, 5.2 Hz, 1H) and 2.54-247 (m, 1H).

Step 4

Transferred to a 3-necked round bottom flask equipped with stir bar, thermometer and Argon inlet/outlet. Dissolved the product of step 3 (12.8 g; 0.051 mol; 1.0 Eq.) in anhydrous THF (300 mL). Cooled the solution to 0-5° C. in an ice bath and added thionyl Chloride (12.05 g; 0.102 mol; 2.0 Eq.). Removed cooling bath and stirred the reaction mixture well at room temperature for 16 hrs. Concentrated the reaction mixture in vacuo to dryness and purified the crude product by silica gel chromatography to afford the product of step 4 (8.3 g; 60%) as a light yellow solid.

$^1$H-NMR (400 Hz, DMSO-$d_6$) δ (ppm): 7.33 (d, J=8 Hz, 1H), 6.82 (d, J=6 Hz, 1H), 6.81 (s, 1H), 6.68 (dd, J=8.0, 1.2 Hz, 1H), 5.97 (s, 2H), 3.86-3.77 (m, 1H), 3.64 (dd, J=12, 4.6 Hz, 1H), 3.55 (dd, J=12, 5.8 Hz, 1H) 3.48 (s, 3H), 2.75 (dd, J=16, 5.4 Hz, 1H) and 2.62 (dd, J=12, 8.8 Hz, 1H).

Step 5

To a 500 mL 3-necked round bottom flask equipped with thermometer and Argon inlet/outlet was charged 150 mL of anhydrous THF followed by portion-wise addition of $LiAlH_4$ (LAH) (2.35 g; 0.062 mol; 2.0 Eq.) under an Argon blanket. The mixture was stirred until a uniform suspension is formed. The LAH suspension was cooled to 0-5° C. in an ice bath and a solution of product of step 4 (8.3 g; 0.031 mol; 1.0 Eq) in 100 mL of anhydrous THF was added slowly via additional funnel while keeping the internal temperature less than 10° C. Once addition of product of step 4 is complete, removed the cooling bath and stirred the reaction mixture at reflux for 2 hrs or until complete by TLC. Cooled the reaction mixture to 0-5° C. in an ice bath and quenched the reaction by dropwise addition of 1:1 Water:THF (4.7 mL), 15% NaOH (2.4 mL) and Water (7.0 mL). Stirred the mixture for 30 minutes then filtered over sand to remove the inorganic salts. The filtrate was concentrated in vacuo and the crude product was purified by silica gel chromatography to afford (R)-MDMA (free base) (4.0 g; 65%) as a clear colourless oil.

Step 6

A solution of (R)-MDMA (free base) (4.0 g; 0.021 mol; 1.0 Eq.) in IPA (20 mL) in a 250 mL round bottom flask was cooled to 0-5° C. in an ice/water bath. Concentrated HCl (1.7 mL; 0.021 mol; 1.0 Eq.) was added dropwise to the reaction solution and solids began to form immediately. Once addition of the HCl was completed, the suspension was stirred for 20 mins then MTBE (30 mL) was added and stirring was continued for another 1 hr. The cooled suspension was filtered and the solid washed with MTBE (2×30 mL). The solid was transferred to a 20 mL vial and dried under high vacuum for 1 hr to afford the final product (R)-MDMA·HCl (4.0 g; 83%) as a white solid.

$^1$H-NMR (400 Hz, $CDCl_3$) δ (ppm): 9.65 (br, 2H), 6.74-6.65 (m, 3H), 5.93 (s, 2H), 3.38 (dd, J=12, 4 Hz, 1H), 3.28-3.24 (m, 1H), 2.75 (dd, J=16, 10.6 Hz, 1H). 2.69 (t, J=5.4, 3H) and 1.33 (d, J=6.4 Hz, 3H)

HPLC: Chiral Column: Lux 3 μm AMP, 150×4.6 mm, ee 97.5%

Example 8: Exemplary Process for Preparing (S)-MDMA (S)-MDMA is prepared according to the following synthetic scheme.

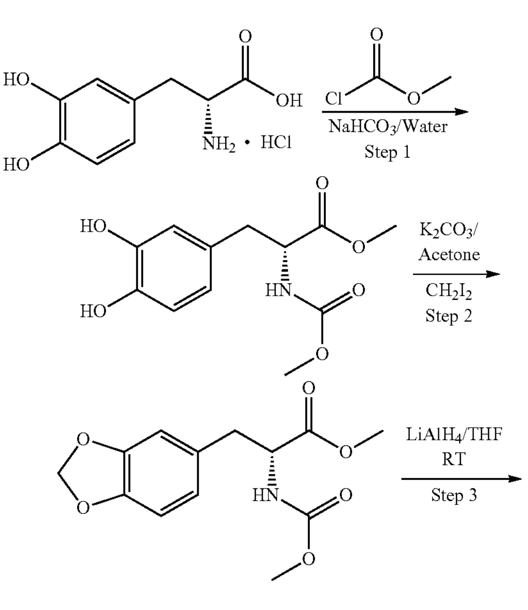

-continued

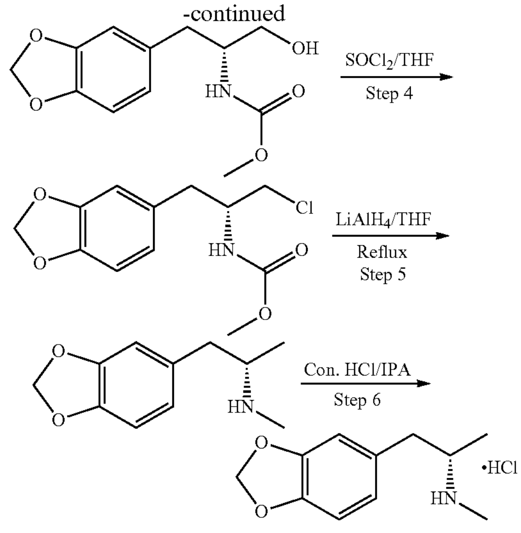

(S)-MDMA

Step 1

D-DOPA methyl ester (44.5 g; 0.180 mol; 1.0 Eq.) is added to a 3 L round bottom flask containing a large stir bar and dissolved in USP Purified Water (1000 mL). sodium bicarbonate (30.0 g; 0.360 mol; 2.0 Eq.) is added to the solution followed by addition of a solution of methyl chloroformate (20.4 g; 0.216 mol; 1.2 Eq.) in THF (600 mL) via an additional funnel. The resulting mixture is then stirred at room temperature for at least 24 hours. The reaction is monitored for completion by TLC. The volatiles are evaporated, and the resulting aqueous phase is extracted with EtOAc (3×500 mL). The combined organic phases are washed with water (500 mL), 5% HCl (500 mL) and brine (500 mL), then dried over anhydrous $Na_2SO_4$ and concentrated in vacuo, affording the product of step 1.

Step 2

The product of step 1 (53.0 g Crude; 0.180 mol; 1.0 Eq.) is transferred to a 3 L-3 necked round bottom flask equipped with large stir bar, thermometer and condenser using Acetone (1400 mL). Potassium Carbonate (92.4 g; 0.669 mol; 3.7 Eq.) and Diiodomethane (116 g; 0.433 mol; 2.4 Eq.) are added to the solution of the product of step 1 and the reaction mixture is heated to reflux for 16 hours or until TLC shows the reaction is complete. Potassium Carbonate is removed by filtration and the filtrate is evaporated to dryness in vacuo. The resulting crude is purified by silica gel chromatography using a 0-10% Acetone/DCM gradient eluent to provide pure product of step 2 as a white solid.

Step 3

To a 1000 mL 3-necked round bottom flask equipped with thermometer and Argon inlet/outlet is charged 250 mL of anhydrous THF followed by portion-wise addition of $LiAlH_4$ (2.65 g; 0.070 mol; 1.06 Eq.) under an Argon blanket. The mixture is stirred until a uniform suspension is formed. The LAH suspension is cooled to 0-5° C. in an ice bath and a solution of the product of step 2 (18.5 g; 0.066 mol; 1.0 Eq) in 250 mL of anhydrous THF is added slowly via additional funnel while keeping the internal temperature less than 10° C. Once addition of the product of step 2 is complete, remove the cooling bath and stir the reaction mixture at room temperature for 1 hr or until complete by TLC. Cool the reaction mixture to 0-5° C. in an ice bath and quench the reaction by dropwise addition of 1:1 Water:THF (5.5 mL), 15% NaOH (3.0 mL) and Water (8.0 mL). Stir the mixture for 30 minutes then filter over sand to remove the inorganic salts. The filtrate is concentrated in vacuo and the crude product is purified by silica gel chromatography to afford the product of step 3.

Step 4

Transfer to a 3-necked round bottom flask equipped with stir bar, thermometer and Argon inlet/outlet. Dissolve the product of step 3 (12.8 g; 0.051 mol; 1.0 Eq.) in anhydrous THF (300 mL). Cool the solution to 0-5° C. in an ice bath and add Thionyl Chloride (12.05 g; 0.102 mol; 2.0 Eq.). Remove cooling bath and stir the reaction mixture well at room temperature for 16 hrs. Concentrate the reaction mixture in vacuo to dryness and purify the crude product by silica gel chromatography to afford the product of step 4.

Step 5

To a 500 mL 3-necked round bottom flask equipped with thermometer and Argon inlet/outlet is charged 150 mL of anhydrous THF followed by portion-wise addition of $LiAlH_4$ (LAH) (2.35 g; 0.062 mol; 2.0 Eq.) under an Argon blanket. The mixture is stirred until a uniform suspension is formed. The LAH suspension is cooled to 0-5° C. in an ice bath and a solution of product of step 4 (8.3 g; 0.031 mol; 1.0 Eq) in 100 mL of anhydrous THF is added slowly via additional funnel while keeping the internal temperature less than 10° C. Once addition of product of step 4 is complete, remove the cooling bath and stir the reaction mixture at reflux for 2 hrs or until complete by TLC. Cool the reaction mixture to 0-5° C. in an ice bath and quench the reaction by dropwise addition of 1:1 Water:THF (4.7 mL), 15% NaOH (2.4 mL) and Water (7.0 mL). Stir the mixture for 30 minutes then filter over sand to remove the inorganic salts. The filtrate is concentrated in vacuo and the crude product is purified by silica gel chromatography to afford (S)-MDMA (free base).

Step 6

A solution of (S)-MDMA (free base) (4.0 g; 0.021 mol; 1.0 Eq.) in IPA (20 mL) in a 250 mL round bottom flask is cooled to 0-5° C. in an ice/water bath. Concentrated HCl (1.7 mL; 0.021 mol; 1.0 Eq.) is added dropwise to the reaction solution and solids begin to form immediately. Once addition of the HCl is complete, stir the suspension for 20 mins then add MTBE (30 mL) and continue stirring for another 1 hr. The suspension is cooled and filtered and the solid is washed with MTBE (2×30 mL). The solid is transferred to a 20 mL vial and dried under high vacuum for 1 hr to afford the final product (S)-MDMA·HCl.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A process for preparing a compound of Formula (R)-I or (S)-I:

(R)-I

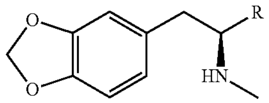

or

-continued (S)-I

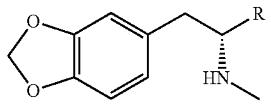

wherein

R is selected from $CH_3$ and $CH_2CH_3$;

the process comprising:

protecting the amino group of 3,4-dihydroxy-L-phenylalanine (L-DOPA) $C_{1-4}$alkyl ester of Formula (S)-A, or the amino group of 3,4-dihydroxy-D-phenylalanine (D-DOPA) $C_{1-4}$alkyl ester of Formula (R)-A:

(S)-A

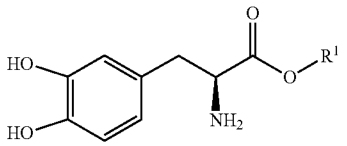

or (R)-A

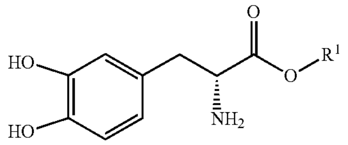

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

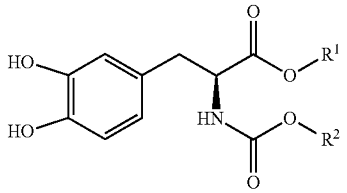

or (R)-B

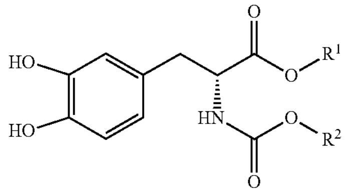

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

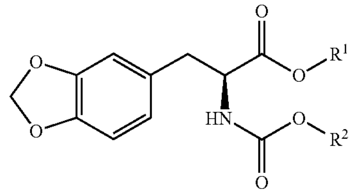

or (R)-C

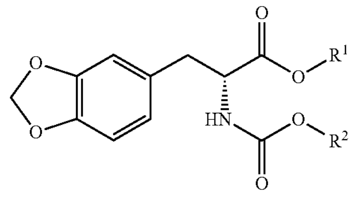

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

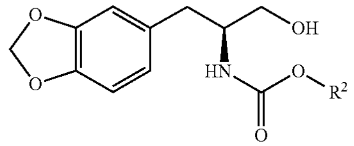

or (R)-D

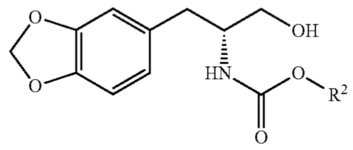

wherein $R^2$ is $C_{1-4}$alkyl or $CH_2Ph$;

when R is $CH_2CH_3$, further oxidizing the compound of Formula (S)-D or (R)-D to provide a compound of Formula (S)-$D^{ox}$ or (R)-$D^{ox}$, respectively; and (S)-$D^{ox}$

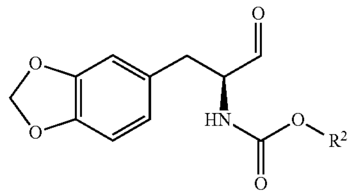

or (R)-$D^{ox}$

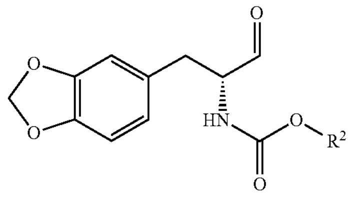

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

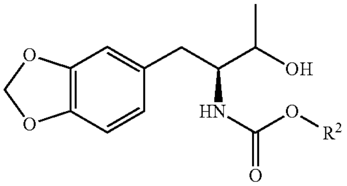

or (R)-D'

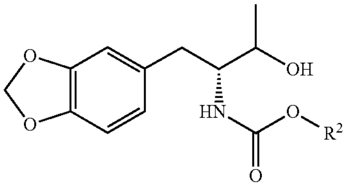

wherein $R^2$ is $C_{1-4}$alkyl or $CH_2Ph$; and reacting the compound of Formula (S)-D or (R)-D with a chlorinating agent to provide a compound of Formula (S)-E or (R)-E, respectively, or reacting the compound Formula of(S)-D' or (R)-D' with a chlorinating agent to provide a compound of Formula (S)-E' or (R)-E', respectively:

(S)-E

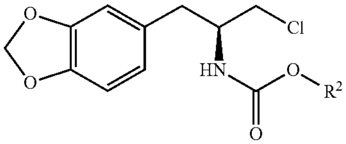

or (R)-E

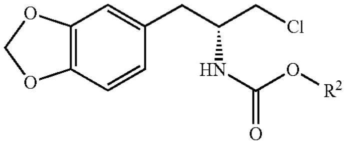

or (S)-E'

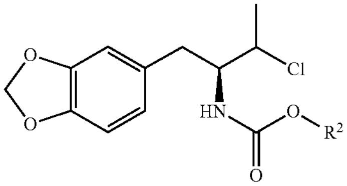

or (R)-E'

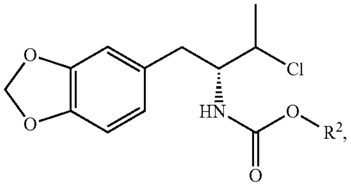

wherein $R^2$ is $C_{1-4}$alkyl or $CH_2Ph$; or when R is $CH_2CH_3$, hydrolyzing the compound of Formula (S)-C or (R)-C to provide the compound of Formula (S)-C' or (R)-C', respectively;

(S)-C'

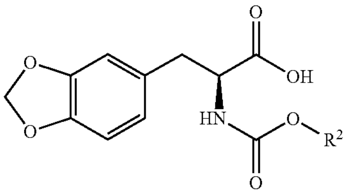

or (R)-C'

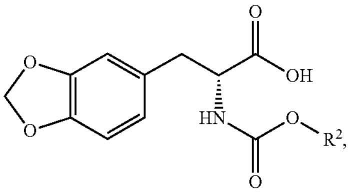

wherein $R^2$ is $C_{1-4}$alkyl or $CH_2Ph$; and converting the compound of Formula (S)-C' or (R)-C' to the compound of Formula (S)-E" or (R)-E", respectively (S)-E"

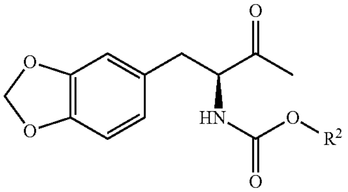

or (R)-E"

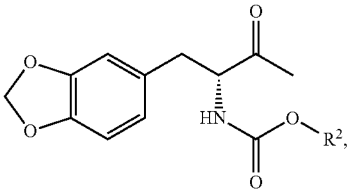

wherein $R^2$ is $C_{1-4}$alkyl or $CH_2Ph$; and reacting the compound of Formula (S)-E or (R)-E with a reducing agent to provide the compound of Formula (R)-I or (S)-I, respectively, wherein R is $CH_3$, reacting the compound of Formula (S)-E' or (R)-E' with a reducing agent to provide the compound of Formula (R)-I or (S)-I, respectively, wherein R is $CH_2CH_3$, or reacting the compound of Formula (S)-E" or (R)-E" with a reducing agent to provide the compound of Formula (R)-I or (S)-I, respectively, wherein R is $CH_2CH_3$.

2. The process of claim 1, wherein R is $CH_3$ and the process is a process for preparing (R)-3,4-methylenedioxymethamphetamine ((R)-MDMA) or (S)-3,4-methylenedioxymethamphetamine ((S)-MDMA)

(R)-MDMA

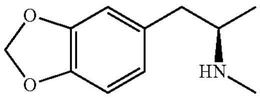

or

-continued (S)-MDMA

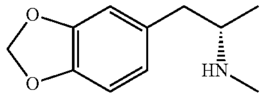

comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

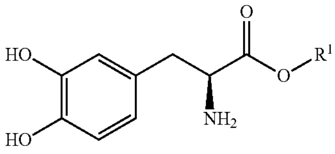

or (R)-A

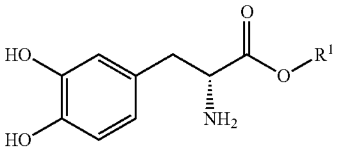

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

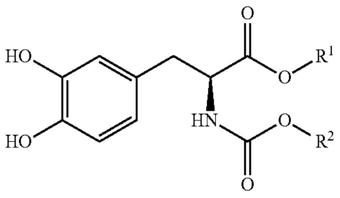

or (R)-B

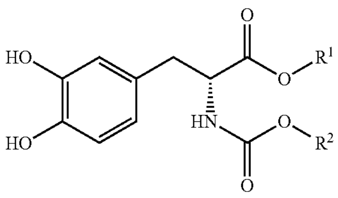

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C respectively:

(S)-C

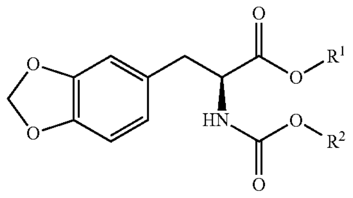

or (R)-C

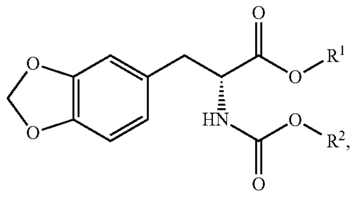

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

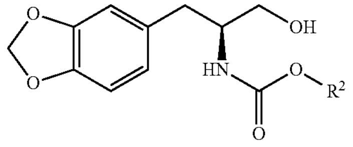

or (R)-D

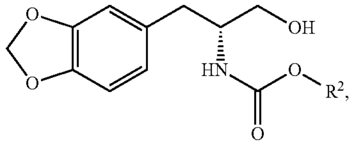

wherein $R^2$ is $C_{1-4}$alkyl or $CH_2Ph$;

reacting the compound of Formula (S)-D or (R)-D with a chlorinating agent to provide a compound of Formula (S)-E or (R)-E, respectively:

(S)-E

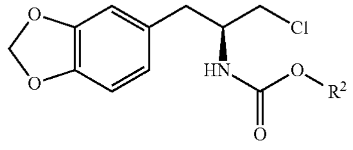

or (R)-E

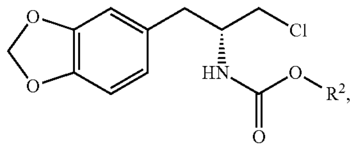

wherein $R^2$ is $C_{1-4}$alkyl or $CH_2Ph$; and reacting the compound of Formula (S)-E or (R)-E with a reducing agent to provide the (R)-MDMA or (S)-MDMA, respectively.

3. The process of claim 1 wherein R is $CH_2CH_3$ and the process is for preparing (R)—N-methyl-1,3-benzodioxolylbutanamine ((R)-MBDB) or (S)-N-methyl-1,3-benzodioxolylbutanamine ((S)-MBDB):

(R)-MBDB

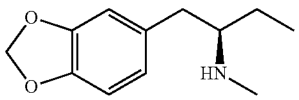

or (S)-MBDB

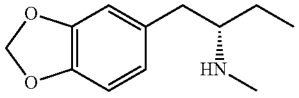

comprising:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

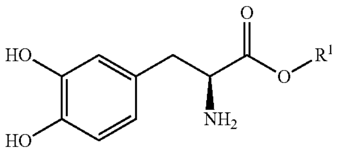

or (R)-A

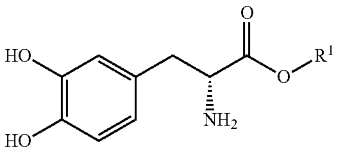

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

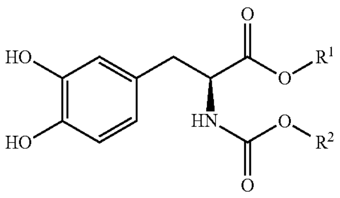

or (R)-B

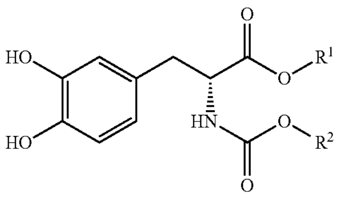

wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C, respectively:

(S)-C

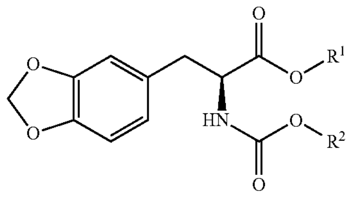

or (R)-C

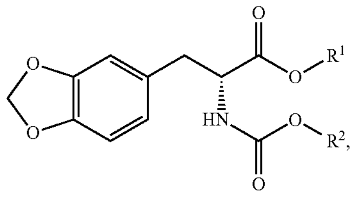

wherein $R^1$ is $C_{1-4}$alkyl, and $R^2$ is $C_{1-4}$alkyl or $CH_2Ph$;

reacting the compound of Formula (S)-C or (R)-C with a reducing agent to provide a compound of Formula (S)-D or (R)-D, respectively:

(S)-D

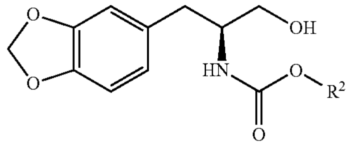

or (R)-D

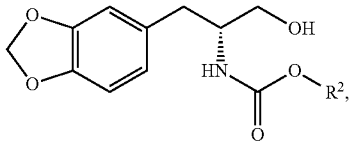

wherein $R^2$ is $C_{1-4}$alkyl or $CH_2Ph$;

oxidizing the compound of Formula (S)-D or (R)-D to provide a compound of Formula (S)-$D^{ox}$ or (R)-$D^{ox}$, respectively;

(S)-$D^{ox}$

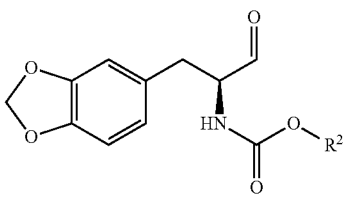

or (R)-$D^{ox}$

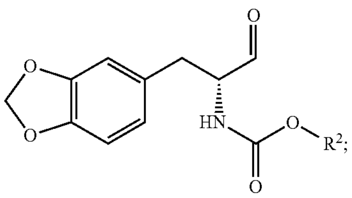

wherein $R^2$ is $C_{1-4}$alkyl or $CH_2Ph$;

reacting the compound of Formula (S)-$D^{ox}$ or (R)-$D^{ox}$ with a methyl organometallic reagent to provide the compound of Formula (S)-D' or (R)-D', respectively;

(S)-D'

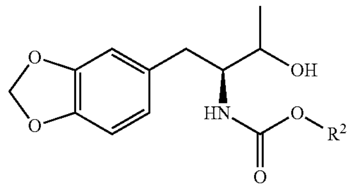

or (R)-D'

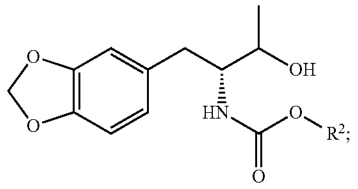

wherein $R^2$ is $C_{1-4}$alkyl or $CH_2Ph$;

reacting the compound of Formula (S)-D' or (R)-D' with a chlorinating agent to provide a compound of Formula (S)-E' or (R)-E', respectively:

(S)-E'

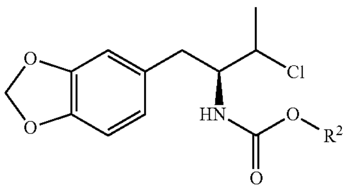

or (R)-E'

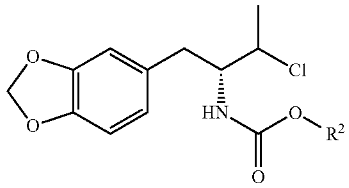

wherein $R^2$ is $C_{1-4}$alkyl or $CH_2Ph$; and reacting the compound of Formula (S)-E' or (R)-E' with a reducing agent to provide (R)-MBDB or (S)-MBDB, respectively.

4. The process of claim 1, wherein R is $CH_2CH_3$ and the process is for preparing (R)—N-methyl-1,3-benzodioxolylbutanamine ((R)-MBDB) or (S)-N-methyl-1,3-benzodioxolylbutanamine ((S)-MBDB):

(R)-MBDB

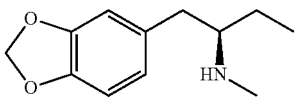

or (S)-MBDB

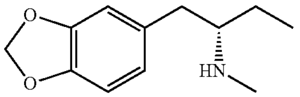

, and the process comprises:

protecting the amino group of 3,4-dihydroxy-L-phenylalanine (L-DOPA) $C_{1-4}$alkyl ester of Formula (S)-A or the amino group of 3,4-dihydroxy-D-phenylalanine (D-DOPA) $C_{1-4}$alkyl ester of Formula (R)-A:

(S)-A

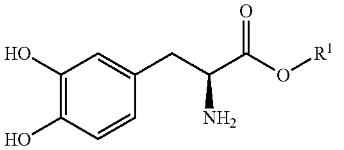

(R)-A

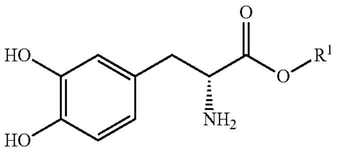

wherein $R^1$ is $C_{1-4}$alkyl, with a $C_{1-4}$alkoxycarbonyl protecting group or a benzyloxy carbonyl protecting group to provide a compound of Formula (S)-B or (R)-B, respectively:

(S)-B

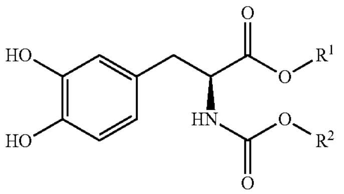

or (R)-B

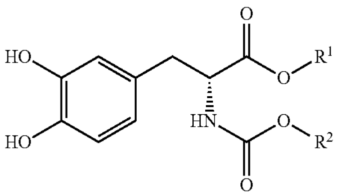

, wherein $R^1$ is $C_{1-4}$alkyl, and $R^2$ is $C_{1-4}$alkyl or $CH_2Ph$;

cyclizing the compound of Formula (S)-B or (R)-B to provide a compound of Formula (S)-C or (R)-C respectively:

(S)-C

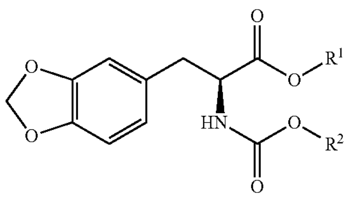

or

-continued (R)-C

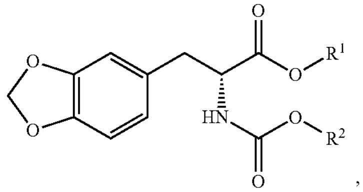

, wherein $R^1$ is $C_{1-4}$alkyl, and $R^2$ is $C_{1-4}$alkyl or $CH_2Ph$;

hydrolyzing the compound of Formula (S)-C or (R)-C to provide the compound of Formula (S)-C' or (R)-C', respectively;

(S)-C'

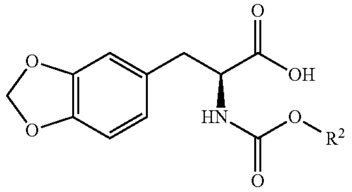

or (R)-C'

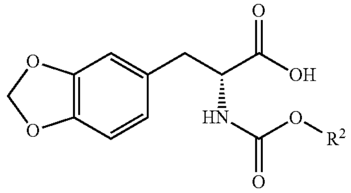

, wherein $R^2$ is $C_{1-4}$alkyl or $CH_2Ph$;

converting the compound of Formula (S)-C' or (R)-C' to the compound of Formula (S)-E" or (R)-E", respectively (S)-E''

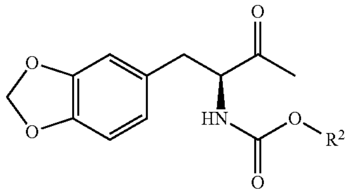

or (R)-E''

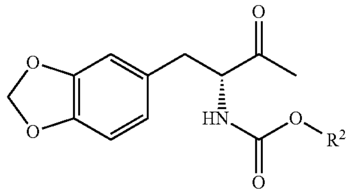

, wherein $R^2$ is $C_{1-4}$alkyl or $CH_2Ph$; and reacting the compound of Formula (S)-E" or (R)-E" with a reducing agent to provide (R)-MBDB or (S)-MBDB, respectively.

5. The process of claim 1, wherein the $C_{1-4}$alkoxycarbonyl protecting group is methoxycarbonyl or ethoxycarbonyl.

6. The process of claim 1, wherein the reducing agent to provide the compound of Formula (R)-I or (S)-I from the compound of Formula (S)-E or (R)-E, the compound of Formula (S)-E' or (R)-E' or the compound of Formula (S)-E" or (R)-E", respectively is a metal hydride.

7. The process of claim 6, wherein the reducing agent for reacting with the compound of Formula (S)-C or (R)-C to provide the compound of Formula (S)-D or (R)-D, respectively is lithium aluminium hydride.

8. The process of claim 1, wherein the chlorinating reagent is selected from thionyl chloride ($SOCl_2$), phosphorus trichloride ($PCl_3$), phosphorus pentachloride ($PCl_5$) and oxalyl chloride $(COCl)_2$.

9. The process of claim 8, wherein the chlorinating reagent is $SOCl_2$.

10. The process of claim 1, wherein reacting the compound of Formula (S)-E or (R)-E or the compound of Formula (S)-E' or (R)-E' with a reducing agent to provide the compound of Formula (R)-I or (S)-I respectively comprises reacting the compound of Formula (S)-E or (R)-E or a compound of Formula (S)-E' or (R)-E' with a first reducing agent to provide a compound of Formula (S)-F or (R)-F, respectively;

(S)-F

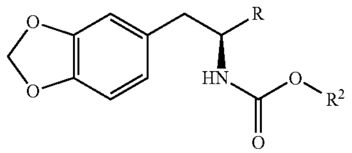

or (R)-F

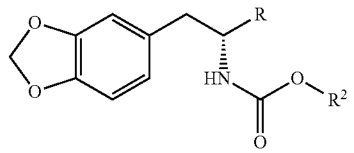

, wherein R is selected from $CH_3$ and $CH_2CH_3$;

$R^2$ is $C_{1-4}$alkyl or $CH_2Ph$; and reacting the compound of Formula (S)-F or (R)-F with a second reducing agent to provide the compound of Formula (R)-I or (S)-I, respectively.

11. The process of claim 4, wherein the step of converting the compound of Formula (S)-C' or (R)-C' to the compound of Formula (S)-E" or (R)-E" comprises;

reacting the compound of Formula (S)-C' or (R)-C' with N, O-dimethylhydroxylamine,

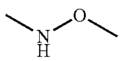

, to provide the amide compound of Formula (S)-E'" or (R)-E'", respectively (S)-E''

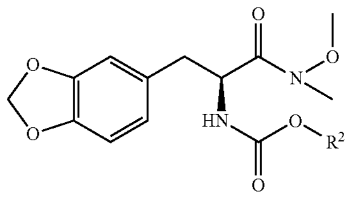

or

-continued (R)-E'''

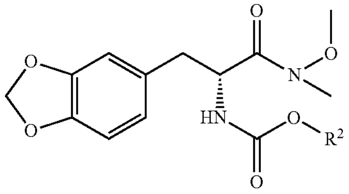

, wherein $R^2$ is $C_{1-4}$alkyl or $CH_2Ph$; and reacting the compound of Formula (S)-E" or (R)-E''' with a methyl organometallic reagent to provide the compound of Formula (S)-E" or (R)-E"

(S)-E''

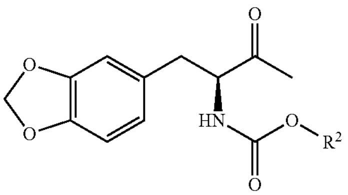

or (R)-E''

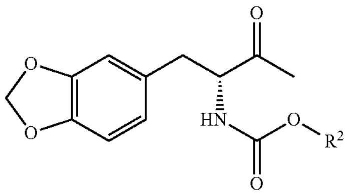

, wherein $R^2$ is $C_{1-4}$alkyl or $CH_2Ph$.

12. The process of claim 3, wherein the compound of Formula (S)-D or (R)-D is oxidized in the presence of a suitable oxidizing agent in a suitable inert solvent for a time and a temperature to provide the compound of formula (S)-$D^{ox}$ or (R)-$D^{ox}$, respectively, wherein the suitable oxidizing agent is phosgene, Dess-Martin periodinane, sodium hypochlorite with 2,2,6,6-tetramethylpiperidin-1-yl)oxyl or (2,2,6,6-tetramethylpiperidin-1-yl)oxidanyl (TEMPO) or oxalyl chloride with dimethylsulfoxide.

13. The process of claim 1, wherein the process provides compound of Formula (R)-I or (S)-I in greater than 60% ee, 65% ee, 70% ee, 75% ee, 80% ee, 85% ee, 90% ee, 95% ee, 98% ee or 99% ee.

14. The process of claim 1, wherein the compound of Formula (R)-I or (S)-I is further converted to a pharmaceutically acceptable salt, solvate and/or prodrug thereof.

15. The process of claim 2, wherein in the process is for preparing (R)-3,4-methylenedioxymethamphetamine ((R)-MDMA):

(R)-MDMA

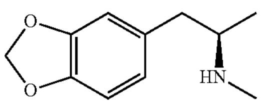

, the process comprising:

protecting the amino group of the compound of Formula (S)-A:

(S)-A

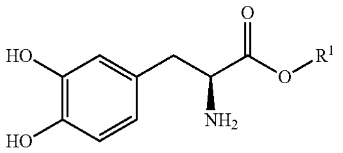

wherein $R^1$ is $CH_3$ or $CH_2CH_3$;

with a methoxycarbonyl protecting group or ethoxycarbonyl protecting group to provide the compound of Formula (S)-B:

(S)-B

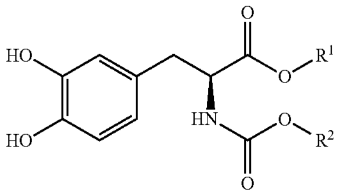

wherein $R^1$ is $CH_3$ or $CH_2CH_3$, and $R^2$ is $CH_3$ or $CH_2CH_3$;

cyclizing the compound of Formula (S)-B to provide the compound of Formula (S)-C:

(S)-C

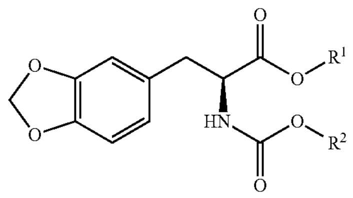

, wherein $R^1$ is $CH_3$ or $CH_2CH_3$; and $R^2$ is $CH_3$ or $CH_2CH_3$;

reacting the compound of Formula (S)-C with a reducing agent to provide the compound of Formula (S)-D:

(S)-D

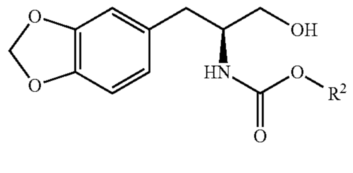

, wherein $R^2$ is $CH_3$ or $CH_2CH_3$;

reacting the compound of Formula (S)-D with a chlorinating agent to provide the compound of Formula (S)-E:

(S)-E

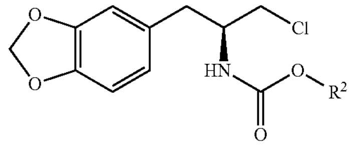

, wherein $R^2$ is $CH_3$ or $CH_2CH_3$; and reacting the compound of Formula (S)-E with a reducing agent to provide the (R)-MDMA.

16. The process of claim 3, wherein the process is for preparing (R)—N-methyl-1,3-benzodioxolylbutanamine ((R)-MBDB)

(R)-MBDB

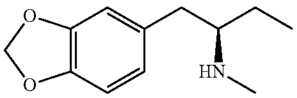

the process comprising:

protecting the compound of Formula (S)-A:

(S)-A

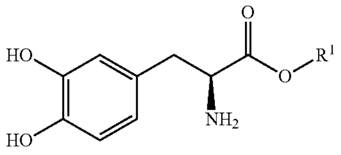

wherein $R^1$ is $CH_3$ or $CH_2CH_3$, with a methoxycarbonyl protecting group or ethoxycarbonyl protecting group to provide the compound of Formula (S)-B:

(S)-B

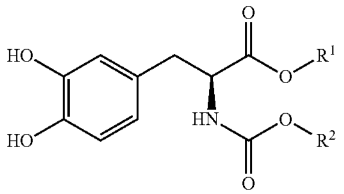

wherein $R^1$ is $CH_3$ or $CH_2CH_3$, and $R^2$ is $CH_3$ or $CH_2CH_3$;

cyclizing the compound of Formula (S)-B to provide the compound of Formula (S)-C:

(S)-C

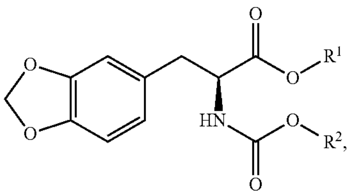

wherein $R^1$ is $CH_3$ or $CH_2CH_3$, and $R^2$ is $CH_3$ or $CH_2CH_3$;

reacting the compound of Formula (S)-C with a reducing agent to provide the compound of Formula (S)-D:

(S)-D

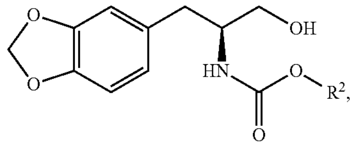

wherein $R^2$ is $CH_3$ or $CH_2CH_3$ oxidizing the compound of Formula (S)-D to provide the compound of Formula (S)-$D^{ox}$;

(S)-$D^{ox}$-

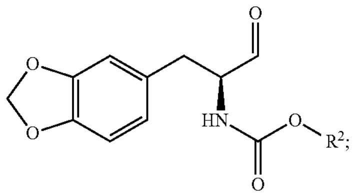

wherein $R^2$ is $CH_3$ or $CH_2CH_3$;

reacting the compound of Formula (S)-$D^{ox}$ with a methyl organometallic reagent to provide the compound of Formula (S)-D';

(S)-D'

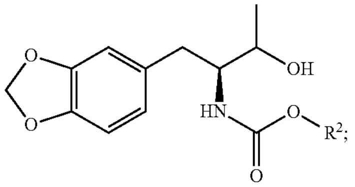

wherein $R^2$ is $CH_3$ or $CH_2CH_3$;

reacting the compound of Formula (S)-D' with a chlorinating agent to provide the compound of Formula (S)-E':

(S)-E'

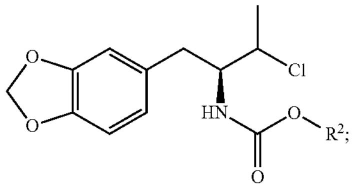

wherein $R^2$ is $CH_3$ or $CH_2CH_3$; and reacting the compound of Formula (S)-E' with a reducing agent to provide the (R)-MBDB.

17. The process of claim 4, wherein the process is for preparing (R)—N-methyl-1,3-benzodioxolylbutanamine ((R)-MBDB)

(R)-MBDB

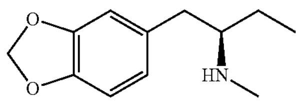

the process comprising:

protecting the amino group of 3,4-dihydroxy-L-phenylalanine (L-DOPA) $C_{1-4}$alkyl ester of Formula (S)-A:

(S)-A

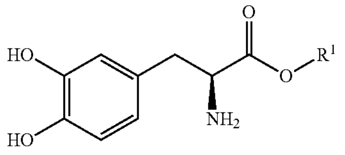

wherein $R^1$ is $CH_3$ or $CH_2CH_3$, with a methoxycarbonyl or ethoxycarbonyl protecting group or a benzyloxy carbonyl protecting group to provide the compound of Formula (S)-B:

(S)-B

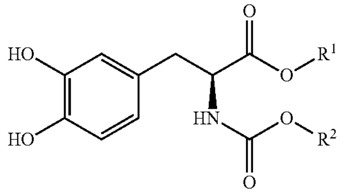

wherein $R^1$ is $CH_3$ or $CH_2CH_3$; and $R^2$ is $CH_3$ or $CH_2CH_3$;

cyclizing the compound of Formula (S)-B to provide the compound of Formula (S)-C:

(S)-C

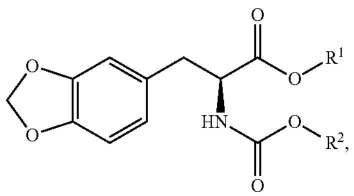

wherein $R^1$ is $CH_3$ or $CH_2CH_3$; and $R^2$ is $CH_3$ or $CH_2CH_3$;

hydrolyzing the compound of Formula (S)-C to provide the compound of Formula (S)-C';

(S)-C'

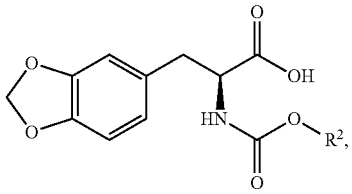

wherein $R^2$ is $CH_3$ or $CH_2CH_3$;

converting the compound of Formula (S)-C' to the compound of Formula (S)-E"

(S)-E"

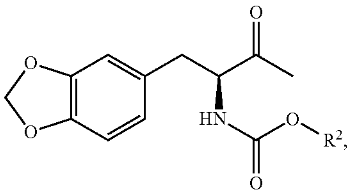

wherein $R^2$ is $CH_3$ or $CH_2CH_3$; and reacting the compound of Formula (S)-E" with a reducing agent to provide the (R)-MBDB.

18. A compound of Formula (S)-C or (R)-C:

(S)-C

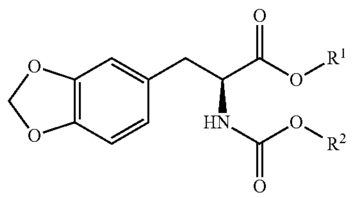

or (R)-C

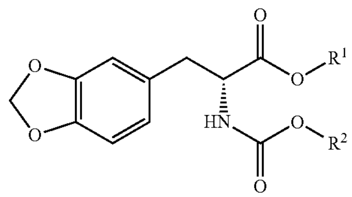

wherein $R^1$ is $C_{1-4}$alkyl; and $R^2$ is $CH_3$; or $R^1$ is $CH_2CH_3$ and $R^2$ is $CH_2CH_3$; or a compound of Formula (S)-C' or (R)-C':

(S)-C'

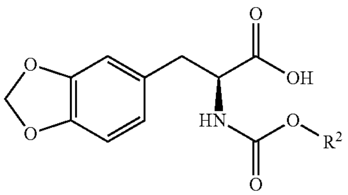

or

-continued (R)-C′

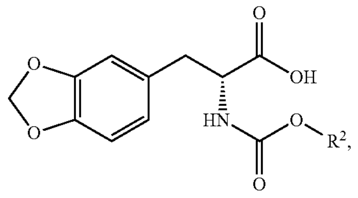

wherein $R^2$ is $CH_3$; or a compound of Formula (S)-D or (R)-D:

(S)-D

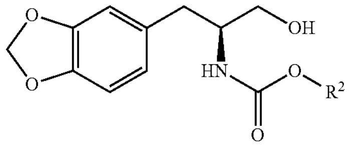

or (R)-D

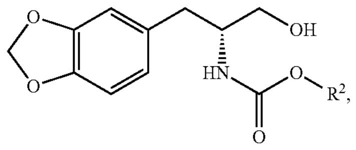

wherein $R^2$ is $CH_3$ or $CH_2CH_3$; or a compound of Formula (S)-D' or (R)-D';

(S)-D′

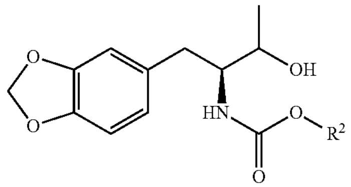

or (R)-D′

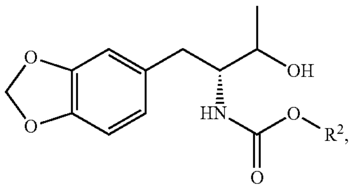

wherein $R^2$ is $CH_3$, $CH_2CH_3$ or $C(CH_3)_3$; or a compound of Formula (S)-$D^{ox}$ or (R)-$D^{ox}$;

(S)-$D^{ox}$

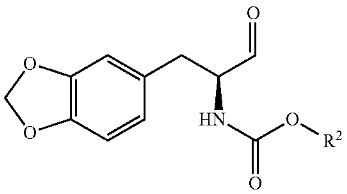

or

-continued (R)-$D^{ox}$

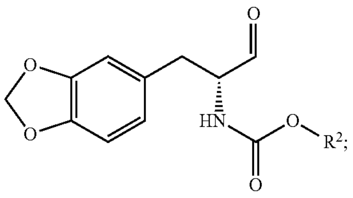

wherein $R^2$ is $CH_3$.

19. The compound of claim 18, wherein $R^1$ and $R^2$ are both $CH_3$ and the compound of Formula (S)-C or (R)-C has the following structure:

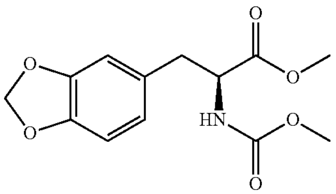

or

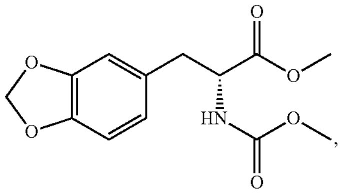

respectively.

20. A compound of Formula (S)-E or (R)-E (S)-E

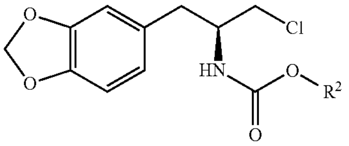

or (R)-E

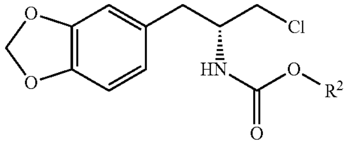

wherein $R^2$ is $CH_3$, $CH_2CH_3$ or $CH_2Ph$, or a compound of Formula (S)-E' or (R)-E'

(S)-E′

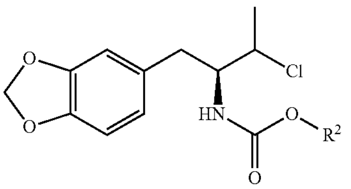

or

-continued
(R)-E′
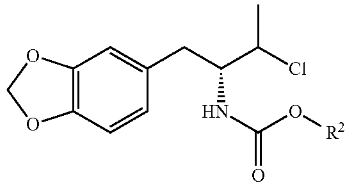
wherein $R^2$ is $CH_3$; or
a compound of Formula (S)-E" or (R)-E"
(S)-E″
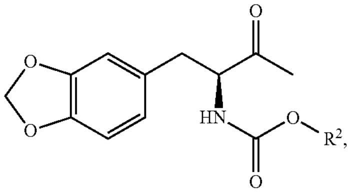
or
(R)-E″
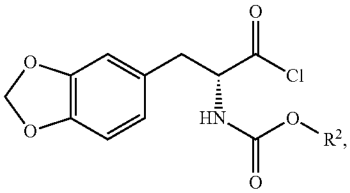
wherein $R^2$ is $CH_3$; or
a compound of Formula (S)-E" or (R)-E"
(S)-E‴
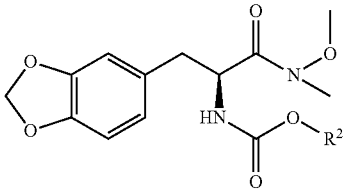
or
-continued
(R)-E‴
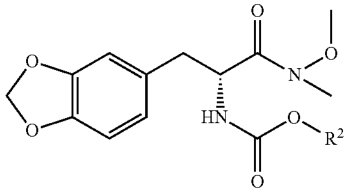
wherein $R^2$ is $CH_3$; or
a compound of Formula (S)-F or (R)-F:
(S)-F
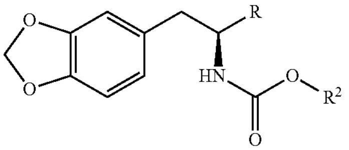
or
(R)-F
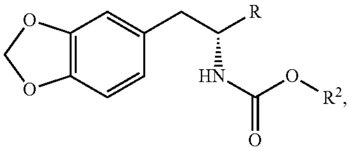
wherein R is $CH_3$ or $CH_2CH_3$; and
$R^2$ is $CH_3$ or $CH_2Ph$.
* * * * *